United States Patent [19]
Talley et al.

[11] Patent Number: 5,565,482
[45] Date of Patent: Oct. 15, 1996

[54] HETEROARYLPYRANOPYRAZOLYL DERIVATIVES FOR THE TREATMENT OF INFLAMMATION

[75] Inventors: John J. Talley; Stephen R. Bertenshaw, both of Brentwood; Matthew J. Graneto, St. Louis; Donald J. Rogier, Chesterfield, all of Mo.

[73] Assignee: G.D. Searle & Co., Skokie, Ill.

[21] Appl. No.: 536,925

[22] Filed: Sep. 29, 1995

Related U.S. Application Data

[62] Division of Ser. No. 309,291, Sep. 20, 1994.

[51] Int. Cl.$^6$ .................. A61K 31/415; C07D 491/14
[52] U.S. Cl. .................. 514/406; 546/83; 546/194; 548/126; 548/151; 548/207; 548/218; 548/242; 548/256; 548/302.1; 548/358.5; 548/359.5
[58] Field of Search .................. 548/358.5, 359.5; 546/83; 514/406

[56] References Cited

U.S. PATENT DOCUMENTS

| | | |
|---|---|---|
| 3,940,418 | 2/1976 | Hamilton . |
| 4,678,499 | 7/1987 | Pasteris et al. . |
| 4,803,193 | 2/1989 | Kanda et al. . |
| 4,816,467 | 3/1989 | Doria et al. . |
| 5,206,258 | 4/1993 | Doria et al. . |
| 5,260,328 | 11/1993 | Doria et al. . |

FOREIGN PATENT DOCUMENTS

| | | |
|---|---|---|
| 347773 | 12/1989 | European Pat. Off. . |
| 2227741 | 8/1990 | United Kingdom . |

OTHER PUBLICATIONS

V. Colotta et al, *J. Med. Chem.*, 33:2646–2651 (1990).
F. Melani et al, *J. Med. Chem.*, 29:291–295 (1986).
G. Doria et al, *Il Farmaco*, 46(7,8), 843–860 (1991).

*Primary Examiner*—Robert W. Ramsuer
*Attorney, Agent, or Firm*—Joseph W. Bulock; J. Timothy Keane

[57] ABSTRACT

A class of benzopyranopyrazolyl derivatives is described for use in treating inflammation and inflammation-related disorders. Compounds of particular interest are defined by Formula I

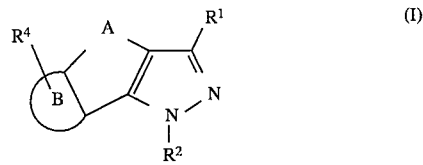

wherein A is $-(CH_2)_m-X-(CH_2)_n-$; wherein X is $S(O)_p$ or O; wherein m is 0 or 1; wherein n is 0 or 1; wherein p is 0 or 1; wherein B is selected from phenyl and five and six membered heteroaryl; wherein $R^1$ is selected from lower haloalkyl, cyano, formyl, lower alkoxycarbonyl, lower alkoxy, lower N-alkylaminocarbonyl, N-phenylaminocarbonyl, lower N,N-dialkylaminocarbonyl and lower N-alkyl-N-phenylaminocarbonyl; wherein $R^2$ is phenyl substituted at a substitutable position with a radical selected from lower alkylsulfonyl and sulfamyl; and wherein $R^4$ is one or more radicals selected from hydrido, halo, lower alkylthio, lower alkylsulfinyl, lower alkyl, cyano, carboxyl, lower alkoxycarbonyl, aminocarbonyl, lower haloalkyl, hydroxyl, lower alkoxy, amino, lower N-alkylamino, lower N,N-dialkylamino, lower hydroxyalkyl and lower haloalkoxy; or a pharmaceutically-acceptable salt thereof.

29 Claims, No Drawings

HETEROARYLPYRANOPYRAZOLYL DERIVATIVES FOR THE TREATMENT OF INFLAMMATION

This is a divisional application of U.S. application 08/309,291, filed Sep. 20, 1994.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase II (COX II)" or "prostaglandin G/H synthase II") provides a viable target of inhibition which more effectively reduces inflammation and produces fewer and less drastic side effects.

The novel compounds described herein are such safe and also effective antiinflammatory agents. The invention compounds are found to show usefulness in vivo as antiinflammatory agents with minimal side effects. The compounds described herein preferably selectively inhibit cyclooxygenase II over cyclooxygenase I.

Substituted pyrazoles having antiinflammatory activity are described in copending applications 08/160,594 and 08/160,553.

U.S. Pat. No. 3,940,418 to R. Hamilton describes tricyclic 4,5-dihydrobenz[g]indazole-3-carboxylic acids as antiinflammatory agents.

U.S. Pat. No. 4,803,193 to Kanda et al, describes spiro [3-alkyl-1-aryl[1]benzopyrano[4,3-c]pyrazole-4(1H),9'-[9H]fluorenes as heat sensitive recording matertials.

V. Colota et al (*J.Med.Chem.*, 33, 2646 (1991)) describe tricyclic heteroaramatic systems, including 1-aryl-pyrazolo [4,5-c]quinolin-4-ones, 1-aryl-pyrazolo[4,5-c][1,8]naphthyridin-4-ones and 1-aryl-[1]benzopyrano [3,4-d]pyrazol-4-ones for CNS aplications. F. Melani et al [*J.Med.Chem.*, 29, 291 (1986) also describe 1-phenyl-pyrazolo [4,5-c]quinolines for CNS applications.

U.S. Pat. Nos. 4,816,467 and 5,206,258 to Doria et al describe (2-cyano-3-(1,4-dihydro)-1-phenyl-[1]benzothiopyrano [4,3-c]pyrazol-3-yl)-3-oxo-propanamides as immunomodulators. G. Doria et al (*Farmaco*, 46, 843 (1991)) also describe the immunomodulating activity of pyrazolylpropanamides, and specifically ethyl [1-(4-fluorophenyl)-1,4-dihydro-[1]benzothiopyrano[4,3-c]pyrazole]-3-carboxylate. British patent 2,227,741 describes related benzopyrano[4,3-c]pyrazoles and benzothiopyrano[4,3-c]pyrazoles. European application No. 347,773 similarly describes such fused pyrazole compounds, and specifically α-cyano-N,1-bis(4-fluorophenyl)-β-oxo-1H-[1]benzothieno[3,2-c]pyrazole-3-propanamide. U.S. Pat. No. 5,260,328 to Doria et al describes 2-cyano-3-(1,4-dihydro)-1-phenyl-[1]benzothiopyrano[4,3-c]pyrazol-3-yl)-3-oxo-propanamides for the treatment of rheumatoid arthritis.

U.S. Pat. No. 4,678,499 to Pasteris et al describes 1-aryl-indenopyrazol-4-one-5-sulfonamides as having herbicidal activity. Specifically, 1-phenylindenopyrazol- 4-one-5-sulfonamide and 1,4-dihydro-N-[[(4-methoxy-6-methyl-2-pyrimidinyl)amino]carbonyl]-3-methyl- 1-[4-(methylsulfonyl)phenyl]-4-oxo-indeno[1,2-c]pyrazole-5-sulfonamide are described.

However, the benzopyranopyrazolyl derivatives of the present invention have not been previously described.

DESCRIPTION OF THE INVENTION

A class of compounds useful in treating inflammation-related disorders is defined by Formula I:

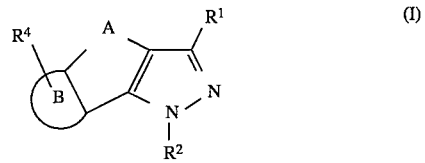

wherein A is —$(CH_2)_m$—X—$(CH_2)_n$—;

wherein X is selected from $S(O)_p$, O and $NR^3$;

wherein m is 0 to 3, inclusive;

wherein n is 0 to 3, inclusive;

wherein p is 0 to 2, inclusive;

wherein B is selected from aryl and heteroaryl;

wherein $R^1$ is selected from hydrido, halo, haloalkyl, cyano, nitro, formyl, alkoxycarbonyl, carboxyl, carboxyalkyl, alkoxycarbonylalkyl, amidino, cyanoamidino, aminocarbonyl, alkoxy, alkoxyalkyl, aminocarbonylalkyl, N-alkylaminocarbonyl, N-arylaminocarbonyl, N,N-dialkylaminocarbonyl, N-alkyl-N-arylaminocarbonyl, alkylcarbonyl, alkylcarbonylalkyl, hydroxyalkyl, alkylthio, alkylsulfinyl, alkylsulfonyl, alkylthioalkyl, alkylsulfinylalkyl, alkylsulfonylalkyl, N-alkylsulfamyl, N-arylsulfamyl, arylsulfonyl, N,N-dialkylsulfamyl, N-alkyl-N-arylsulfamyl and heterocyclic;

wherein $R^2$ is selected from aryl and heteroaryl, wherein $R^2$ is optionally substituted at a substitutable position with one or more radicals selected from alkylsulfonyl, sulfamyl, halo, alkyl, alkoxy, hydroxyl and haloalkyl;

wherein $R^3$ is selected from hydrido and alkyl; and wherein $R^4$ is one or more radicals selected from hydrido, halo, alkylthio, alkylsulfinyl, alkyl, alkylsulfonyl, cyano, carboxyl, alkoxycarbonyl, amido, N-alkylaminocarbonyl, N-arylaminocarbonyl, N,N-dialkylaminocarbonyl, N-alkyl-N-arylaminocarbonyl, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino;

provided either $R^4$ is sulfamyl or alkylsulfonyl, or $R^2$ is substituted with sulfamyl or alkylsulfonyl;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as antiinflammatory agents, such as for the treatment of arthritis, with the additional benefit of having significantly less harmful side effects.

The present invention preferably includes compounds which selectively inhibit cyclooxygenase II over cyclooxygenase I. Preferably, the compounds have a cyclooxygenase II $IC_{50}$ of less than about 0.2 μM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 1 μM, and more preferably of greater than 10 μM. Such preferred selectivity may indicate an ability to reduce the incidence of common NSAID-induced side effects.

A preferred class of compounds consists of those compounds of Formula I wherein A is —$(CH_2)_m$—X—$(CH_2)_n$—;

wherein X is selected from $S(O)_p$, O and $NR^3$;

wherein m is 0 to 3, inclusive;

wherein n is 0 to 3, inclusive;

wherein p is 0 to 2, inclusive;

wherein B is selected from phenyl, naphthyl and five and six membered heteroaryl;

wherein $R^1$ is selected from halo, lower haloalkyl, cyano, nitro, formyl, lower alkoxycarbonyl, lower carboxyalkyl, lower alkoxycarbonylalkyl, amidino, cyanoamidino, lower alkoxy, lower alkoxyalkyl, aminocarbonyl, lower aminocarbonylalkyl, lower N-alkylaminocarbonyl, N-phenylaminocarbonyl, lower N,N-dialkylaminocarbonyl, lower N-alkyl-N-phenylaminocarbonyl, lower alkylcarbonyl, lower alkylcarbonylalkyl, lower hydroxyalkyl, lower alkylthio, lower alkylsulfinyl, lower alkylsulfonyl, lower alkylthioalkyl, lower alkylsulfinylalkyl, lower alkylsulfonylalkyl, lower N-alkylsulfamyl, N-phenylsulfamyl, phenylsulfonyl, lower N,N-dialkylsulfamyl, lower N-alkyl-N-phenylsulfamyl and five-seven membered heterocyclic;

wherein $R^2$ is selected from phenyl and five or six membered heteroaryl, wherein $R^2$ is optionally substituted at a substitutable position with one or more radicals selected from lower alkylsulfonyl, sulfamyl, halo, lower alkyl, lower alkoxy, hydroxyl and lower haloalkyl;

wherein $R^3$ is selected from hydrido and lower alkyl; and wherein $R^4$ is one or more radicals selected from hydrido, halo, lower alkylthio, lower alkylsulfinyl, lower alkyl, lower alkylsulfonyl, cyano, carboxyl, lower alkoxycarbonyl, aminocarbonyl, lower N-alkylaminocarbonyl, N-phenylaminocarbonyl, lower N,N-dialkylaminocarbonyl, lower N-alkyl-N-phenylaminocarbonyl, lower haloalkyl, hydroxyl, lower alkoxy, lower hydroxyalkyl, lower haloalkoxy, sulfamyl, lower N-alkylsulfamyl, amino, lower N-alkylamino, lower N,N-dialkylamino, five-seven membered heterocyclic, nitro and acylamino;

or a pharmaceutically-acceptable salt thereof.

A more preferred class of compounds consists of those compounds of Formula I wherein A is —$(CH_2)_m$—X—$(CH_2)_n$—; wherein X is $S(O)_p$ or O; wherein m is 0, 1 or 2; wherein n is 0, 1 or 2; wherein p is 0, 1 or 2; wherein B is selected from phenyl and five and six membered heteroaryl; wherein $R^1$ is selected from halo, lower haloalkyl, cyano, formyl, lower alkoxycarbonyl, aminocarbonyl, lower alkoxycarbonylalkyl, lower alkoxy, lower alkoxyalkyl, lower aminocarbonylalkyl, lower N-alkylaminocarbonyl, N-phenylaminocarbonyl, lower N,N-dialkylaminocarbonyl, lower N-alkyl-N-phenylaminocarbonyl and lower hydroxyalkyl; wherein $R^2$ is phenyl substituted at a substitutable position with a radical selected from lower alkylsulfonyl and sulfamyl; and wherein $R^4$ is one or more radicals selected from hydrido, halo, lower alkylthio, lower alkylsulfinyl, lower alkyl, lower alkylsulfonyl, cyano, carboxyl, lower alkoxycarbonyl, aminocarbonyl, lower N-alkylaminocarbonyl, lower N,N-dialkylaminocarbonyl, lower N-alkyl-N-phenylaminocarbonyl, lower haloalkyl, hydroxyl, lower alkoxy, lower hydroxyalkyl, amino, lower N-alkylamino, lower N,N-dialkylamino, lower haloalkoxy and nitro; or a pharmaceutically-acceptable salt thereof.

An even more preferred class of compounds consists of those compounds of Formula I wherein A is —$(CH_2)_m$—X—$(CH_2)_n$—; wherein X is $S(O)_p$ or O; wherein m is 0 or 1; wherein n is 0 or 1; wherein p is 0 or 1; wherein B is selected from phenyl and five and six membered heteroaryl; wherein $R^1$ is selected from lower haloalkyl, cyano, formyl, lower alkoxycarbonyl, lower alkoxy, lower N-alkylaminocarbonyl, N-phenylaminocarbonyl, lower N,N-dialkylaminocarbonyl and lower N-alkyl-N-phenylaminocarbonyl; wherein $R^2$ is phenyl substituted at a substitutable position with a radical selected from lower alkylsulfonyl and sulfamyl; and wherein $R^4$ is one or more radicals selected from hydrido, halo, lower alkylthio, lower alkylsulfinyl, lower alkyl, cyano, carboxyl, lower alkoxycarbonyl, aminocarbonyl, lower haloalkyl, hydroxyl, lower alkoxy, amino, lower N-alkylamino, lower N,N-dialkylamino, lower hydroxyalkyl and lower haloalkoxy; or a pharmaceutically-acceptable salt thereof.

A class of compounds of particular interest consists of those compounds of Formula I wherein A is —$(CH_2)_m$—X—$(CH_2)_n$—; wherein X is $S(O)_p$ or O; wherein m is 0 or 1; wherein n is 0 or 1; wherein p is 0 or 1; wherein B is selected from phenyl, thienyl, pyridyl, furyl, oxazolyl, thiazolyl, imidazolyl, pyrazolyl, isoxazolyl, isothiazolyl, triazolyl, pyridazinyl, pyrimidinyl, pyrazinyl, triazinyl, thiaimidazolyl, oxoimidazolyl, azaoxazolyl, azathiazolyl and pyrrolyl;

wherein $R^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, formyl, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, methoxy, ethoxy, propoxy, n-butoxy, N-methylaminocarbonyl, N-phenylaminocarbonyl, N,N-dimethylaminocarbonyl, N-methyl-N-phenylaminocarbonyl and methylcarbonyl;

wherein $R^2$ is phenyl substituted at a substitutable position with a radical selected from methylsulfonyl and sulfamyl; and wherein $R^4$ is optionally substituted with one or more radicals selected from hydrido, fluoro, chloro, bromo, methylthio, ethylthio, isopropylthio, tert-butylthio, isobutylthio, hexylthio, methylsulfinyl, ethylsulfinyl, isopropylsulfinyl, tert-butylsulfinyl, isobutylsulfinyl, hexylsulfinyl, methyl, ethyl, isopropyl, tert-butyl, isobutyl, hexyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl and trifluoromethoxy; or a pharmaceutically-acceptable salt thereof.

The preferred compounds of Formula I can be represented by Formulas Ia–Ih as follows:

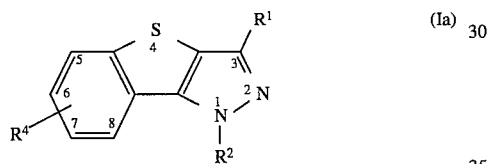
(Ia)

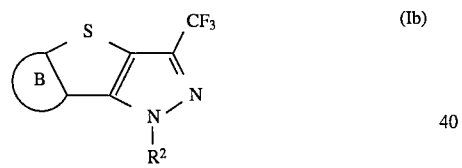
(Ib)

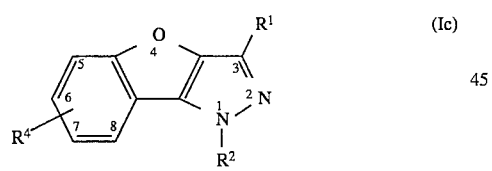
(Ic)

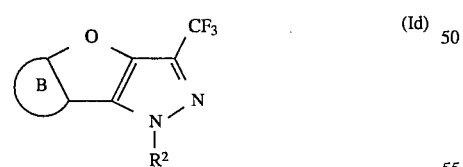
(Id)

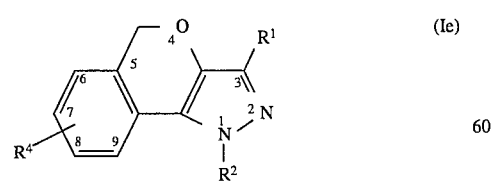
(Ie)

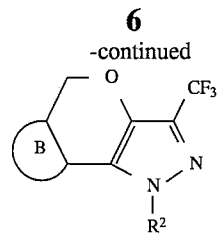
(If)

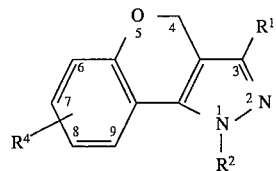
(Ig)

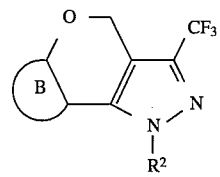
(Ih)

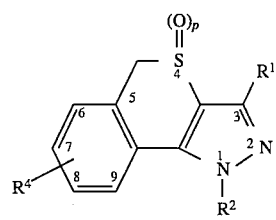
(Ii)

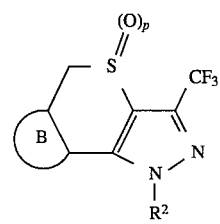
(Ij)

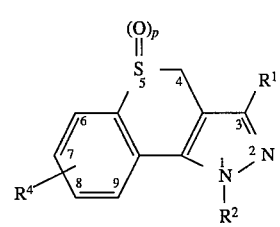
(Ik)

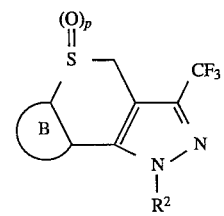
(Il)

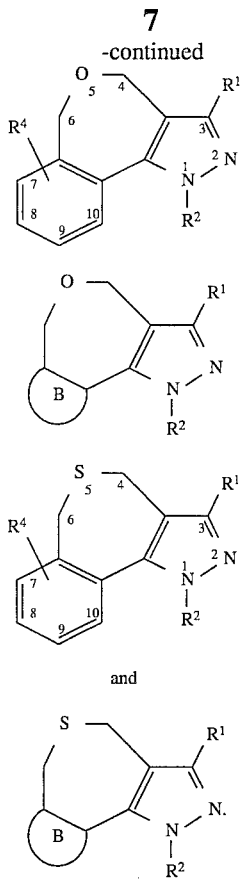

A family of specific compounds of particular interest within Formula I consists of compounds and pharmaceutically-acceptable salts thereof as shown in the following Tables:

TABLE I

| | General Structure 1a | |
|---|---|---|
| R¹ | R² | R⁴ |
| —CF₃ | C₆H₅SO₂CH₃ | H |
| —CF₂H | C₆H₅SO₂CH₃ | H |
| —CF₂Cl | C₆H₅SO₂CH₃ | H |
| —CF₂CF₃ | C₆H₅SO₂CH₃ | H |
| —CO₂H | C₆H₅SO₂CH₃ | H |
| —CO₂CH₃ | C₆H₅SO₂CH₃ | H |
| —CO₂C₂H₅ | C₆H₅SO₂CH₃ | H |
| —CONH₂ | C₆H₅SO₂CH₃ | H |
| —CONHCH₃ | C₆H₅SO₂CH₃ | H |
| —CONH(C₆H₃) | C₆H₅SO₂CH₃ | H |
| —CON(CH₃)₂ | C₆H₅SO₂CH₃ | H |
| —CON(C₂H₅)₂ | C₆H₅SO₂CH₃ | H |
| —CON(CH₃)(C₂H₅) | C₆H₅SO₂CH₃ | H |
| —CON(CH₃)(C₆H₅) | C₆H₅SO₂CH₃ | H |
| —C(O)—N(pyrrolidinyl) | C₆H₅SO₂CH₃ | H |
| —C(O)—N(piperidinyl) | C₆H₅SO₂CH₃ | H |
| —CN | C₆H₅SO₂CH₃ | H |
| —CH₂OH | C₆H₅SO₂CH₃ | H |
| —CH₂OCH₃ | C₆H₅SO₂CH₃ | H |
| —CH₂OC₂H₅ | C₆H₅SO₂CH₃ | H |

TABLE I-continued

| | General Structure 1a | |
|---|---|---|
| R¹ | R² | R⁴ |
| —CH₂OC₆H₅ | C₆H₅SO₂CH₃ | H |
| —CH₂SCH₃ | C₆H₅SO₂CH₃ | H |
| —CH₂SC₂H₅ | C₆H₅SO₂CH₃ | H |
| —CH₂SC₆H₅ | C₆H₅SO₂CH₃ | H |
| —CH₂SOCH₃ | C₆H₅SO₂CH₃ | H |
| —CH₂SOC₂H₅ | C₆H₅SO₂CH₃ | H |
| —CH₂SOC₆H₅ | C₆H₅SO₂CH₃ | H |
| —CH₂SO₂CH₃ | C₆H₅SO₂CH₃ | H |
| —CH₂SO₂C₂H₅ | C₆H₅SO₂CH₃ | H |
| —CH₂SO₂C₆H₅ | C₆H₅SO₂CH₃ | H |
| —CF₃ | C₆H₅SO₂CH₃ | 5-F |
| —CF₃ | C₆H₅SO₂CH₃ | 7-F |
| —CF₃ | C₆H₅SO₂CH₃ | 6-F |
| —CF₃ | C₆H₅SO₂CH₃ | 7-Cl |
| —CF₃ | C₆H₅SO₂CH₃ | 6-Cl |
| —CF₃ | C₆H₅SO₂CH₃ | 6,7-(OCH₂O)— |
| —CF₃ | C₆H₅SO₂CH₃ | 6-N(CH₃)₂ |
| —CF₃ | C₆H₅SO₂CH₃ | 6-OCH₃ |
| —CF₃ | C₆H₅SO₂CH₃ | 5-F, 6-OCH₃ |
| —CF₃ | C₆H₅SO₂CH₃ | 5-Cl, 6-OCH₃ |
| —CF₃ | C₆H₅SO₂CH₃ | 6-Cl, 5-F |
| —CF₃ | C₆H₅SO₂CH₃ | 6-CH₃ |
| —CF₃ | C₆H₅SO₂CH₃ | 5-F, 6-CH₃ |
| —CF₃ | C₆H₅SO₂CH₃ | 5,6-F |
| —CF₃ | C₆H₅SO₂CH₃ | 6-SCH₃ |
| —CF₃ | C₆H₅SO₂CH₃ | 5-F, 6-SCH₃ |
| —CF₃ | C₆H₅SO₂CH₃ | 6-SOCH₃ |
| —CF₃ | C₆H₅SO₂CH₃ | 5-F, 6-SOCH₃ |
| —CF₃ | C₆H₅SO₂CH₃ | 5-F, 6-CH₃ |
| —CF₃ | C₆H₅F | 6-SO₂CH₃ |
| —CF₃ | C₆H₅Cl | 6-SO₂CH₃ |
| —CF₃ | C₆H₅OCH₃ | 6-SO₂CH₃ |
| —CF₃ | C₆H₅CH₃ | 6-SO₂CH₃ |
| —CF₃ | C₆H₅SOCH₃ | 6-SO₂CH₃ |
| —CF₃ | C₆H₅SO₂NH₂ | H |
| —CF₂H | C₆H₅SO₂NH₂ | H |
| —CF₂Cl | C₆H₅SO₂NH₂ | H |
| —CF₂CF₃ | C₆H₅SO₂NH₂ | H |
| —CO₂H | C₆H₅SO₂NH₂ | H |
| —CO₂CH₃ | C₆H₅SO₂NH₂ | H |
| —CO₂C₂H₅ | C₆H₅SO₂NH₂ | H |
| —CONH₂ | C₆H₅SO₂NH₂ | H |
| —CONHCH₃ | C₆H₅SO₂NH₂ | H |
| —CONH(C₆H₃) | C₆H₅SO₂NH₂ | H |
| —CON(CH₃)₂ | C₆H₅SO₂NH₂ | H |
| —CON(C₂H₅)₂ | C₆H₅SO₂NH₂ | H |
| —CON(CH₃)(C₂H₅) | C₆H₅SO₂NH₂ | H |
| —CON(CH₃)(C₆H₅) | C₆H₅SO₂NH₂ | H |
| —C(O)—N(pyrrolidinyl) | C₆H₅SO₂NH₂ | H |
| —C(O)—N(piperidinyl) | C₆H₅SO₂NH₂ | H |
| —CN | C₆H₅SO₂NH₂ | H |
| —CH₂OH | C₆H₅SO₂NH₂ | H |
| —CH₂OCH₃ | C₆H₅SO₂NH₂ | H |
| —CH₂OC₂H₅ | C₆H₅SO₂NH₂ | H |
| —CH₂OC₆H₅ | C₆H₅SO₂NH₂ | H |
| —CH₂SCH₃ | C₆H₅SO₂NH₂ | H |
| —CH₂SC₂H₅ | C₆H₅SO₂NH₂ | H |
| —CH₂SC₆H₅ | C₆H₅SO₂NH₂ | H |
| —CH₂SOCH₃ | C₆H₅SO₂NH₂ | H |
| —CH₂SOC₆H₅ | C₆H₅SO₂NH₂ | H |
| —CH₂SO₂CH₃ | C₆H₅SO₂NH₂ | H |
| —CH₂SO₂C₂H₅ | C₆H₅SO₂NH₂ | H |
| —CH₂SO₂C₆H₅ | C₆H₅SO₂NH₂ | H |
| —CF₃ | C₆H₅SO₂NH₂ | 5-F |
| —CF₃ | C₆H₅SO₂NH₂ | 7-F |

TABLE I-continued

General Structure Ia

| R¹ | R² | R⁴ |
|---|---|---|
| —CF₃ | C₆H₅SO₂NH₂ | 6-F |
| —CF₃ | C₆H₅SO₂NH₂ | 7-Cl |
| —CF₃ | C₆H₅SO₂NH₂ | 6-Cl |
| —CF₃ | C₆H₅SO₂NH₂ | 6,7-(OCH₂O)— |
| —CF₃ | C₆H₅SO₂NH₂ | 6-N(CH₃)₂ |
| —CF₃ | C₆H₅SO₂NH₂ | 6-OCH₃ |
| —CF₃ | C₆H₅SO₂NH₂ | 5-F, 6-OCH₃ |
| —CF₃ | C₆H₅SO₂NH₂ | 5-Cl, 6-OCH₃ |
| —CF₃ | C₆H₅SO₂NH₂ | 6-Cl, 5-F |
| —CF₃ | C₆H₅SO₂NH₂ | 6-CH₃ |
| —CF₃ | C₆H₅SO₂NH₂ | 5-F, 6-CH₃ |
| —CF₃ | C₆H₅SO₂NH₂ | 5,6-F |
| —CF₃ | C₆H₅SO₂NH₂ | 6-SCH₃ |
| —CF₃ | C₆H₅SO₂NH₂ | 5-F, 6-SCH₃ |
| —CF₃ | C₆H₅SO₂NH₂ | 6-SOCH₃ |
| —CF₃ | C₆H₅SO₂NH₂ | 5-F, 6-SOCH₃ |
| —CF₃ | C₆H₅SO₂NH₂ | 5-F, 6-CH₃ |
| —CF₃ | C₆H₅F | 6-SO₂NH₂ |
| —CF₃ | C₆H₅Cl | 6-SO₂NH₂ |
| —CF₃ | C₆H₅OCH₃ | 6-SO₂NH₂ |
| —CF₃ | C₆H₅CH₃ | 6-SO₂NH₂ |
| —CF₃ | C₆H₅SOCH₃ | 6-SO₂NH₂ |
| —CF₃ | thienylSO₂NH₂ | 5-F, 6-OCH₃ |

TABLE II

General Structure Ib

| B | R² |
|---|---|
| Cl—[furan] | —C₆H₅SO₂CH₃ |
| Cl—[thiophene] | —C₆H₅SO₂CH₃ |
| Cl—[oxazole, N] | —C₆H₅SO₂CH₃ |
| Cl—[oxazole, N other position] | —C₆H₅SO₂CH₃ |
| Cl—[thiazole] | —C₆H₅SO₂CH₃ |
| Cl—[imidazole, NH] | —C₆H₅SO₂CH₃ |
| [pyrazole, NH] | —C₆H₅SO₂CH₃ |
| [isoxazole] | —C₆H₅SO₂CH₃ |
| [isothiazole] | —C₆H₅SO₂CH₃ |

TABLE II-continued

General Structure Ib

| B | R² |
|---|---|
| Cl—[pyrrole, NH] | —C₆H₅SO₂CH₃ |
| Cl—[furan] | —C₆H₅SO₂NH₂ |
| Cl—[thiophene] | —C₆H₅SO₂NH₂ |
| Cl—[oxazole] | —C₆H₅SO₂NH₂ |
| Cl—[thiazole] | —C₆H₅SO₂NH₂ |
| Cl—[imidazole, NH] | —C₆H₅SO₂NH₂ |
| [pyrazole, NH] | —C₆H₅SO₂NH₂ |
| [isoxazole] | —C₆H₅SO₂NH₂ |
| [isothiazole] | —C₆H₅SO₂NH₂ |
| Cl—[pyrrole, NH] | —C₆H₅SO₂NH₂ |
| Cl—[pyrrole, NH] | —C₆H₅SO₂NH₂ |

TABLE III

General Structure Ic

| R¹ | R² | R⁴ |
|---|---|---|
| —CF₃ | C₆H₅SO₂CH₃ | H |
| —CF₂H | C₆H₅SO₂CH₃ | H |
| —CF₂Cl | C₆H₅SO₂CH₃ | H |
| —CF₂CF₃ | C₆H₅SO₂CH₃ | H |
| —CO₂H | C₆H₅SO₂CH₃ | H |
| —CO₂CH₃ | C₆H₅SO₂CH₃ | H |
| —CO₂C₂H₅ | C₆H₅SO₂CH₃ | H |
| —CONH₂ | C₆H₅SO₂CH₃ | H |
| —CONHCH₃ | C₆H₅SO₂CH₃ | H |
| —CONH(C₆H₃) | C₆H₅SO₂CH₃ | H |

TABLE III-continued

General Structure Ic

| R¹ | R² | R⁴ |
|---|---|---|
| —CON(CH₃)₂ | C₆H₅SO₂CH₃ | H |
| —CON(C₂H₅)₂ | C₆H₅SO₂CH₃ | H |
| —CON(CH₃)(C₂H₅) | C₆H₅SO₂CH₃ | H |
| —CON(CH₃)(C₆H₅) | C₆H₅SO₂CH₃ | H |
| —C(=O)N-pyrrolidinyl | C₆H₅SO₂CH₃ | H |
| —C(=O)N-piperidinyl | C₆H₅SO₂CH₃ | H |
| —CN | C₆H₅SO₂CH₃ | H |
| —CH₂OH | C₆H₅SO₂CH₃ | H |
| —CH₂OCH₃ | C₆H₅SO₂CH₃ | H |
| —CH₂OC₂H₅ | C₆H₅SO₂CH₃ | H |
| —CH₂OC₆H₅ | C₆H₅SO₂CH₃ | H |
| —CH₂SCH₃ | C₆H₅SO₂CH₃ | H |
| —CH₂SC₂H₅ | C₆H₅SO₂CH₃ | H |
| —CH₂SC₆H₅ | C₆H₅SO₂CH₃ | H |
| —CH₂SOCH₃ | C₆H₅SO₂CH₃ | H |
| —CH₂SOC₂H₅ | C₆H₅SO₂CH₃ | H |
| —CH₂SOC₆H₅ | C₆H₅SO₂CH₃ | H |
| —CH₂SO₂CH₃ | C₆H₅SO₂CH₃ | H |
| —CH₂SO₂C₂H₅ | C₆H₅SO₂CH₃ | H |
| —CH₂SO₂C₆H₅ | C₆H₅SO₂CH₃ | H |
| —CF₃ | C₆H₅SO₂CH₃ | 5-F |
| —CF₃ | C₆H₅SO₂CH₃ | 7-F |
| —CF₃ | C₆H₅SO₂CH₃ | 6-F |
| —CF₃ | C₆H₅SO₂CH₃ | 7-Cl |
| —CF₃ | C₆H₅SO₂CH₃ | 6-Cl |
| —CF₃ | C₆H₅SO₂CH₃ | 6,7-(OCH₂O)— |
| —CF₃ | C₆H₅SO₂CH₃ | 6-N(CH₃)₂ |
| —CF₃ | C₆H₅SO₂CH₃ | 6-OCH₃ |
| —CF₃ | C₆H₅SO₂CH₃ | 5-F, 6-OCH₃ |
| —CF₃ | C₆H₅SO₂CH₃ | 5-Cl, 6-OCH₃ |
| —CF₃ | C₆H₅SO₂CH₃ | 6-Cl, 5-F |
| —CF₃ | C₆H₅SO₂CH₃ | 6-CH₃ |
| —CF₃ | C₆H₅SO₂CH₃ | 5-F, 6-CH₃ |
| —CF₃ | C₆H₅SO₂CH₃ | 5,6-F |
| —CF₃ | C₆H₅SO₂CH₃ | 6-SCH₃ |
| —CF₃ | C₆H₅SO₂CH₃ | 5-F, 6-SCH₃ |
| —CF₃ | C₆H₅SO₂CH₃ | 6-SOCH₃ |
| —CF₃ | C₆H₅SO₂CH₃ | 5-F, 6-SOCH₃ |
| —CF₃ | C₆H₅SO₂CH₃ | 5-F, 6-CH₃ |
| —CF₃ | C₆H₅F | 6-SO₂CH₃ |
| —CF₃ | C₆H₅Cl | 6-SO₂CH₃ |
| —CF₃ | C₆H₅OCH₃ | 6-SO₂CH₃ |
| —CF₃ | C₆H₅CH₃ | 6-SO₂CH₃ |
| —CF₃ | C₆H₅SOCH₃ | 6-SO₂CH₃ |
| —CF₃ | C₆H₅SO₂NH₂ | H |
| —CF₂H | C₆H₅SO₂NH₂ | H |
| —CF₂Cl | C₆H₅SO₂NH₂ | H |
| —CF₂CF₃ | C₆H₅SO₂NH₂ | H |
| —CO₂H | C₆H₅SO₂NH₂ | H |
| —CO₂CH₃ | C₆H₅SO₂NH₂ | H |
| —CO₂C₂H₅ | C₆H₅SO₂NH₂ | H |
| —CONH₂ | C₆H₅SO₂NH₂ | H |
| —CONHCH₃ | C₆H₅SO₂NH₂ | H |
| —CONH(C₆H₅) | C₆H₅SO₂NH₂ | H |
| —CON(CH₃)₂ | C₆H₅SO₂NH₂ | H |
| —CON(C₂H₅)₂ | C₆H₅SO₂NH₂ | H |
| —CON(CH₃)(C₂H₅) | C₆H₅SO₂NH₂ | H |
| —CON(CH₃)(C₆H₅) | C₆H₅SO₂NH₂ | H |
| —C(=O)N-pyrrolidinyl | C₆H₅SO₂NH₂ | H |
| —C(=O)N-piperidinyl | C₆H₅SO₂NH₂ | H |
| —CN | C₆H₅SO₂NH₂ | H |
| —CH₂OH | C₆H₅SO₂NH₂ | H |
| —CH₂OCH₃ | C₆H₅SO₂NH₂ | H |
| —CH₂OC₂H₅ | C₆H₅SO₂NH₂ | H |
| —CH₂OC₆H₅ | C₆H₅SO₂NH₂ | H |
| —CH₂SCH₃ | C₆H₅SO₂NH₂ | H |
| —CH₂SC₂H₅ | C₆H₅SO₂NH₂ | H |
| —CH₂SC₆H₅ | C₆H₅SO₂NH₂ | H |
| —CH₂SOC₆H₅ | C₆H₅SO₂NH₂ | H |
| —CH₂SO₂CH₃ | C₆H₅SO₂NH₂ | H |
| —CH₂SO₂C₂H₅ | C₆H₅SO₂NH₂ | H |
| —CH₂SO₂C₆H₅ | C₆H₅SO₂NH₂ | H |
| —CF₃ | C₆H₅SO₂NH₂ | 5-F |
| —CF₃ | C₆H₅SO₂NH₂ | 7-F |
| —CF₃ | C₆H₅SO₂NH₂ | 6-F |
| —CF₃ | C₆H₅SO₂NH₂ | 7-Cl |
| —CF₃ | C₆H₅SO₂NH₂ | 6-Cl |
| —CF₃ | C₆H₅SO₂NH₂ | 6,7-(OCH₂O)— |
| —CF₃ | C₆H₅SO₂NH₂ | 6-N(CH₃)₂ |
| —CF₃ | C₆H₅SO₂NH₂ | 6-OCH₃ |
| —CF₃ | C₆H₅SO₂NH₂ | 5-F, 6-OCH₃ |
| —CF₃ | C₆H₅SO₂NH₂ | 5-Cl, 6-OCH₃ |
| —CF₃ | C₆H₅SO₂NH₂ | 6-Cl, 5-F |
| —CF₃ | C₆H₅SO₂NH₂ | 6-CH₃ |
| —CF₃ | C₆H₅SO₂NH₂ | 5-F, 6-CH₃ |
| —CF₃ | C₆H₅SO₂NH₂ | 5,6-F |
| —CF₃ | C₆H₅SO₂NH₂ | 6-SCH₃ |
| —CF₃ | C₆H₅SO₂NH₂ | 5-F, 6-SCH₃ |
| —CF₃ | C₆H₅SO₂NH₂ | 6-SOCH₃ |
| —CF₃ | C₆H₅SO₂NH₂ | 5-F, 6-SOCH₃ |
| —CF₃ | C₆H₅SO₂NH₂ | 5-F, 6-CH₃ |
| —CF₃ | C₆H₅F | 6-SO₂NH₂ |
| —CF₃ | C₆H₅Cl | 6-SO₂NH₂ |
| —CF₃ | C₆H₅OCH₃ | 6-SO₂NH₂ |
| —CF₃ | C₆H₅CH₃ | 6-SO₂NH₂ |
| —CF₃ | C₆H₅SOCH₃ | 6-SO₂NH₂ |
| —CF₃ | thienylSO₂NH₂ | 5-F, 6-OCH₃ |

TABLE IV

General Structure Id

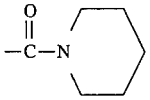

| B | R² |
|---|---|
| 5-chloro-2-furyl | —C₆H₅SO₂CH₃ |
| 5-chloro-2-thienyl | —C₆H₅SO₂CH₃ |
| 2-chloro-5-oxazolyl | —C₆H₅SO₂CH₃ |
| 2-chloro-5-isoxazolyl | —C₆H₅SO₂CH₃ |
| 2-chloro-5-thiazolyl | —C₆H₅SO₂CH₃ |

TABLE IV-continued

General Structure Id

| B | R² |
|---|---|
| 2-Cl, pyrazole (N-H) | $-C_6H_5SO_2CH_3$ |
| pyrazole (N-N-H) | $-C_6H_5SO_2CH_3$ |
| isoxazole (N-O) | $-C_6H_5SO_2CH_3$ |
| isothiazole (N-S) | $-C_6H_5SO_2CH_3$ |
| 5-Cl-pyrrole (N-H) | $-C_6H_5SO_2CH_3$ |
| 5-Cl-furan (O) | $-C_6H_5SO_2NH_2$ |
| 5-Cl-thiophene (S) | $-C_6H_5SO_2NH_2$ |
| 5-Cl-oxazole (O-N) | $-C_6H_5SO_2NH_2$ |
| 2-Cl-thiazole (N-S) | $-C_6H_5SO_2NH_2$ |
| 2-Cl-imidazole (N-N-H) | $-C_6H_5SO_2NH_2$ |
| pyrazole (N-N-H) | $-C_6H_5SO_2NH_2$ |
| isoxazole (N-O) | $-C_6H_5SO_2NH_2$ |
| isothiazole (N-S) | $-C_6H_5SO_2NH_2$ |
| 5-Cl-pyrrole (N-H) | $-C_6H_5SO_2NH_2$ |
| 5-Cl-pyrrole (N-H) | $-C_6H_5SO_2NH_2$ |

TABLE V

General Structure Ie

| R¹ | R² | R⁴ |
|---|---|---|
| $-CF_3$ | $-C_6H_5SO_2CH_3$ | H |
| $-CF_2H$ | $-C_6H_5SO_2CH_3$ | H |
| $-CF_2Cl$ | $-C_6H_5SO_2CH_3$ | H |
| $-CF_2CF_3$ | $-C_6H_5SO_2CH_3$ | H |
| $-CO_2H$ | $-C_6H_5SO_2CH_3$ | H |
| $-CO_2CH_3$ | $-C_6H_5SO_2CH_3$ | H |
| $-CO_2C_2H_5$ | $-C_6H_5SO_2CH_3$ | H |
| $-CONH_2$ | $-C_6H_5SO_2CH_3$ | H |
| $-CONHCH_3$ | $-C_6H_5SO_2CH_3$ | H |
| $-CONH(C_6H_5)$ | $-C_6H_5SO_2CH_3$ | H |
| $-CON(CH_3)_2$ | $-C_6H_5SO_2CH_3$ | H |
| $-CON(C_2H_5)_2$ | $-C_6H_5SO_2CH_3$ | H |
| $-CON(CH_3)(C_2H_5)$ | $-C_6H_5SO_2CH_3$ | H |
| $-CON(CH_3)(C_6H_5)$ | $-C_6H_5SO_2CH_3$ | H |
| $-C(O)N$-pyrrolidinyl | $-C_6H_5SO_2CH_3$ | H |
| $-C(O)N$-piperidinyl | $-C_6H_5SO_2CH_3$ | H |
| $-CN$ | $-C_6H_5SO_2CH_3$ | H |
| $-CH_2OH$ | $-C_6H_5SO_2CH_3$ | H |
| $-CH_2OCH_3$ | $-C_6H_5SO_2CH_3$ | H |
| $-CH_2OC_2H_5$ | $-C_6H_5SO_2CH_3$ | H |
| $-CH_2OC_6H_5$ | $-C_6H_5SO_2CH_3$ | H |
| $-CH_2SCH_3$ | $-C_6H_5SO_2CH_3$ | H |
| $-CH_2SC_2H_5$ | $-C_6H_5SO_2CH_3$ | H |
| $-CH_2SC_6H_5$ | $-C_6H_5SO_2CH_3$ | H |
| $-CH_2SOCH_3$ | $-C_6H_5SO_2CH_3$ | H |
| $-CH_2SOC_2H_5$ | $-C_6H_5SO_2CH_3$ | H |
| $-CH_2SOC_6H_5$ | $-C_6H_5SO_2CH_3$ | H |
| $-CH_2SO_2CH_3$ | $-C_6H_5SO_2CH_3$ | H |
| $-CH_2SO_2C_2H_5$ | $-C_6H_5SO_2CH_3$ | H |
| $-CH_2SO_2C_6H_5$ | $-C_6H_5SO_2CH_3$ | H |
| $-CF_3$ | $-C_6H_5SO_2CH_3$ | 6-F |
| $-CF_3$ | $-C_6H_5SO_2CH_3$ | 7-F |
| $-CF_3$ | $-C_6H_5SO_2CH_3$ | 8-F |
| $-CF_3$ | $-C_6H_5SO_2CH_3$ | 7-Cl |
| $-CF_3$ | $-C_6H_5SO_2CH_3$ | 8-Cl |
| $-CF_3$ | $-C_6H_5SO_2CH_3$ | 7,8-$(OCH_2O)-$ |
| $-CF_3$ | $-C_6H_5SO_2CH_3$ | 7-$N(CH_3)_2$ |
| $-CF_3$ | $-C_6H_5SO_2CH_3$ | 7-$OCH_3$ |
| $-CF_3$ | $-C_6H_5SO_2CH_3$ | 6-F, 7-$OCH_3$ |
| $-CF_3$ | $-C_6H_5SO_2CH_3$ | 6-Cl, 7-$OCH_3$ |
| $-CF_3$ | $-C_6H_5SO_2CH_3$ | 7-Cl, 6-F |
| $-CF_3$ | $-C_6H_5SO_2CH_3$ | 7-$CH_3$ |
| $-CF_3$ | $-C_6H_5SO_2CH_3$ | 6-F, 7-$CH_3$ |
| $-CF_3$ | $-C_6H_5SO_2CH_3$ | 6,7-F |
| $-CF_3$ | $-C_6H_5SO_2CH_3$ | 7-$SCH_3$ |
| $-CF_3$ | $-C_6H_5SO_2CH_3$ | 6-F, 7-$SCH_3$ |
| $-CF_3$ | $-C_6H_5SO_2CH_3$ | 7-$SOCH_3$ |
| $-CF_3$ | $-C_6H_5SO_2CH_3$ | 6-F, 7-$SOCH_3$ |
| $-CF_3$ | $-C_6H_5SO_2CH_3$ | 6-F, 7-$CH_3$ |
| $-CF_3$ | $-C_6H_5F$ | 7-$SO_2CH_3$ |
| $-CF_3$ | $-C_6H_5Cl$ | 7-$SO_2CH_3$ |
| $-CF_3$ | $-C_6H_5OCH_3$ | 7-$SO_2CH_3$ |

TABLE V-continued

General Structure Ic

| R¹ | R² | R⁴ |
|---|---|---|
| —CF₃ | —C₆H₅CH₃ | 7-SO₂CH₃ |
| —CF₃ | —C₆H₅SOCH₃ | 7-SO₂CH₃ |
| —CF₃ | —C₆H₅SO₂NH₂ | H |
| —CF₂H | —C₆H₅SO₂NH₂ | H |
| —CF₂Cl | —C₆H₅SO₂NH₂ | H |
| —CF₂CF₃ | —C₆H₅SO₂NH₂ | H |
| —CO₂H | —C₆H₅SO₂NH₂ | H |
| —CO₂CH₃ | —C₆H₅SO₂NH₂ | H |
| —CO₂C₂H₅ | —C₆H₅SO₂NH₂ | H |
| —CONH₂ | —C₆H₅SO₂NH₂ | H |
| —CONHCH₃ | —C₆H₅SO₂NH₂ | H |
| —CONH(C₆H₅) | —C₆H₅SO₂NH₂ | H |
| —CON(CH₃)₂ | —C₆H₅SO₂NH₂ | H |
| —CON(C₂H₅)₂ | —C₆H₅SO₂NH₂ | H |
| —CON(CH₃)(C₂H₅) | —C₆H₅SO₂NH₂ | H |
| —CON(CH₃)(C₆H₅) | —C₆H₅SO₂NH₂ | H |
| 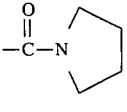 | —C₆H₅SO₂NH₂ | H |
| 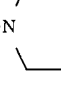 | —C₆H₅SO₂NH₂ | H |
| —CN | —C₆H₅SO₂NH₂ | H |
| —CH₂OH | —C₆H₅SO₂NH₂ | H |
| —CH₂OCH₃ | —C₆H₅SO₂NH₂ | H |
| —CH₂OC₂H₅ | —C₆H₅SO₂NH₂ | H |
| —CH₂OC₆H₅ | —C₆H₅SO₂NH₂ | H |
| —CH₂SCH₃ | —C₆H₅SO₂NH₂ | H |
| —CH₂SC₂H₅ | —C₆H₅SO₂NH₂ | H |
| —CH₂SC₆H₅ | —C₆H₅SO₂NH₂ | H |
| —CH₂SOCH₃ | —C₆H₅SO₂NH₂ | H |
| —CH₂SOC₂H₅ | —C₆H₅SO₂NH₂ | H |
| —CH₂SOC₆H₅ | —C₆H₅SO₂NH₂ | H |
| —CH₂SO₂CH₃ | —C₆H₅SO₂NH₂ | H |
| —CH₂SO₂C₂H₅ | —C₆H₅SO₂NH₂ | H |
| —CH₂SO₂C₆H₅ | —C₆H₅SO₂NH₂ | H |
| —CF₃ | —C₆H₅SO₂NH₂ | 6-F |
| —CF₃ | —C₆H₅SO₂NH₂ | 7-F |
| —CF₃ | —C₆H₅SO₂NH₂ | 8-F |
| —CF₃ | —C₆H₅SO₂NH₂ | 7-Cl |
| —CF₃ | —C₆H₅SO₂NH₂ | 8-Cl |
| —CF₃ | —C₆H₅SO₂NH₂ | 7,8-(OCH₂O)— |
| —CF₃ | —C₆H₅SO₂NH₂ | 7-N(CH₃)₂ |
| —CF₃ | —C₆H₅SO₂NH₂ | 7-OCH₃ |
| —CF₃ | —C₆H₅SO₂NH₂ | 6-F, 7-OCH₃ |
| —CF₃ | —C₆H₅SO₂NH₂ | 6-Cl, 7-OCH₃ |
| —CF₃ | —C₆H₅SO₂NH₂ | 7-Cl, 6-F |
| —CF₃ | —C₆H₅SO₂NH₂ | 7-CH₃ |
| —CF₃ | —C₆H₅SO₂NH₂ | 6-F, 7-CH₃ |
| —CF₃ | —C₆H₅SO₂NH₂ | 6,7-F |
| —CF₃ | —C₆H₅SO₂NH₂ | 7-SCH₃ |
| —CF₃ | —C₆H₅SO₂NH₂ | 6-F, 7-SCH₃ |
| —CF₃ | —C₆H₅SO₂NH₂ | 7-SOCH₃ |
| —CF₃ | —C₆H₅SO₂NH₂ | 6-F, 7-SOCH₃ |
| —CF₃ | —C₆H₅SO₂NH₂ | 6-F, 7-CH₃ |
| —CF₃ | —C₆H₅SO₂NH₂ | 6-F, 7-OCH₃ |
| —CF₃ | —C₆H₅F | 7-SO₂NH₂ |
| —CF₃ | —C₆H₅Cl | 7-SO₂NH₂ |
| —CF₃ | —C₆H₅OCH₃ | 7-SO₂NH₂ |
| —CF₃ | —C₆H₅CH₃ | 7-SO₂NH₂ |
| —CF₃ | —C₆H₅SOCH₃ | 7-SO₂NH₂ |

TABLE VI

General Structure If

| B | R² |
|---|---|
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |
|  | —C₆H₅SO₂CH₃ |

TABLE VI-continued

General Structure If

| B | R² |
|---|---|
| triazole (N=N, NH) | —C₆H₅SO₂CH₃ |
| thiadiazole (N=N, S) | —C₆H₅SO₂CH₃ |
| thiadiazole (N, S, N) | —C₆H₅SO₂CH₃ |
| oxadiazole (N, O, N) | —C₆H₅SO₂CH₃ |
| oxadiazole (N=N, O) | —C₆H₅SO₂CH₃ |
| Cl-pyrrole (NH) | —C₆H₅SO₂CH₃ |
| Cl-pyrrole (NH) | —C₆H₅SO₂CH₃ |
| oxadiazole (O, N, N) | —C₆H₅SO₂CH₃ |
| thiadiazole (S, N, N) | —C₆H₅SO₂CH₃ |
| Cl-furan (O) | —C₆H₅SO₂CH₃ |
| Cl-furan (O) | —C₆H₅SO₂CH₃ |
| Cl-thiophene (S) | —C₆H₅SO₂CH₃ |
| Cl-thiophene (S) | —C₆H₅SO₂CH₃ |
| Cl-oxazole (N, O) | —C₆H₅SO₂CH₃ |
| Cl-oxazole (N, O) | —C₆H₅SO₂CH₃ |

TABLE VI-continued

General Structure If

| B | R² |
|---|---|
| Cl-thiazole (S, N) | —C₆H₅SO₂CH₃ |
| Cl-thiazole (N, S) | —C₆H₅SO₂CH₃ |
| Cl-pyrazole (N, NH) | —C₆H₅SO₂CH₃ |
| pyrazole (N, NH) | —C₆H₅SO₂CH₃ |
| pyrazole (NH, N) | —C₆H₅SO₂CH₃ |
| isoxazole (N, O) | —C₆H₅SO₂CH₃ |
| isoxazole (N, O) | —C₆H₅SO₂CH₃ |
| isothiazole (N, S) | —C₆H₅SO₂CH₃ |
| isothiazole (N, S) | —C₆H₅SO₂CH₃ |
| triazole (N=N, NH) | —C₆H₅SO₂CH₃ |
| thiadiazole (N=N, S) | —C₆H₅SO₂CH₃ |
| thiadiazole (N, S, N) | —C₆H₅SO₂CH₃ |
| oxadiazole (N, O, N) | —C₆H₅SO₂CH₃ |
| oxadiazole (N=N, O) | —C₆H₅SO₂CH₃ |
| Cl-pyrrole (NH) | —C₆H₅SO₂CH₃ |

TABLE VI-continued

General Structure If

| B | R² |
|---|---|
| 5-chloro-pyrrol-2-yl (H on N) | $-C_6H_5SO_2CH_3$ |
| 1,2,5-oxadiazol-3-yl | $-C_6H_5SO_2CH_3$ |
| 1,2,5-thiadiazol-3-yl | $-C_6H_5SO_2CH_3$ |

TABLE VII

General Structure Ig

| R¹ | R² | R⁴ |
|---|---|---|
| $-CF_3$ | $-C_6H_5SO_2CH_3$ | H |
| $-CF_2H$ | $-C_6H_5SO_2CH_3$ | H |
| $-CF_2Cl$ | $-C_6H_5SO_2CH_3$ | H |
| $-CF_2CF_3$ | $-C_6H_5SO_2CH_3$ | H |
| $-CO_2H$ | $-C_6H_5SO_2CH_3$ | H |
| $-CO_2CH_3$ | $-C_6H_5SO_2CH_3$ | H |
| $-CO_2C_2H_5$ | $-C_6H_5SO_2CH_3$ | H |
| $-CONH_2$ | $-C_6H_5SO_2CH_3$ | H |
| $-CONHCH_3$ | $-C_6H_5SO_2CH_3$ | H |
| $-CONH(C_6H_3)$ | $-C_6H_5SO_2CH_3$ | H |
| $-CON(CH_3)_2$ | $-C_6H_5SO_2CH_3$ | H |
| $-CON(C_2H_5)_2$ | $-C_6H_5SO_2CH_3$ | H |
| $-CON(CH_3)(C_2H_5)$ | $-C_6H_5SO_2CH_3$ | H |
| $-CON(CH_3)(C_6H_5)$ | $-C_6H_5SO_2CH_3$ | H |
| $-C(O)$-pyrrolidin-1-yl | $-C_6H_5SO_2CH_3$ | H |
| $-C(O)$-piperidin-1-yl | $-C_6H_5SO_2CH_3$ | H |
| $-CN$ | $-C_6H_5SO_2CH_3$ | H |
| $-CH_2OH$ | $-C_6H_5SO_2CH_3$ | H |
| $-CH_2OCH_3$ | $-C_6H_5SO_2CH_3$ | H |
| $-CH_2OC_2H_5$ | $-C_6H_5SO_2CH_3$ | H |
| $-CH_2OC_6H_5$ | $-C_6H_5SO_2CH_3$ | H |
| $-CH_2SCH_3$ | $-C_6H_5SO_2CH_3$ | H |
| $-CH_2SC_2H_5$ | $-C_6H_5SO_2CH_3$ | H |
| $-CH_2SC_6H_5$ | $-C_6H_5SO_2CH_3$ | H |
| $-CH_2SOCH_3$ | $-C_6H_5SO_2CH_3$ | H |
| $-CH_2SOC_2H_5$ | $-C_6H_5SO_2CH_3$ | H |
| $-CH_2SOC_6H_5$ | $-C_6H_5SO_2CH_3$ | H |
| $-CH_2SO_2CH_3$ | $-C_6H_5SO_2CH_3$ | H |
| $-CH_2SO_2C_2H_5$ | $-C_6H_5SO_2CH_3$ | H |
| $-CH_2SO_2C_6H_5$ | $-C_6H_5SO_2CH_3$ | H |
| $-CF_3$ | $-C_6H_5SO_2CH_3$ | 6-F |
| $-CF_3$ | $-C_6H_5SO_2CH_3$ | 7-F |
| $-CF_3$ | $-C_6H_5SO_2CH_3$ | 8-F |
| $-CF_3$ | $-C_6H_5SO_2CH_3$ | 7-Cl |
| $-CF_3$ | $-C_6H_5SO_2CH_3$ | 8-Cl |
| $-CF_3$ | $-C_6H_5SO_2CH_3$ | 7,8-$(OCH_2O)-$ |
| $-CF_3$ | $-C_6H_5SO_2CH_3$ | 7-$N(CH_3)_2$ |
| $-CF_3$ | $-C_6H_5SO_2CH_3$ | 7-$OCH_3$ |
| $-CF_3$ | $-C_6H_5SO_2CH_3$ | 6-F, 7-$OCH_3$ |
| $-CF_3$ | $-C_6H_5SO_2CH_3$ | 6-Cl, 7-$OCH_3$ |
| $-CF_3$ | $-C_6H_5SO_2CH_3$ | 7-Cl, 6-F |
| $-CF_3$ | $-C_6H_5SO_2CH_3$ | 7-$CH_3$ |
| $-CF_3$ | $-C_6H_5SO_2CH_3$ | 6-F, 7-$CH_3$ |
| $-CF_3$ | $-C_6H_5SO_2CH_3$ | 6,7-F |
| $-CF_3$ | $-C_6H_5SO_2CH_3$ | 7-$SCH_3$ |
| $-CF_3$ | $-C_6H_5SO_2CH_3$ | 6-F, 7-$SCH_3$ |
| $-CF_3$ | $-C_6H_5SO_2CH_3$ | 7-$SOCH_3$ |
| $-CF_3$ | $-C_6H_5SO_2CH_3$ | 6-F, 7-$SOCH_3$ |
| $-CF_3$ | $-C_6H_5SO_2CH_3$ | 6-F, 7-$CH_3$ |
| $-CF_3$ | $-C_6H_5F$ | 7-$SO_2CH_3$ |
| $-CF_3$ | $-C_6H_5Cl$ | 7-$SO_2CH_3$ |
| $-CF_3$ | $-C_6H_5OCH_3$ | 7-$SO_2CH_3$ |
| $-CF_3$ | $-C_6H_5CH_3$ | 7-$SO_2CH_3$ |
| $-CF_3$ | $-C_6H_5SONH_3$ | 7-$SO_2CH_3$ |
| $-CF_3$ | $-C_6H_5SO_2NH_2$ | H |
| $-CF_2H$ | $-C_6H_5SO_2NH_2$ | H |
| $-CF_2Cl$ | $-C_6H_5SO_2NH_2$ | H |
| $-CF_2CF_3$ | $-C_6H_5SO_2NH_2$ | H |
| $-CO_2H$ | $-C_6H_5SO_2NH_2$ | H |
| $-CO_2CH_3$ | $-C_6H_5SO_2NH_2$ | H |
| $-CO_2C_2H_5$ | $-C_6H_5SO_2NH_2$ | H |
| $-CONH_2$ | $-C_6H_5SO_2NH_2$ | H |
| $-CONHCH_3$ | $-C_6H_5SO_2NH_2$ | H |
| $-CONH(C_6H_3)$ | $-C_6H_5SO_2NH_2$ | H |
| $-CON(CH_3)_2$ | $-C_6H_5SO_2NH_2$ | H |
| $-CON(C_2H_5)_2$ | $-C_6H_5SO_2NH_2$ | H |
| $-CON(CH_3)(C_2H_5)$ | $-C_6H_5SO_2NH_2$ | H |
| $-CON(CH_3)(C_6H_5)$ | $-C_6H_5SO_2NH_2$ | H |
| $-C(O)$-pyrrolidin-1-yl | $-C_6H_5SO_2NH_2$ | H |
| $-C(O)$-piperidin-1-yl | $-C_6H_5SO_2NH_2$ | H |
| $-CN$ | $-C_6H_5SO_2NH_2$ | H |
| $-CH_2OH$ | $-C_6H_5SO_2NH_2$ | H |
| $-CH_2OCH_3$ | $-C_6H_5SO_2NH_2$ | H |
| $-CH_2OC_2H_5$ | $-C_6H_5SO_2NH_2$ | H |
| $-CH_2OC_6H_5$ | $-C_6H_5SO_2NH_2$ | H |
| $-CH_2SCH_3$ | $-C_6H_5SO_2NH_2$ | H |
| $-CH_2SC_2H_5$ | $-C_6H_5SO_2NH_2$ | H |
| $-CH_2SC_6H_5$ | $-C_6H_5SO_2NH_2$ | H |
| $-CH_2SOCH_3$ | $-C_6H_5SO_2NH_2$ | H |
| $-CH_2SOC_2H_5$ | $-C_6H_5SO_2NH_2$ | H |
| $-CH_2SOC_6H_5$ | $-C_6H_5SO_2NH_2$ | H |
| $-CH_2SO_2CH_3$ | $-C_6H_5SO_2NH_2$ | H |
| $-CH_2SO_2C_2H_5$ | $-C_6H_5SO_2NH_2$ | H |
| $-CH_2SO_2C6H_5$ | $-C_6H_5SO_2NH_2$ | H |
| $-CF_3$ | $-C_6H_5SO_2NH_2$ | 6-F |
| $-CF_3$ | $-C_6H_5SO_2NH_2$ | 7-F |
| $-CF_3$ | $-C_6H_5SO_2NH_2$ | 8-F |
| $-CF_3$ | $-C_6H_5SO_2NH_2$ | 7-Cl |
| $-CF_3$ | $-C_6H_5SO_2NH_2$ | 8-Cl |
| $-CF_3$ | $-C_6H_5SO_2NH_2$ | 7,8-$(OCH_2O)-$ |
| $-CF_3$ | $-C_6H_5SO_2NH_2$ | 7-$N(CH_3)_2$ |
| $-CF_3$ | $-C_6H_5SO_2NH_2$ | 7-$OCH_3$ |
| $-CF_3$ | $-C_6H_5SO_2NH_2$ | 6-F, 7-$OCH_3$ |
| $-CF_3$ | $-C_6H_5SO_2NH_2$ | 6-Cl, 7-$OCH_3$ |
| $-CF_3$ | $-C_6H_5SO_2NH_2$ | 7-Cl, 6-F |
| $-CF_3$ | $-C_6H_5SO_2NH_2$ | 7-$CH_3$ |
| $-CF_3$ | $-C_6H_5SO_2NH_2$ | 6-F, 7-$CH_3$ |
| $-CF_3$ | $-C_6H_5SO_2NH_2$ | 6,7-F |
| $-CF_3$ | $-C_6H_5SO_2NH_2$ | 7-$SCH_3$ |
| $-CF_3$ | $-C_6H_5SO_2NH_2$ | 6-F, 7-$SCH_3$ |
| $-CF_3$ | $-C_6H_5SO_2NH_2$ | 7-$SOCH_3$ |
| $-CF_3$ | $-C_6H_5SO_2NH_2$ | 6-F, 7-$SOCH_3$ |
| $-CF_3$ | $-C_6H_5SO_2NH_2$ | 6-F, 7-$CH_3$ |
| $-CF_3$ | $-$thienyl$SO_2NH_2$ | 6-F, 7-$OCH_3$ |
| $-CF_3$ | $-C_6H_5F$ | 7-$SO_2NH_2$ |
| $-CF_3$ | $-C_6H_5Cl$ | 7-$SO_2NH_2$ |

TABLE VII-continued

General Structure Ig

| R¹ | R² | R⁴ |
|---|---|---|
| —CF₃ | —C₆H₅OCH₃ | 7-SO₂NH₂ |
| —CF₃ | —C₆H₅CH₃ | 7-SO₂NH₂ |
| —CF₃ | —C₆H₅SOCH₃ | 7-SO₂NH₂ |

TABLE VIII

General Structure Ih

| B | R² |
|---|---|
| 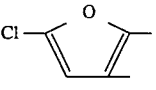 | —C₆H₅SO₂CH₃ |
| 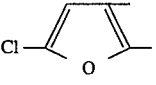 | —C₆H₅SO₂CH₃ |
| 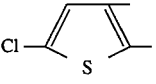 | —C₆H₅SO₂CH₃ |
| 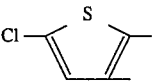 | —C₆H₅SO₂CH₃ |
| 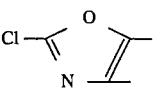 | —C₆H₅SO₂CH₃ |
| 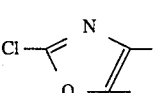 | —C₆H₅SO₂CH₃ |
| 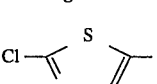 | —C₆H₅SO₂CH₃ |
| 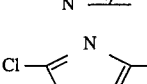 | —C₆H₅SO₂CH₃ |
| 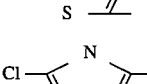 | —C₆H₅SO₂CH₃ |
| 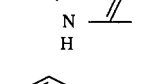 | —C₆H₅SO₂CH₃ |
| 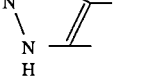 | —C₆H₅SO₂CH₃ |
| 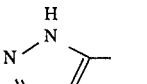 | —C₆H₅SO₂CH₃ |
| 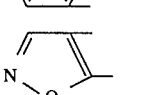 | —C₆H₅SO₂CH₃ |

TABLE VIII-continued

General Structure Ih

| B | R² |
|---|---|
| 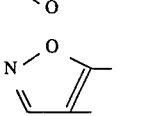 | —C₆H₅SO₂CH₃ |
| 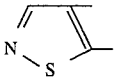 | —C₆H₅SO₂CH₃ |
| 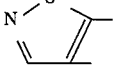 | —C₆H₅SO₂CH₃ |
| 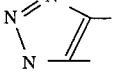 | —C₆H₅SO₂CH₃ |
| 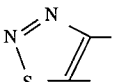 | —C₆H₅SO₂CH₃ |
| 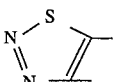 | —C₆H₅SO₂CH₃ |
| 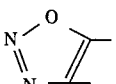 | —C₆H₅SO₂CH₃ |
| 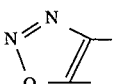 | —C₆H₅SO₂CH₃ |
| 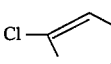 | —C₆H₅SO₂CH₃ |
| 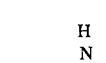 | —C₆H₅SO₂CH₃ |
| 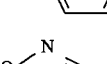 | —C₆H₅SO₂CH₃ |
| 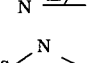 | —C₆H₅SO₂CH₃ |
| 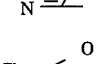 | —C₆H₅SO₂CH₃ |
| 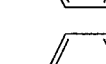 | —C₆H₅SO₂NH₂ |
| 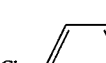 | —C₆H₅SO₂NH₂ |
| 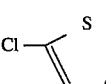 | —C₆H₅SO₂NH₂ |
|  | —C₆H₅SO₂NH₂ |

TABLE VIII-continued

General Structure Ih

| B | R² |
|---|---|
| 4-chloro-oxazol-2-yl (Cl, O, N ring) | $-C_6H_5SO_2NH_2$ |
| 4-chloro-oxazol-5-yl (Cl, N, O ring) | $-C_6H_5SO_2NH_2$ |
| 4-chloro-thiazol-2-yl (Cl, S, N ring) | $-C_6H_5SO_2NH_2$ |
| 4-chloro-thiazol-5-yl (Cl, N, S ring) | $-C_6H_5SO_2NH_2$ |
| 4-chloro-imidazolyl (Cl, N, NH ring) | $-C_6H_5SO_2NH_2$ |
| pyrazol-4-yl (N, NH) | $-C_6H_5SO_2NH_2$ |
| pyrazol-3-yl (NH, N) | $-C_6H_5SO_2NH_2$ |
| isoxazol-4-yl (N, O) | $-C_6H_5SO_2NH_2$ |
| isoxazol-3-yl (O, N) | $-C_6H_5SO_2NH_2$ |
| isothiazol-4-yl (N, S) | $-C_6H_5SO_2NH_2$ |
| isothiazol-3-yl (S, N) | $-C_6H_5SO_2NH_2$ |
| 1,2,3-triazol-4-yl (N, N, NH) | $-C_6H_5SO_2NH_2$ |
| 1,2,3-thiadiazol-4-yl (N, N, S) | $-C_6H_5SO_2NH_2$ |
| 1,2,3-oxadiazol-4-yl (N, N, O) | $-C_6H_5SO_2NH_2$ |
| 1,2,5-oxadiazol-3-yl (N, O, N) | $-C_6H_5SO_2NH_2$ |
| 5-chloro-pyrrol-3-yl (Cl, NH) | $-C_6H_5SO_2NH_2$ |
| 5-chloro-pyrrol-2-yl (NH, Cl) | $-C_6H_5SO_2NH_2$ |
| 1,2,5-oxadiazol-3-yl (O, N, N) | $-C_6H_5SO_2NH_2$ |
| 1,2,5-thiadiazol-3-yl (S, N, N) | $-C_6H_5SO_2NH_2$ |

TABLE IX

General Structure Ii

| p | R¹ | R² | R⁴ |
|---|---|---|---|
| 0 | $-CF_3$ | $-C_6H_5SO_2CH_3$ | H |
| 0 | $-CF_2H$ | $-C_6H_5SO_2CH_3$ | H |
| 0 | $-CF_2Cl$ | $-C_6H_5SO_2CH_3$ | H |
| 0 | $-CF_2CF_3$ | $-C_6H_5SO_2CH_3$ | H |
| 0 | $-CO_2H$ | $-C_6H_5SO_2CH_3$ | H |
| 0 | $-CO_2CH_3$ | $-C_6H_5SO_2CH_3$ | H |
| 0 | $-CO_2C_2H_5$ | $-C_6H_5SO_2CH_3$ | H |
| 0 | $-CONH_2$ | $-C_6H_5SO_2CH_3$ | H |
| 0 | $-CONHCH_3$ | $-C_6H_5SO_2CH_3$ | H |
| 0 | $-CONH(C_6H_5)$ | $-C_6H_5SO_2CH_3$ | H |
| 0 | $-CON(CH_3)_2$ | $-C_6H_5SO_2CH_3$ | H |
| 0 | $-CON(C_2H_5)_2$ | $-C_6H_5SO_2CH_3$ | H |
| 0 | $-CON(CH_3)(C_2H_5)$ | $-C_6H_5SO_2CH_3$ | H |
| 0 | $-CON(CH_3)(C_6H_5)$ | $-C_6H_5SO_2CH_3$ | H |
| 0 | $-C(=O)$-pyrrolidin-1-yl | $-C_6H_5SO_2CH_3$ | H |
| 0 | $-C(=O)$-piperidin-1-yl | $-C_6H_5SO_2CH_3$ | H |
| 0 | $-CN$ | $-C_6H_5SO_2CH_3$ | H |
| 0 | $-CH_2OH$ | $-C_6H_5SO_2CH_3$ | H |
| 0 | $-CH_2OCH_3$ | $-C_6H_5SO_2CH_3$ | H |
| 0 | $-CH_2OC_2H_5$ | $-C_6H_5SO_2CH_3$ | H |
| 0 | $-CH_2OC_6H_5$ | $-C_6H_5SO_2CH_3$ | H |
| 0 | $-CH_2SCH_3$ | $-C_6H_5SO_2CH_3$ | H |
| 0 | $-CH_2SC_2H_5$ | $-C_6H_5SO_2CH_3$ | H |
| 0 | $-CH_2SC_6H_5$ | $-C_6H_5SO_2CH_3$ | H |
| 0 | $-CH_2SOCH_3$ | $-C_6H_5SO_2CH_3$ | H |
| 0 | $-CH_2SOC_2H_5$ | $-C_6H_5SO_2CH_3$ | H |
| 0 | $-CH_2SOC_6H_5$ | $-C_6H_5SO_2CH_3$ | H |
| 0 | $-CH_2SO_2CH_3$ | $-C_6H_5SO_2CH_3$ | H |
| 0 | $-CH_2SO_2C_2H_5$ | $-C_6H_5SO_2CH_3$ | H |
| 0 | $-CH_2SO_2C_6H_5$ | $-C_6H_5SO_2CH_3$ | H |

TABLE IX-continued

General Structure Ii

| p | R¹ | R² | R⁴ |
|---|---|---|---|
| 0 | —CF₃ | —C₆H₅SO₂CH₃ | 6-F |
| 0 | —CF₃ | —C₆H₅SO₂CH₃ | 7-F |
| 0 | —CF₃ | —C₆H₅SO₂CH₃ | 8-F |
| 0 | —CF₃ | —C₆H₅SO₂CH₃ | 7-Cl |
| 0 | —CF₃ | —C₆H₅SO₂CH₃ | 8-Cl |
| 0 | —CF₃ | —C₆H₅SO₂CH₃ | 7,8-(OCH₂O)— |
| 0 | —CF₃ | —C₆H₅SO₂CH₃ | 7-N(CH₃)₂ |
| 0 | —CF₃ | —C₆H₅SO₂CH₃ | 7-OCH₃ |
| 0 | —CF₃ | —C₆H₅SO₂CH₃ | 6-F, 7-OCH₃ |
| 0 | —CF₃ | —C₆H₅SO₂CH₃ | 6-Cl, 7-OCH₃ |
| 0 | —CF₃ | —C₆H₅SO₂CH₃ | 7-Cl, 6-F |
| 0 | —CF₃ | —C₆H₅SO₂CH₃ | 7-CH₃ |
| 0 | —CF₃ | —C₆H₅SO₂CH₃ | 6-F, 7-CH₃ |
| 0 | —CF₃ | —C₆H₅SO₂CH₃ | 6,7-F |
| 0 | —CF₃ | —C₆H₅SO₂CH₃ | 7-SCH₃ |
| 0 | —CF₃ | —C₆H₅SO₂CH₃ | 6-F, 7-SCH₃ |
| 0 | —CF₃ | —C₆H₅SO₂CH₃ | 7-SOCH₃ |
| 0 | —CF₃ | —C₆H₅SO₂CH₃ | 6-F, 7-SOCH₃ |
| 0 | —CF₃ | —C₆H₅SO₂CH₃ | 6-F, 7-CH₃ |
| 0 | —CF₃ | —C₆H₅F | 7-SO₂CH₃ |
| 0 | —CF₃ | —C₆H₅Cl | 7-SO₂CH₃ |
| 0 | —CF₃ | —C₆H₅OCH₃ | 7-SO₂CH₃ |
| 0 | —CF₃ | —C₆H₅CH₃ | 7-SO₂CH₃ |
| 0 | —CF₃ | —C₆H₅SOCH₃ | 7-SO₂CH₃ |
| 0 | —CF₃ | —C₆H₅SO₂NH₂ | H |
| 0 | —CF₂H | —C₆H₅SO₂NH₂ | H |
| 0 | —CF₂Cl | —C₆H₅SO₂NH₂ | H |
| 0 | —CF₂CF₃ | —C₆H₅SO₂NH | H |
| 0 | —CO₂H | —C₆H₅SO₂NH₂ | H |
| 0 | —CO₂CH₃ | —C₆H₅SO₂NH₂ | H |
| 0 | —CO₂C₂H₅ | —C₆H₅SO₂NH₂ | H |
| 0 | —CONH₂ | —C₆H₅SO₂NH₂ | H |
| 0 | —CONHCH₃ | —C₆H₅SO₂NH₂ | H |
| 0 | —CONH(C₆H₃) | —C₆H₅SO₂NH₂ | H |
| 0 | —CON(CH₃)₂ | —C₆H₅SO₂NH₂ | H |
| 0 | —CON(C₂H₅)₂ | —C₆H₅SO₂NH₂ | H |
| 0 | —CON(CH₃)(C₂H₅) | —C₆H₅SO₂NH₂ | H |
| 0 | —CON(CH₃)(C₆H₅) | —C₆H₅SO₂NH₂ | H |
| 0 | 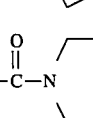 | —C₆H₅SO₂NH₂ | H |
| 0 | 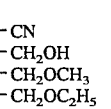 | —C₆H₅SO₂NH₂ | H |
| 0 | —CN | —C₆H₅SO₂NH₂ | H |
| 0 | —CH₂OH | —C₆H₅SO₂NH₂ | H |
| 0 | —CH₂OCH₃ | —C₆H₅SO₂NH₂ | H |
| 0 | —CH₂OC₂H₅ | —C₆H₅SO₂NH₂ | H |
| 0 | —CH₂OC₆H₅ | —C₆H₅SO₂NH₂ | H |
| 0 | —CH₂SCH₃ | —C₆H₅SO₂NH₂ | H |
| 0 | —CH₂SC₂H₅ | —C₆H₅SO₂NH₂ | H |
| 0 | —CH₂SC₆H₅ | —C₆H₅SO₂NH₂ | H |
| 0 | —CH₂SOCH₃ | —C₆H₅SO₂NH₂ | H |
| 0 | —CH₂SOC₂H₅ | —C₆H₅SO₂NH₂ | H |
| 0 | —CH₂SOC₆H₅ | —C₆H₅SO₂NH₂ | H |
| 0 | —CH₂SO₂CH₃ | —C₆H₅SO₂NH₂ | H |
| 0 | —CH₂SO₂C₂H₅ | —C₆H₅SO₂NH₂ | H |
| 0 | —CH₂SO₂C₆H₅ | —C₆H₅SO₂NH₂ | H |
| 0 | —CONH₂ | —C₆H₅SO₂NH₂ | 7-F |
| 0 | —CO₂CH₃ | —C₆H₅SO₂NH₂ | 7-F |
| 0 | —CF₃ | —C₆H₅SO₂NH₂ | 6-F |
| 0 | —CF₃ | —C₆H₅SO₂NH₂ | 7-F |
| 0 | —CF₃ | —C₆H₅SO₂NH₂ | 8-F |
| 0 | —CF₃ | —C₆H₅SO₂NH₂ | 7-Cl |
| 0 | —CF₃ | —C₆H₅SO₂NH₂ | 8-Cl |
| 0 | —CF₃ | —C₆H₅SO₂NH₂ | 7,8-(OCH₂O)— |
| 0 | —CF₃ | —C₆H₅SO₂NH₂ | 7-N(CH₃)₂ |
| 0 | —CF₃ | —C₆H₅SO₂NH₂ | 7-OCH₃ |
| 0 | —CF₃ | —C₆H₅SO₂NH₂ | 6-F, 7-OCH₃ |
| 0 | —CF₃ | —C₆H₅SO₂NH₂ | 6-Cl, 7-OCH₃ |
| 0 | —CF₃ | —C₆H₅SO₂NH₂ | 7-Cl, 6-F |
| 0 | —CF₃ | —C₆H₅SO₂NH₂ | 7-CH₃ |
| 0 | —CF₃ | —C₆H₅SO₂NH₂ | 6-F, 7-CH₃ |
| 0 | —CF₃ | —C₆H₅SO₂NH₂ | 6,7-F |
| 0 | —CF₃ | —C₆H₅SO₂NH₂ | 7-SCH₃ |
| 0 | —CF₃ | —C₆H₅SO₂NH₂ | 6-F, 7-SCH₃ |
| 0 | —CF₃ | —C₆H₅SO₂NH₂ | 7-SOCH₃ |
| 0 | —CF₃ | —C₆H₅SO₂NH₂ | 6-F, 7-SOCH₃ |
| 0 | —CF₃ | —C₆H₅SO₂NH₂ | 6-Cl, 7-CH₃ |
| 0 | —CF₃ | —thienylSO₂NH₂ | 6-F, 7-OCH₃ |
| 0 | —CF₃ | —C₆H₅F | 7-SO₂NH₂ |
| 0 | —CF₃ | —C₆H₅Cl | 7-SO₂NH₂ |
| 0 | —CF₃ | —C₆H₅OCH₃ | 7-SO₂NH₂ |
| 0 | —CF₃ | —C₆H₅CH₃ | 7-SO₂NH₂ |
| 0 | —CF₃ | —C₆H₅SOCH₃ | 7-SO₂NH₂ |
| 0 | —CHF₂ | —C₆H₅SO₂NH₂ | 6-F, 7-OCH₃ |
| 1 | —CF₃ | —C₆H₅SO₂NH₂ | 6-F, 7-OCH₃ |
| 1 | —CF₃ | —C₆H₅SO₂NH₂ | 6-Cl, 7-OCH₃ |
| 1 | —CF₃ | —C₆H₅SO₂NH₂ | 7-Cl, 6-F |
| 1 | —CF₃ | —C₆H₅SO₂NH₂ | 6-F, 7-CH₃ |
| 1 | —CF₃ | —C₆H₅SO₂NH₂ | 6,7-F |
| 1 | —CF₃ | —C₆H₅SO₂NH₂ | 6-F, 7-SCH₃ |
| 1 | —CF₃ | —C₆H₅SO₂NH₂ | 6-F, 7-SOCH₃ |
| 1 | —CF₃ | —C₆H₅SO₂NH₂ | 6-Cl, 7-CH₃ |

TABLE X

General Structure Ij

| B | R² | p |
|---|---|---|
| 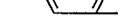 | —C₆H₅SO₂CH₂ | 0 |
|  | —C₆H₅SO₂CH₂ | 0 |
| 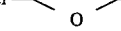 | —C₆H₅SO₂CH₂ | 0 |
| 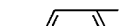 | —C₆H₅SO₂CH₂ | 0 |
|  | —C₆H₅SO₂CH₂ | 0 |
|  | —C₆H₅SO₂CH₃ | 0 |
|  | —C₆H₅SO₂CH₂ | 0 |

TABLE X-continued

General Structure Ij

| B | R² | p |
|---|---|---|
| 2-chloro-1H-imidazol-4,5-diyl | —C₆H₅SO₂CH₂ | 0 |
| 1H-pyrazol-3,4-diyl | —C₆H₅SO₂CH₂ | 0 |
| 1H-pyrazol-3,5-diyl | —C₆H₅SO₂CH₂ | 0 |
| isoxazol-3,4-diyl | —C₆H₅SO₂CH₂ | 0 |
| isoxazol-3,5-diyl | —C₆H₅SO₂CH₂ | 0 |
| isothiazol-3,4-diyl | —C₆H₅SO₂CH₂ | 0 |
| isothiazol-3,5-diyl | —C₆H₅SO₂CH₂ | 0 |
| 1H-1,2,3-triazol-4,5-diyl | —C₆H₅SO₂CH₂ | 0 |
| 1,2,3-thiadiazol-4,5-diyl | —C₆H₅SO₂CH₂ | 0 |
| 1,2,3-thiadiazol-4,5-diyl | —C₆H₅SO₂CH₂ | 0 |
| 1,2,3-oxadiazol-4,5-diyl | —C₆H₅SO₂CH₂ | 0 |
| 1,2,3-oxadiazol-4,5-diyl | —C₆H₅SO₂CH₂ | 0 |
| 5-chloro-1H-pyrrol-2,3-diyl | —C₆H₅SO₂CH₂ | 0 |
| 5-chloro-1H-pyrrol-2,5-diyl | —C₆H₅SO₂CH₂ | 0 |

TABLE X-continued

General Structure Ij

| B | R² | p |
|---|---|---|
| 1,2,5-oxadiazol-3,4-diyl | —C₆H₅SO₂CH₂ | 0 |
| 1,2,5-thiadiazol-3,4-diyl | —C₆H₅SO₂CH₂ | 0 |
| 5-chlorofuran-2,3-diyl | —C₆H₅SO₂NH₂ | 0 |
| 5-chlorofuran-2,4-diyl | —C₆H₅SO₂NH₂ | 0 |
| 5-chlorothiophen-2,3-diyl | —C₆H₅SO₂NH₂ | 0 |
| 5-chlorothiophen-2,4-diyl | —C₆H₅SO₂NH₂ | 0 |
| 5-chloroisoxazol-3,4-diyl | —C₆H₅SO₂NH₂ | 0 |
| 5-chloroisoxazol-3,4-diyl | —C₆H₅SO₂NH₂ | 0 |
| 5-chloroisothiazol-3,4-diyl | —C₆H₅SO₂NH₂ | 0 |
| 5-chloroisothiazol-3,4-diyl | —C₆H₅SO₂NH₂ | 0 |
| 5-chloro-1H-imidazol-2,4-diyl | —C₆H₅SO₂NH₂ | 0 |
| 1H-pyrazol-3,4-diyl | —C₆H₅SO₂NH₂ | 0 |
| 1H-pyrazol-3,5-diyl | —C₆H₅SO₂NH₂ | 0 |
| isoxazol-3,4-diyl | —C₆H₅SO₂NH₂ | 0 |
| isoxazol-3,5-diyl | —C₆H₅SO₂NH₂ | 0 |

TABLE X-continued

General Structure Ij

| B | R² | p |
|---|----|----|
| 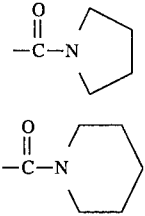 (N-S thiazole) | —C₆H₅SO₂NH₂ | 0 |
| (N-S isothiazole) | —C₆H₅SO₂NH₂ | 0 |
| (N=N-NH triazole) | —C₆H₅SO₂NH₂ | 0 |
| (N=N-S thiadiazole) | —C₆H₅SO₂NH₂ | 0 |
| (N-S-N thiadiazole) | —C₆H₅SO₂NH₂ | 0 |
| (N-O-N oxadiazole) | —C₆H₅SO₂NH₂ | 0 |
| (N=N-O oxadiazole) | —C₆H₅SO₂NH₂ | 0 |
| Cl-pyrrole (NH) | —C₆H₅SO₂NH₂ | 0 |
| Cl-pyrrole (NH) | —C₆H₅SO₂NH₂ | 0 |
| O-N isoxazole | —C₆H₅SO₂NH₂ | 0 |
| S-N isothiazole | —C₆H₅SO₂NH₂ | 0 |
| Cl-thiophene | —C₆H₅SO₂NH₂ | 1 |

TABLE XI

General Structure Ik

| p | R¹ | R² | R⁴ |
|---|----|----|----|
| 0 | —CF₃ | —C₆H₅SO₂CH₃ | H |
| 0 | —CF₂H | —C₆H₅SO₂CH₃ | H |
| 0 | —CF₂Cl | —C₆H₅SO₂CH₃ | H |
| 0 | —CF₂CF₃ | —C₆H₅SO₂CH₃ | H |
| 0 | —CO₂H | —C₆H₅SO₂CH₃ | H |
| 0 | —CO₂CH₃ | —C₆H₅SO₂CH₃ | H |
| 0 | —CO₂C₂H₅ | —C₆H₅SO₂CH₃ | H |
| 0 | —CONH₂ | —C₆H₅SO₂CH₃ | H |
| 0 | —CONHCH₃ | —C₆H₅SO₂CH₃ | H |
| 0 | —CONH(C₆H₅) | —C₆H₅SO₂CH₃ | H |
| 0 | —CON(CH₃)₂ | —C₆H₅SO₂CH₃ | H |
| 0 | —CON(C₂H₅)₂ | —C₆H₅SO₂CH₃ | H |
| 0 | —CON(CH₃)(C₂H₅) | —C₆H₅SO₂CH₃ | H |
| 0 | —CON(CH₃)(C₆H₅) | —C₆H₅SO₂CH₃ | H |
| 0 | —C(O)N-pyrrolidinyl | —C₆H₅SO₂CH₃ | H |
| 0 | —C(O)N-piperidinyl | —C₆H₅SO₂CH₃ | H |
| 0 | —CN | —C₆H₅SO₂CH₃ | H |
| 0 | —CH₂OH | —C₆H₅SO₂CH₃ | H |
| 0 | —CH₂OCH₃ | —C₆H₅SO₂CH₃ | H |
| 0 | —CH₂OC₂H₅ | —C₆H₅SO₂CH₃ | H |
| 0 | —CH₂OC₆H₅ | —C₆H₅SO₂CH₃ | H |
| 0 | —CH₂SCH₃ | —C₆H₅SO₂CH₃ | H |
| 0 | —CH₂SC₂H₅ | —C₆H₅SO₂CH₃ | H |
| 0 | —CH₂SC₆H₅ | —C₆H₅SO₂CH₃ | H |
| 0 | —CH₂SOCH₃ | —C₆H₅SO₂CH₃ | H |
| 0 | —CH₂SOC₂H₅ | —C₆H₅SO₂CH₃ | H |
| 0 | —CH₂SOC₆H₅ | —C₆H₅SO₂CH₃ | H |
| 0 | —CH₂SO₂CH₃ | —C₆H₅SO₂CH₃ | H |
| 0 | —CH₂SO₂C₂H₅ | —C₆H₅SO₂CH₃ | H |
| 0 | —CH₂SO₂C₆H₅ | —C₆H₅SO₂CH₃ | H |
| 0 | —CF₃ | —C₆H₅SO₂CH₃ | 6-F |
| 0 | —CF₃ | —C₆H₅SO₂CH₃ | 7-F |
| 0 | —CF₃ | —C₆H₅SO₂CH₃ | 8-F |
| 0 | —CF₃ | —C₆H₅SO₂CH₃ | 7-Cl |
| 0 | —CF₃ | —C₆H₅SO₂CH₃ | 8-Cl |
| 0 | —CF₃ | —C₆H₅SO₂CH₃ | 7,8-(OCH₂O)— |
| 0 | —CF₃ | —C₆H₅SO₂CH₃ | 7-N(CH₃)₂ |
| 0 | —CF₃ | —C₆H₅SO₂CH₃ | 7-OCH₃ |
| 0 | —CF₃ | —C₆H₅SO₂CH₃ | 6-F, 7-OCH₃ |
| 0 | —CF₃ | —C₆H₅SO₂CH₃ | 6-Cl, 7-OCH₃ |
| 0 | —CF₃ | —C₆H₅SO₂CH₃ | 7-Cl, 6-F |
| 0 | —CF₃ | —C₆H₅SO₂CH₃ | 7-CH₃ |
| 0 | —CF₃ | —C₆H₅SO₂CH₃ | 6-F, 7-CH₃ |
| 0 | —CF₃ | —C₆H₅SO₂CH₃ | 6,7-CH₃ |
| 0 | —CF₃ | —C₆H₅SO₂CH₃ | 7-SCH₃ |
| 0 | —CF₃ | —C₆H₅SO₂CH₃ | 6-F, 7-SCH₃ |
| 0 | —CF₃ | —C₆H₅SO₂CH₃ | 7-SOCH₃ |
| 0 | —CF₃ | —C₆H₅SO₂CH₃ | 6-F, 7-SOCH₃ |
| 0 | —CF₃ | —C₆H₅SO₂CH₃ | 6-F, 7-CH₃ |
| 0 | —CF₃ | —C₆H₅F | 7-SO₂CH₃ |
| 0 | —CF₃ | —C₆H₅Cl | 7-SO₂CH₃ |
| 0 | —CF₃ | —C₆H₅OCH₃ | 7-SO₂CH₃ |
| 0 | —CF₃ | —C₆H₅CH₃ | 7-SO₂CH₃ |
| 0 | —CF₃ | —C₆H₅SOCH₃ | 7-SO₂CH₃ |
| 0 | —CF₃ | —C₆H₅SO₂NH₂ | H |
| 0 | —CF₂H | —C₆H₅SO₂NH₂ | H |
| 0 | —CF₂Cl | —C₆H₅SO₂NH₂ | H |
| 0 | —CF₂CF₃ | —C₆H₅SO₂NH₂ | H |
| 0 | CO₂H | —C₆H₅SO₂NH₂ | H |
| 0 | —CO₂CH₃ | —C₆H₅SO₂NH₂ | H |
| 0 | —CO₂C₂H₅ | —C₆H₅SO₂NH₂ | H |
| 0 | —CONH₂ | —C₆H₅SO₂NH₂ | H |
| 0 | —CONHCH₃ | —C₆H₅SO₂NH₂ | H |
| 0 | —CONH(C₆H₅) | —C₆H₅SO₂NH₂ | H |
| 0 | —CON(CH₃)₂ | —C₆H₅SO₂NH₂ | H |
| 0 | —CON(C₂H₅)₂ | —C₆H₅SO₂NH₂ | H |
| 0 | —CON(CH₃)(C₂H₅) | —C₆H₅SO₂NH₂ | H |
| 0 | —CON(CH₃)(C₆H₅) | —C₆H₅SO₂NH₂ | H |

TABLE XI-continued

General Structure Ik

| p | R¹ | R² | R⁴ |
|---|---|---|---|
| 0 | 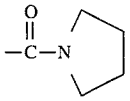 -C(=O)-N(pyrrolidine) | -C₆H₅SO₂NH₂ | H |
| 0 | 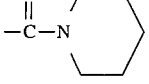 -C(=O)-N(piperidine) | -C₆H₅SO₂NH₂ | H |
| 0 | -CN | -C₆H₅SO₂NH₂ | H |
| 0 | -CH₂OH | -C₆H₅SO₂NH₂ | H |
| 0 | -CH₂OCH₃ | -C₆H₅SO₂NH₂ | H |
| 0 | -CH₂OC₂H₅ | -C₆H₅SO₂NH₂ | H |
| 0 | -CH₂OC₆H₅ | -C₆H₅SO₂NH₂ | H |
| 0 | -CH₂SCH₃ | -C₆H₅SO₂NH₂ | H |
| 0 | -CH₂SC₂H₅ | -C₆SO₂NH₂ | H |
| 0 | -CH₂SC₆H₅ | -C₆H₅SO₂NH₂ | H |
| 0 | -CH₂SOCH₃ | -C₆H₅SO₂NH₂ | H |
| 0 | -CH₂SOC₂H₅ | -C₆H₅SO₂NH₂ | H |
| 0 | -CH₂SOC₆H₅ | -C₆H₅SO₂NH₂ | H |
| 0 | -CH₂SO₂CH₃ | -C₆H₅SO₂NH₂ | H |
| 0 | -CH₂SO₂C₂H₅ | -C₆H₅SO₂NH₂ | H |
| 0 | -CH₂SO₂C₂H₅ | -C₆H₅SO₂NH₂ | H |
| 0 | -CH₂SO₂C₆H₅ | -C₆H₅SO₂NH₂ | H |
| 0 | -CF₃ | -C₆H₅SO₂NH₂ | 6-F |
| 0 | -CF₃ | -C₆H₅SO₂NH₂ | 7-F |
| 0 | -CF₃ | -C₆H₅SO₂NH₂ | 8-F |
| 0 | -CF₃ | -C₆H₅SO₂NH₂ | 7-Cl |
| 0 | -CF₃ | -C₆H₅SO₂NH₂ | 8-Cl |
| 0 | -CF₃ | -C₆H₅SO₂NH₂ | 7,8-(OCH₂O)— |
| 0 | -CF₃ | -C₆H₅SO₂NH₂ | 7-N(CH₃)₂ |
| 0 | -CF₃ | -C₆H₅SO₂NH₂ | 7-OCH₃ |
| 0 | -CF₃ | -C₆H₅SO₂NH₂ | 7,8-OCH₃ |
| 0 | -CF₃ | -C₆H₅SO₂NH₂ | 6-F, 7-OCH₃ |
| 0 | -CF₃ | -C₆H₅SO₂NH₂ | 6-Cl, 7-OCH₃ |
| 0 | -CF₃ | -C₆H₅SO₂NH₂ | 7-Cl, 6-F |
| 0 | -CF₃ | -C₆H₅SO₂NH₂ | 6-CH(CH₃)₂ |
| 0 | -CF₃ | -C₆H₅SO₂NH₂ | 7-CH₃ |
| 0 | -CF₃ | -C₆H₅SO₂NH₂ | 6-F, 7-CH₃ |
| 0 | -CF₃ | -C₆H₅SO₂NH₂ | 6,7-F |
| 0 | -CF₃ | -C₆H₅SO₂NH₂ | 6,7-Cl |
| 0 | -CF₃ | -C₆H₅SO₂NH₂ | 7-SCH₃ |
| 0 | -CF₃ | -C₆H₅SO₂NH₂ | 6-F, 7-SCH₃ |
| 0 | -CF₃ | -C₆H₅SO₂NH₂ | 7-SOCH₃ |
| 0 | -CF₃ | -C₆H₅SO₂NH₂ | 6-F, 7-SOCH₃ |
| 0 | -CF₃ | -C₆H₅SO₂NH₂ | 6-Cl, 7-CH₃ |
| 0 | -CF₃ | -thienylSO₂NH₂ | 6-F, 7-OCH₃ |
| 0 | -CF₃ | -C₂H₅F | 7-SO₂NH₂ |
| 0 | -CF₃ | -C₆H₅Cl | 7-SO₂NH₂ |
| 0 | -CF₃ | -C₆H₅OCH₃ | 7-SO₂NH₂ |
| 0 | -CF₃ | -C₆H₅CH₃ | 7-SO₂NH₂ |
| 0 | -CF₃ | -C₆H₅SOCH₃ | 7-SO₂NH₂ |
| 1 | -CF₃ | -C₆H₅SO₂NH₂ | 6-F, 7-OCH₃ |
| 1 | -CF₃ | -C₆H₅SO₂NH₂ | 6-Cl, 7-OCH₃ |
| 1 | -CF₃ | -C₆H₅SO₂NH₂ | 7-Cl, 6-F |
| 1 | -CF₃ | -C₆H₅SO₂NH₂ | 6-F, 7-CH₃ |
| 1 | -CF₃ | -C₆H₅SO₂NH₂ | 6,7-F |
| 1 | -CF₃ | -C₆H₅SO₂NH₂ | 6-F, 7-SCH₃ |
| 1 | -CF₃ | -C₆H₅SO₂NH₂ | 6-F, 7-SOCH₃ |
| 1 | -CF₃ | -C₆H₅SO₂NH₂ | 6-Cl, 7-CH₃ |

TABLE XII

General Structure Il

| B | R² | p |
|---|---|---|
| 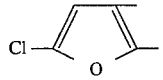 Cl-furan-O | -C₆H₅SO₂CH₃ | 0 |
| 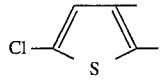 Cl-furan-O | -C₆H₅SO₂CH₃ | 0 |
|  Cl-thiophene-S | -C₆H₅SO₂CH₃ | 0 |
| 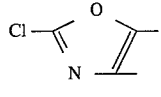 Cl-thiophene-S | -C₆H₅SO₂CH₃ | 0 |
| 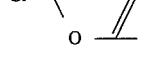 Cl-oxazole | -C₆H₅SO₂CH₃ | 0 |
| 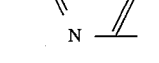 Cl-isoxazole | -C₆H₅SO₂CH₃ | 0 |
| 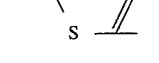 Cl-thiazole | -C₆H₅SO₂CH₃ | 0 |
| 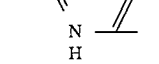 Cl-isothiazole | -C₆H₅SO₂CH₃ | 0 |
| 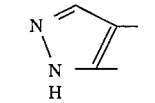 Cl-imidazole | -C₆H₅SO₂CH₃ | 0 |
| 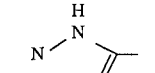 pyrazole | -C₆H₅SO₂CH₃ | 0 |
| 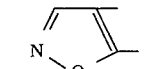 pyrazole | -C₆H₅SO₂CH₃ | 0 |
|  isoxazole | -C₆H₅SO₂CH₃ | 0 |
| 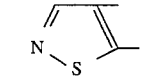 isoxazole | -C₆H₅SO₂CH₃ | 0 |
| 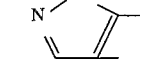 isothiazole | -C₆H₅SO₂CH₃ | 0 |
| 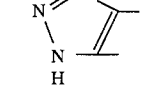 isothiazole | -C₆H₅SO₂CH₃ | 0 |
|  triazole | -C₆H₅SO₂CH₃ | 0 |

TABLE XII-continued

General Structure II

| B | R² | p |
|---|----|---|
| thiadiazole (N=N, S) | $-C_6H_5SO_2CH_3$ | 0 |
| thiadiazole (N, S, N) | $-C_6H_5SO_2CH_3$ | 0 |
| oxadiazole (N=N, O) | $-C_6H_5SO_2CH_3$ | 0 |
| oxadiazole (N=N, O) | $-C_6H_5SO_2CH_3$ | 0 |
| Cl-pyrrole (NH) | $-C_6H_5SO_2CH_3$ | 0 |
| Cl-pyrrole (NH) | $-C_6H_5SO_2CH_3$ | 0 |
| oxadiazole (O, N) | $-C_6H_5SO_2CH_3$ | 0 |
| thiadiazole (S, N, N) | $-C_6H_5SO_2CH_3$ | 0 |
| Cl-furan (O) | $-C_6H_5SO_2NH_3$ | 0 |
| Cl-furan (O) | $-C_6H_5SO_2NH_3$ | 0 |
| Cl-thiophene (S) | $-C_6H_5SO_2NH_3$ | 0 |
| Cl-thiophene (S) | $-C_6H_5SO_2NH_3$ | 0 |
| Cl-oxazole (O, N) | $-C_6H_5SO_2NH_3$ | 0 |
| Cl-oxazole (N, O) | $-C_6H_5SO_2NH_3$ | 0 |
| Cl-thiazole (S, N) | $-C_6H_5SO_2NH_3$ | 0 |
| Cl-thiazole (N, S) | $-C_6H_5SO_2NH_3$ | 0 |
| Cl-imidazole (N, NH) | $-C_6H_5SO_2NH_3$ | 0 |
| pyrazole (N, NH) | $-C_6H_5SO_2NH_3$ | 0 |
| pyrazole (N, NH) | $-C_6H_5SO_2NH_3$ | 0 |
| isoxazole (N, O) | $-C_6H_5SO_2NH_3$ | 0 |
| isoxazole (O, N) | $-C_6H_5SO_2NH_3$ | 0 |
| isothiazole (S, N) | $-C_6H_5SO_2NH_3$ | 0 |
| isothiazole (N, S) | $-C_6H_5SO_2NH_3$ | 0 |
| triazole (N=N, NH) | $-C_6H_5SO_2NH_3$ | 0 |
| thiadiazole (N=N, S) | $-C_6H_5SO_2NH_3$ | 0 |
| thiadiazole (N, S, N) | $-C_6H_5SO_2NH_3$ | 0 |
| oxadiazole (N=N, O) | $-C_6H_5SO_2NH_3$ | 0 |
| oxadiazole (N=N, O) | $-C_6H_5SO_2NH_3$ | 0 |
| Cl-pyrrole (NH) | $-C_6H_5SO_2NH_3$ | 0 |

TABLE XII-continued

General Structure Il

| B | R² | p |
|---|---|---|
|  Cl-pyrrole (H on N) | —C₆H₅SO₂NH₃ | 0 |
|  oxadiazole | —C₆H₅SO₂NH₃ | 0 |
| 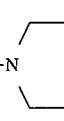 thiadiazole | —C₆H₅SO₂NH₃ | 0 |

TABLE XIII

General Structure Im

| R¹ | R² | R⁴ |
|---|---|---|
| —CF₃ | —C₆H₅SO₂CH₃ | H |
| —CF₂H | —C₆H₅SO₂CH₃ | H |
| —CF₂Cl | —C₆H₅SO₂CH₃ | H |
| —CF₂CF₃ | —C₆H₅SO₂CH₃ | H |
| —CO₂H | —C₆H₅SO₂CH₃ | H |
| —CO₂CH₃ | —C₆H₅SO₂CH₃ | H |
| —CO₂C₂H₅ | —C₆H₅SO₂CH₃ | H |
| —CONH₂ | —C₆H₅SO₂CH₃ | H |
| —CONHCH₃ | —C₆H₅SO₂CH₃ | H |
| —CONH(C₆H₅) | —C₆H₅SO₂CH₃ | H |
| —CON(CH₃)₂ | —C₆H₅SO₂CH₃ | H |
| —CON(C₂H₅)₂ | —C₆H₅SO₂CH₃ | H |
| —CON(CH₃)(C₂H₅) | —C₆H₅SO₂CH₃ | H |
| —CON(CH₃)(C₆H₅) | —C₆H₅SO₂CH₃ | H |
| 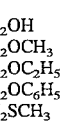 —C(O)N-pyrrolidinyl | —C₆H₅SO₂CH₃ | H |
| —C(O)N-piperidinyl | —C₆H₅SO₂CH₃ | H |
| —CN | —C₆H₅SO₂CH₃ | H |
| —CH₂OH | —C₆H₅SO₂CH₃ | H |
| —CH₂OCH₃ | —C₆H₅SO₂CH₃ | H |
| —CH₂OC₂H₅ | —C₆H₅SO₂CH₃ | H |
| —CH₂OC₆H₅ | —C₆H₅SO₂CH₃ | H |
| —CH₂SCH₃ | —C₆H₅SO₂CH₃ | H |
| —CH₂SC₂H₅ | —C₆H₅SO₂CH₃ | H |
| —CH₂SC₆H₅ | —C₆H₅SO₂CH₃ | H |
| —CH₂SOCH₃ | —C₆H₅SO₂CH₃ | H |
| —CH₂SOC₂H₅ | —C₆H₅SO₂CH₃ | H |
| —CH₂SOC₆H₅ | —C₆H₅SO₂CH₃ | H |
| —CH₂SO₂CH₃ | —C₆H₅SO₂CH₃ | H |
| —CH₂SO₂C₂H₅ | —C₆H₅SO₂CH₃ | H |
| —CH₂SO₂C₆H₅ | —C₆H₅SO₂CH₃ | H |
| —CF₃ | —C₆H₅SO₂CH₃ | 7-F |
| —CF₃ | —C₆H₅SO₂CH₃ | 8-F |
| —CF₃ | —C₆H₅SO₂CH₃ | 9-F |
| —CF₃ | —C₆H₅SO₂CH₃ | 8-Cl |
| —CF₃ | —C₆H₅SO₂CH₃ | 9-Cl |
| —CF₃ | —C₆H₅SO₂CH₃ | 8,9-(OCH₂O)— |
| —CF₃ | —C₆H₅SO₂CH₃ | 8-N(CH₃)₂ |
| —CF₃ | —C₆H₅SO₂CH₃ | 8-OCH₃ |
| —CF₃ | —C₆H₅SO₂CH₃ | 7-F, 8-OCH₃ |
| —CF₃ | —C₆H₅SO₂CH₃ | 7-Cl, 8-OCH₃ |
| —CF₃ | —C₆H₅SO₂CH₃ | 8-Cl, 7-F |
| —CF₃ | —C₆H₅SO₂CH₃ | 8-CH₃ |
| —CF₃ | —C₆H₅SO₂CH₃ | 7-F, 8-CH₃ |
| —CF₃ | —C₆H₅SO₂CH₃ | 7,8-F |
| —CF₃ | —C₆H₅SO₂CH₃ | 8-SCH₃ |
| —CF₃ | —C₆H₅SO₂CH₃ | 7-F, 8-SCH₃ |
| —CF₃ | —C₆H₅SO₂CH₃ | 8-SOCH₃ |
| —CF₃ | —C₆H₅SO₂CH₃ | 7-F, 8-SOCH₃ |
| —CF₃ | —C₆H₅SO₂CH₃ | 7-F, 8-CH₃ |
| —CF₃ | —C₆H₅F | 8-SO₂CH₃ |
| —CF₃ | —C₆H₅Cl | 8-SO₂CH₃ |
| —CF₃ | —C₆H₅OCH₃ | 8-SO₂CH₃ |
| —CF₃ | —C₆H₅CH₃ | 8-SO₂CH₃ |
| —CF₃ | —C₆H₅SOCH₃ | 8-SO₂CH₃ |
| —CF₃ | —C₆H₅SO₂NH₂ | H |
| —CF₂H | —C₆H₅SO₂NH₂ | H |
| —CF₂Cl | —C₆H₅SO₂NH₂ | H |
| —CF₂CF₃ | —C₆H₅SO₂NH₂ | H |
| —CO₂H | —C₆H₅SO₂NH₂ | H |
| —CO₂CH₃ | —C₆H₅SO₂NH₂ | H |
| —CO₂C₂H₅ | —C₆H₅SO₂NH₂ | H |
| —CONH₂ | —C₆H₅SO₂NH₂ | H |
| —CONHCH₃ | —C₆H₅SO₂NH₂ | H |
| —CONH(C₆H₅) | —C₆H₅SO₂NH₂ | H |
| —CON(CH₃)₂ | —C₆H₅SO₂NH₂ | H |
| —CON(C₂H₅)₂ | —C₆H₅SO₂NH₂ | H |
| —CON(CH₃)(C₂H₅) | —C₆H₅SO₂NH₂ | H |
| —CON(CH₃)(C₆H₅) | —C₆H₅SO₂NH₂ | H |
| —C(O)N-pyrrolidinyl | —C₆H₅SO₂NH₂ | H |
| —C(O)N-piperidinyl | —C₆H₅SO₂NH₂ | H |
| —CN | —C₆H₅SO₂NH₂ | H |
| —CH₂OH | —C₆H₅SO₂NH₂ | H |
| —CH₂OCH₃ | —C₆H₅SO₂NH₂ | H |
| —CH₂OC₂H₅ | —C₆H₅SO₂NH₂ | H |
| —CH₂OC₆H₅ | —C₆H₅SO₂NH₂ | H |
| —CH₂SCH₃ | —C₆H₅SO₂NH₂ | H |
| —CH₂SC₂H₅ | —C₆H₅SO₂NH₂ | H |
| —CH₂SC₆H₅ | —C₆H₅SO₂NH₂ | H |
| —CH₂SOCH₃ | —C₆H₅SO₂NH₂ | H |
| —CH₂SOC₂H₅ | —C₆H₅SO₂NH₂ | H |
| —CH₂SOC₆H₅ | —C₆H₅SO₂NH₂ | H |
| —CH₂SO₂CH₃ | —C₆H₅SO₂NH₂ | H |
| —CH₂SO₂C₂H₅ | —C₆H₅SO₂NH₂ | H |
| —CH₂SO₂C₆H₅ | —C₆H₅SO₂NH₂ | H |
| —CF₃ | —C₆H₅SO₂NH₂ | 7-F |
| —CF₃ | —C₆H₅SO₂NH₂ | 8-F |
| —CF₃ | —C₆H₅SO₂NH₂ | 9-F |
| —CF₃ | —C₆H₅SO₂NH₂ | 7,8-(OCH₂O)— |
| —CF₃ | —C₆H₅SO₂NH₂ | 8-N(CH₃)₂ |
| —CF₃ | —C₆H₅SO₂NH₂ | 8-OCH₃ |
| —CF₃ | —C₆H₅SO₂NH₂ | 7-F, 8-OCH₃ |
| —CF₃ | —C₆H₅SO₂NH₂ | 7-Cl, 8-OCH₃ |
| —CF₃ | —C₆H₅SO₂NH₂ | 8-Cl, 7-F |
| —CF₃ | —C₆H₅SO₂NH₂ | 8-CH₃ |
| —CF₃ | —C₆H₅SO₂NH₂ | 7-F, 8-CH₃ |
| —CF₃ | —C₆H₅SO₂NH₂ | 7,8-F |
| —CF₃ | —C₆H₅SO₂NH₂ | 8-SCH₃ |
| —CF₃ | —C₆H₅SO₂NH₂ | 7-F, 8-SCH₃ |
| —CF₃ | —C₆H₅SO₂NH₂ | 8-SOCH₃ |
| —CF₃ | —C₆H₅SO₂NH₂ | 7-F, 8-SOCH₃ |
| —CF₃ | —C₆H₅SO₂NH₂ | 7-F, 8-CH₃ |
| —CF₃ | —thienylSO₂NH₂ | 7-F, 8-OCH₃ |
| —CF₃ | —C₆H₅F | 8-SO₂NH₂ |
| —CF₃ | —C₆H₅Cl | 8-SO₂NH₂ |
| —CF₃ | —C₆H₅OCH₃ | 8-SO₂NH₂ |
| —CF₃ | —C₆H₅CH₃ | 8-SO₂NH₂ |
| —CF₃ | —C₆H₅SOCH₃ | 8-SO₂NH₂ |

TABLE XIII-continued

General Structure Im

| R¹ | R² | R⁴ |
|---|---|---|
| —CF₃ | —C₆H₅SO₂NH₂ | 8-Cl |
| —CF₃ | —C₆H₅SO₂NH₂ | 9-Cl |

TABLE XIV

General Structure In

| B | R² |
|---|---|
| Cl-[furan] | —C₆H₅SO₂CH₃ |
| Cl-[thiophene] | —C₆H₅SO₂CH₃ |
| Cl-[oxazole, O-N] | —C₆H₅SO₂CH₃ |
| Cl-[oxazole, N-O] | —C₆H₅SO₂CH₃ |
| Cl-[thiazole, N-S] | —C₆H₅SO₂CH₃ |
| Cl-[imidazole, N-NH] | —C₆H₅SO₂CH₃ |
| [pyrazole, N-NH] | —C₆H₅SO₂CH₃ |
| [isoxazole, N-O] | —C₆H₅SO₂CH₃ |
| [isothiazole, N-S] | —C₆H₅SO₂CH₃ |
| Cl-[pyrrole, NH] | —C₆H₅SO₂CH₃ |
| Cl-[furan] | —C₆H₅SO₂NH₂ |
| Cl-[thiophene] | —C₆H₅SO₂NH₂ |
| Cl-[oxazole, O-N] | —C₆H₅SO₂NH₂ |

TABLE XIV-continued

General Structure In

| B | R² |
|---|---|
| Cl-[thiazole, N-S] | —C₆H₅SO₂NH₂ |
| Cl-[imidazole, N-NH] | —C₆H₅SO₂NH₂ |
| [pyrazole, N-NH] | —C₆H₅SO₂NH₂ |
| [isoxazole, N-O] | —C₆H₅SO₂NH₂ |
| [isothiazole, N-S] | —C₆H₅SO₂NH₂ |
| Cl-[pyrrole, NH] | —C₆H₅SO₂NH₂ |
| Cl-[pyrrole, NH] | —C₆H₅SO₂NH₂ |

TABLE XV

General Structure Io

| R¹ | R² | R⁴ |
|---|---|---|
| —CF₃ | —C₆H₅SO₂CH₃ | H |
| —CF₂H | —C₆H₅SO₂CH₃ | H |
| —CF₂Cl | —C₆H₅SO₂CH₃ | H |
| —CF₂CF₃ | —C₆H₅SO₂CH₃ | H |
| —CO₂H | —C₆H₅SO₂CH₃ | H |
| —CO₂CH₃ | —C₆H₅SO₂CH₃ | H |
| —CO₂C₂H₅ | —C₆H₅SO₂CH₃ | H |
| —CONH₂ | —C₆H₅SO₂CH₃ | H |
| —CONHCH₃ | —C₆H₅SO₂CH₃ | H |
| —CONH(C₆H₅) | —C₆H₅SO₂CH₃ | H |
| —CON(CH₃)₂ | —C₆H₅SO₂CH₃ | H |
| —CON(C₂H₅)₂ | —C₆H₅SO₂CH₃ | H |
| —CON(CH₃)(C₂H₅) | —C₆H₅SO₂CH₃ | H |
| —CON(CH₃)(C₆H₅) | —C₆H₅SO₂CH₃ | H |
| —C(O)—N(pyrrolidinyl) | —C₆H₅SO₂CH₃ | H |
| —C(O)—N(piperidinyl) | —C₆H₅SO₂CH₃ | H |
| —CN | —C₆H₅SO₂CH₃ | H |
| —CH₂OH | —C₆H₅SO₂CH₃ | H |
| —CH₂OCH₃ | —C₆H₅SO₂CH₃ | H |
| —CH₂OC₂H₅ | —C₆H₅SO₂CH₃ | H |
| —CH₂OC₆H₅ | —C₆H₅SO₂CH₃ | H |

TABLE XV-continued

General Structure Io

| R¹ | R² | R⁴ |
|---|---|---|
| —CH₂SCH₃ | —C₆H₅SO₂CH₃ | H |
| —CH₂SC₂H₅ | —C₆H₅SO₂CH₃ | H |
| —CH₂SC₆H₅ | —C₆H₅SO₂CH₃ | H |
| —CH₂SOCH₃ | —C₆H₅SO₂CH₃ | H |
| —CH₂SOC₂H₅ | —C₆H₅SO₂CH₃ | H |
| —CH₂SOC₆H₅ | —C₆H₅SO₂CH₃ | H |
| —CH₂SO₂CH₃ | —C₆H₅SO₂CH₃ | H |
| —CH₂SO₂C₂H₅ | —C₆H₅SO₂CH₃ | H |
| —CH₂SO₂C₆H₅ | —C₆H₅SO₂CH₃ | H |
| —CF₃ | —C₆H₅SO₂CH₃ | 7-F |
| —CF₃ | —C₆H₅SO₂CH₃ | 8-F |
| —CF₃ | —C₆H₅SO₂CH₃ | 9-F |
| —CF₃ | —C₆H₅SO₂CH₃ | 8-Cl |
| —CF₃ | —C₆H₅SO₂CH₃ | 9-Cl |
| —CF₃ | —C₆H₅SO₂CH₃ | 8,9-(OCH₂O)— |
| —CF₃ | —C₆H₅SO₂CH₃ | 8-N(CH₃)₂ |
| —CF₃ | —C₆H₅SO₂CH₃ | 8-OCH₃ |
| —CF₃ | —C₆H₅SO₂CH₃ | 7-F, 8-OCH₃ |
| —CF₃ | —C₆H₅SO₂CH₃ | 7-Cl, 8-OCH₃ |
| —CF₃ | —C₆H₅SO₂CH₃ | 8-Cl, 7-F |
| —CF₃ | —C₆H₅SO₂CH₃ | 8-CH₃ |
| —CF₃ | —C₆H₅SO₂CH₃ | 7-F, 8-CH₃ |
| —CF₃ | —C₆H₅SO₂CH₃ | 7,8-F |
| —CF₃ | —C₆H₅SO₂CH₃ | 8-SCH₃ |
| —CF₃ | —C₆H₅SO₂CH₃ | 7-F, 8-SCH₃ |
| —CF₃ | —C₆H₅SO₂CH₃ | 8-SOCH₃ |
| —CF₃ | —C₆H₅SO₂CH₃ | 7-F, 8-SOCH₃ |
| —CF₃ | —C₆H₅SO₂CH₃ | 7-F, 8-CH₃ |
| —CF₃ | —C₆H₅F | 8-SO₂CH₃ |
| —CF₃ | —C₆H₅Cl | 8-SO₂CH₃ |
| —CF₃ | —C₆H₅OCH₃ | 8-SO₂CH₃ |
| —CF₃ | —C₆H₅CH₃ | 8-SO₂CH₃ |
| —CF₃ | —C₆H₅SOCH₃ | 8-SO₂CH₃ |
| —CF₃ | —C₆H₅SO₂NH₂ | H |
| —CF₂H | —C₆H₅SO₂NH₂ | H |
| —CF₂Cl | —C₆H₅SO₂NH₂ | H |
| —CF₂CF₃ | —C₆H₅SO₂NH₂ | H |
| —CO₂H | —C₆H₅SO₂NH₂ | H |
| —CO₂CH₃ | —C₆H₅SO₂NH₂ | H |
| —CO₂C₂H₅ | —C₆H₅SO₂NH₂ | H |
| —CONH₂ | —C₆H₅SO₂NH₂ | H |
| —CONHCH₃ | —C₆H₅SO₂NH₂ | H |
| —CONH(C₆H₃) | —C₆H₅SO₂NH₂ | H |
| —CON(CH₃)₂ | —C₆H₅SO₂NH₂ | H |
| —CON(C₂H₅)₂ | —C₆H₅SO₂NH₂ | H |
| —CON(CH₃)(C₂H₅) | —C₆H₅SO₂NH₂ | H |
| —CON(CH₃)(C₆H₅) | —C₆H₅SO₂NH₂ | H |
| $-\overset{O}{\underset{\|}{C}}-N\text{(pyrrolidine)}$ | —C₆H₅SO₂NH₂ | H |
| $-\overset{O}{\underset{\|}{C}}-N\text{(piperidine)}$ | —C₆H₅SO₂NH₂ | H |
| —CN | —C₆H₅SO₂NH₂ | H |
| —CH₂OH | —C₆H₅SO₂NH₂ | H |
| —CH₂OCH₃ | —C₆H₅SO₂NH₂ | H |
| —CH₂OC₂H₅ | —C₆H₅SO₂NH₂ | H |
| —CH₂OC₆H₅ | —C₆H₅SO₂NH₂ | H |
| —CH₂SCH₃ | —C₆H₅SO₂NH₂ | H |
| —CH₂SC₂H₅ | —C₆H₅SO₂NH₂ | H |
| —CH₂SC₆H₅ | —C₆H₅SO₂NH₂ | H |
| —CH₂SOCH₃ | —C₆H₅SO₂NH₂ | H |
| —CH₂SOC₂H₅ | —C₆H₅SO₂NH₂ | H |
| —CH₂SOC₆H₅ | —C₆H₅SO₂NH₂ | H |
| —CH₂SO₂CH₃ | —C₆H₅SO₂NH₂ | H |
| —CH₂SO₂C₂H₅ | —C₆H₅SO₂NH₂ | H |
| —CH₂SO₂C₆H₅ | —C₆H₅SO₂NH₂ | H |
| —CF₃ | —C₆H₅SO₂NH₂ | 7-F |
| —CF₃ | —C₆H₅SO₂NH₂ | 8-F |
| —CF₃ | —C₆H₅SO₂NH₂ | 9-F |
| —CF₃ | —C₆H₅SO₂NH₂ | 8-Cl |
| —CF₃ | —C₆H₅SO₂NH₂ | 9-Cl |
| —CF₃ | —C₆H₅SO₂NH₂ | 7,8-(OCH₂O)— |
| —CF₃ | —C₆H₅SO₂NH₂ | 8-N(CH₃)₂ |
| —CF₃ | —C₆H₅SO₂NH₂ | 8-OCH₃ |
| —CF₃ | —C₆H₅SO₂NH₂ | 7-F, 8-OCH₃ |
| —CF₃ | —C₆H₅SO₂NH₂ | 7-Cl, 8-OCH₃ |
| —CF₃ | —C₆H₅SO₂NH₂ | 8-Cl, 7-F |
| —CF₃ | —C₆H₅SO₂NH₂ | 8-CH₃ |
| —CF₃ | —C₆H₅SO₂NH₂ | 7-F, 8-CH₃ |
| —CF₃ | —C₆H₅SO₂NH₂ | 7,8-F |
| —CF₃ | —C₆H₅SO₂NH₂ | 8-SCH₃ |
| —CF₃ | —C₆H₅SO₂NH₂ | 7-F, 8-SCH₃ |
| —CF₃ | —C₆H₅SO₂NH₂ | 8-SOCH₃ |
| —CF₃ | —C₆H₅SO₂NH₂ | 7-F, 8-SOCH₃ |
| —CF₃ | —C₆H₅SO₂NH₂ | 7-F, 8-CH₃ |
| —CF₃ | —thienylSO₂NH₂ | 7-F, 9OCH₃ |
| —CF₃ | —C₆H₅F | 8-SO₂NH₂ |
| —CF₃ | —C₆H₅Cl | 8-SO₂NH₂ |
| —CF₃ | —C₆H₅OCH₃ | 8-SO₂NH₂ |
| —CF₃ | —C₆H₅CH₃ | 8-SO₂NH₂ |
| —CF₃ | —C₆H₅SOCH₃ | 8-SO₂NH₂ |

TABLE XVI

General Structure Ip

| B | R² |
|---|---|
| 2-chloro-furan (Cl on furan) | —C₆H₅SO₂CH₃ |
| 2-chloro-thiophene | —C₆H₅SO₂CH₃ |
| 2-chloro-oxazole | —C₆H₅SO₂CH₃ |
| 2-chloro-isoxazole | —C₆H₅SO₂CH₃ |
| 2-chloro-thiazole | —C₆H₅SO₂CH₃ |
| 2-chloro-imidazole (NH) | —C₆H₅SO₂CH₃ |
| pyrazole (NH) | —C₆H₅SO₂CH₃ |
| isoxazole | —C₆H₅SO₂CH₃ |
| isothiazole | —C₆H₅SO₂CH₃ |

TABLE XVI-continued

General Structure Ip

| B | R² |
|---|---|
| 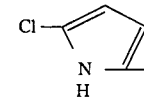 | —C₆H₅SO₂CH₃ |
| 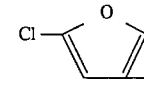 | —C₆H₅SO₂NH₂ |
| 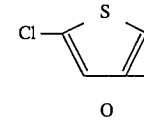 | —C₆H₅SO₂NH₂ |
| 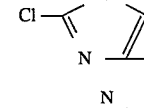 | —C₆H₅SO₂NH₂ |
| 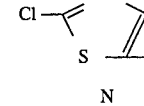 | —C₆H₅SO₂NH₂ |
| 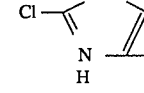 | —C₆H₅SO₂NH₂ |
| 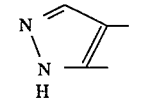 | —C₆H₅SO₂NH₂ |
| 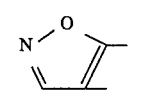 | —C₆H₅SO₂NH₂ |
| 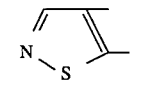 | —C₆H₅SO₂NH₂ |
| 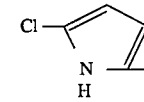 | —C₆H₅SO₂NH₂ |
| 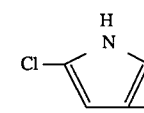 | —C₆H₅SO₂NH₂ |

Within Formula I there is a subclass of compounds of high interest represented by Formula II:

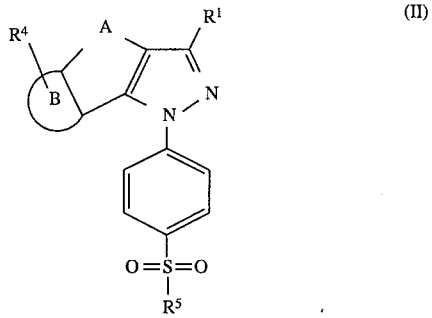

(II)

wherein A is —(CH₂)$_m$—X—(CH₂)$_n$—;

wherein X is S(O)$_p$ or O;

wherein m is 0 or 1;

wherein n is 0 or 1;

wherein p is 0 or 1;

wherein B is selected from aryl and heteroaryl;

wherein R¹ is selected from haloalkyl, aminocarbonyl, alkoxycarbonyl and cyano;

wherein R⁴ is one or more radicals selected from hydrido, halo, alkyl and alkoxy; and wherein R⁵ is selected from alkyl and amino;

or a pharmaceutically-acceptable salt thereof.

A preferred class of compounds consists of those compounds of Formula II wherein A is —(CH₂)$_m$—X—(CH₂)$_n$—; wherein X is S(O)$_p$ or O; wherein m is 0 or 1; wherein n is 0 or 1; wherein p is 0 or 1; wherein B is selected from phenyl and five membered heteroaryl; wherein R¹ is selected from lower haloalkyl, aminocarbonyl, lower alkoxycarbonyl and cyano; wherein R⁴ is one or more radicals selected from hydrido, halo, lower alkyl and lower alkoxy; and wherein R⁵ is selected from lower alkyl and amino; or a pharmaceutically-acceptable salt thereof.

A class of compounds of particular interest consists of those compounds of Formula II wherein A is —(CH₂)$_m$—X—(CH₂)$_n$—; wherein X is S(O)$_p$ or O; wherein m is 0 or 1; wherein n is 0 or 1; wherein p is 0 or 1; wherein B is selected from phenyl, thienyl, furyl and pyrrolyl; wherein R¹ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, aminocarbonyl, methoxycarbonyl, ethoxycarbonyl, propoxycarbonyl, butoxycarbonyl and cyano; wherein R⁴ is one or more radicals selected from hydrido, fluoro, chloro, bromo, methyl, ethyl, isopropyl, tert-butyl, isobutyl, hexyl, methoxy, methylenedioxy, ethoxy, propoxy, n-butoxy and tert-butoxy; and wherein $R^5$ is selected from methyl and amino; or a pharmaceutically-acceptable salt thereof.

A family of specific compounds of particular interest within Formula II consists of compounds and pharmaceutically-acceptable salts thereof as follows:

4-[7-chloro-1,5-dihydro-3-trifluoromethylthieno[3',2':4,5]thiopyrano-s-oxide[3,2-c]pyrazol-1-yl]benzenesulfonamide;

methyl [1-(4-aminosulfonylphenyl) -1,5-dihydro-7-fluoro-3-(trifluoromethyl)-[2]benzothiopyrano[4,3-c]pyrazol-3-yl]carboxylate;

[1-(4-aminosulfonylphenyl)-1,5-dihydro-7-fluoro-3-(trifluoromethyl)-[2]benzothiopyrano [4,3-c]pyrazol-3-yl] carboxamide;

4-[1,5-dihydro -6-fluoro -7-methoxy-3-(difluoromethyl)-[2]benzothiopyrano [4,3-c]pyrazol-1-yl]benzenesulfonamide;

4-[1,5-dihydro-7-fluoro-3-(trifluoromethyl)-[2]benzothiopyrano[4,3-c]pyrazol-1-yl]benzenesulfonamide;

4-[1,5-dihydro-6-fluoro-7-methoxy-3-(trifluoromethyl)-[2]benzothiopyrano[4,3-c]pyrazol-1-yl]benzenesulfonamide;

1,5-dihydro-6-fluoro-7-methoxy-1-[4-(methylsulfonyl)phenyl]- 3-(trifluoromethyl)-[2]benzothiopyrano[4,3-c]pyrazole;

4-[1,4-dihydro-3-(trifluoromethyl)-[1]benzopyrano[4,3-c]pyrazol-1-yl]benzenesulfonamide;

methyl [1-[4-(aminosulfonyl)phenyl]-1,4-dihydro-[1]benzopyrano[4,3-c]pyrazol-3-yl]carboxylate;

4-[1,4-dihydro-6-fluoro-3-(trifluoromethyl)-[1]benzopyrano[4,3-c]pyrazol-1-yl]benzenesulfonamide;

4-[3-(trifluoromethyl)-1H-benzofuro[3,2-c]pyrazol-1-yl]benzenesulfonamide;

4-[1,4-dihydro-3-(trifluoromethyl)-[1]benzothiopyrano[4,3-c]pyrazol-1-yl]benzenesulfonamide;

methyl [1-[4-(aminosulfonyl)phenyl]-1,4-dihydro-[1]benzothiopyrano[4,3-c]pyrazol-3-carboxylate;

4-[6,7-dichloro-1,4-dihydro-3-(trifluoromethyl)-[1]benzothiopyrano[4,3-c]pyrazol-1-yl]benzenesulfonamide;

4-[1,4-dihydro-7-fluoro-3-(trifluoromethyl)-[1]benzothiopyrano[4,3-c]pyrazol-1-yl]benzenesulfonamide;

4-[1,4-dihydro-6-isopropyl-3-(trifluoromethyl)-[1]benzothiopyrano[4,3-c]pyrazol-1-yl]benzenesulfonamide;

4-[1,4-dihydro-7,8-dimethoxy-3-(trifluoromethyl)-[1]benzothiopyrano[4,3-c]pyrazol-1-yl]benzenesulfonamide;

4-[1,4-dihydro-7-methoxy-3-(trifluoromethyl)-[1]benzothiopyrano[4,3-c]pyrazol-1-yl]benzenesulfonamide;

4-[1,4-dihydro-7-methyl-3-(trifluoromethyl)-[1]benzothiopyrano[4,3-c]pyrazol-1-yl]benzenesulfonamide;

4-[7-chloro-1,4-dihydro-3-(trifluoromethyl)-[1]benzothiopyrano[4,3-c]pyrazol-1-yl]benzenesulfonamide;

4-[1,5-dihydro-3-(trifluoromethyl)-[2]benzothiopyrano[4,3-c]pyrazol-1-yl]benzenesulfonamide;

4-[1,5-dihydro-7-methyl-3-(trifluoromethyl)-[2]benzothiopyrano[4,3-c]pyrazol-1-yl]benzenesulfonamide;

1,5-dihydro -1-[4-(methylsulfonyl)phenyl]-7-methyl- 3-(trifluoromethyl)-[2]benzothiopyrano[4,3-c]pyrazole;

4-[7-chloro-1,5-dihydro-3-(trifluoromethyl)-[2]benzothiopyrano[4,3-c]pyrazol-1-yl]benzenesulfonamide;

4-[1,5-dihydro-7-methoxy-3-(trifluoromethyl)-[2]benzothiopyrano[4,3-c]pyrazol-1-yl]benzenesulfonamide;

4-[7-chloro-1,5-dihydro-3-trifluoromethyl-[2]thienothiopyrano[4,3-c]pyrazol-1-yl]benzenesulfonamide; and 4-[3-cyano-1,4-dihydro[1]benzothiopyrano[4,3-c]pyrazol-1-yl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide "haloalkoxy" or haloalkoxyalkyl radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Such heterocyclic radicals preferrably include ring systems having 3 to 10 members. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.]tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.]etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.]and isothiazolyl; unsaturated condensed heterocyclic group containing 1 to 2 sulfur atoms and 1 to 3 nitrogen atoms [e.g., benzothiazolyl, benzothiadiazolyl, etc.]and the like. The term also embraces radicals where heterocyclic radicals are fused with aryl radicals. Examples of such fused bicyclic radicals include benzofuryl, benzothienyl, and the like. Said "heterocyclic" radicals may have 1 to 3 substituents such as lower alkyl, hydroxy, oxo, amino and lower alkylamino. More preferred heteroaryl radicals include five to six membered heteroaryl radicals. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl. The term "arylthio" embraces radicals containing an aryl radical, attached to a divalent sulfur atom, such as a phenylthio radical. The term "alkylsulfinyl" embraces radicals containing a linear or branched alkyl radical, of one to ten carbon atoms, attached to a divalent —S(=O)-radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "alkylsulfinylalkyl" embraces alkylsulfinyl radicals attached to an alkyl radical, where alkyl and alkylsulfinyl are defined as above. More preferred alkylsulfinylalkyl radicals are "lower alkylsulfinylalkyl" radicals having one to six carbon atoms. Examples of such lower alkylsulfinylalkyl radicals include methylsulfinylmethyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The term "alkylsulfonylalkyl" embraces alkylsulfonyl radicals attached to an alkyl radical, where alkyl and alkylsulfonyl are defined as above. More preferred alkylsulfonylalkyl radicals are "lower alkylsulfonylalkyl" radicals having one to six carbon atoms. Examples of such lower alkylsulfonylalkyl radicals include methylsulfonylmethyl, ethylsulfonylmethyl and propylsulfonylmethyl. The term "arylsulfonyl" embraces aryl radicals as defined above, attached to a sulfonyl radical. Examples of such radicals include phenylsulfonyl. The terms "sulfamyl", "aminosulfonyl" and "sulfonamidyl" denotes $NH_2O_2S$—. The terms "N-alkylsulfamyl" and "N,N-dialkylsulfamyl" denote sulfamyl radicals substituted, respectively, with one alkyl radical, a cycloalkyl ring, or two alkyl radicals. The terms "N-arylsulfamyl" and "N-alkyl-N-arylsulfamyl" denote sulfamyl radicals substituted with one aryl radical or one alkyl and one aryl radical, respectively. The term "acyl" denotes a radical provided by the residue after removal of hydroxyl from an organic acid. Examples of such acyl radicals include formyl, alkanoyl and aroyl radicals. The terms "carboxy" or "carboxyl", whether used alone or with other terms, such as "carboxyalkyl", denotes —$CO_2H$. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "alkylcarbonyl" includes radicals having alkyl, aryl and aralkyl radicals, respectively, as defined above, attached via an oxygen atom to a carbonyl radical. More preferred alkylcarbonyl radicals are "lower alkylcarbonyl" radicals having one to six carbon atoms. Examples of such radicals include methylcarbonyl and ethylcarbonyl. The term "alkylcarbonylalkyl" embraces radicals having "alkylcarbonyl", as defined above substituted to an alkyl radical. More preferred alkylcarbonylalkyl radicals are "lower alkylcarbonylalkyl" having lower alkylcarbonyl radicals as defined above attached to one to six carbon atoms. Examples of such lower alkylcarbonylalkyl radicals include methylcarbonylmethyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl. The terms "alkanoyl" or "carboxyalkyl" embrace radicals having a carboxy radical as defined above, attached to an alkyl radical. The alkanoyl radicals may be substituted or unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "alkylaminocarbonyl" embraces alkylamino radicals, as described above, attached to a carbonyl radical. More preferred alkylaminocarbonyl radicals are "lower alkylaminocarbonyl" having lower alkylamino radicals, as described above, attached to a carbonyl radical. Examples of such radicals include N-methylaminocarbonyl and N,N-dimethylcarbonyl. The term "arylamino" denotes amino groups which have been substituted with one or two aryl radicals, such as N-phenylamino. The "arylamino" radicals may be further substituted on the aryl ring portion of the radical. The term "arylaminocarbonyl" embraces arylamino radicals, as described above, connected to a carbonyl radical. An example of such radicals includes phenylaminocarbonyl. The term "N-alkyl-N-arylaminocarbonyl" embraces arylamino radicals, as described above, to a carbonyl radical. An example of such radicals includes phenylaminocarbonyl. The term "aminocarbonyl" denotes an amide group of the formula —C(=O)NH$_2$. The term "N-alkyl-N-arylaminocarbonyl" embraces aminocarbonyl radicals, as described above, substituted with one alkyl and one aryl radical. An example of such radicals is N-methyl-N-phenylaminocarbonyl. The term "aminocarbonylalkyl" denotes an aminocarbonyl radical attached to an alkyl radical, as described above. An example of such radicals is aminocarbonylmethyl. The term "amidino" denotes an —C(=NH)—NH$_2$ radical. The term "cyanoamidino" denotes an —C(=N—CN)—NH$_2$ radical. The term "cycloalkyl" embraces radicals having three to ten carbon atoms, such as cyclopropyl cyclobutyl, cyclopentyl, cyclohexyl and cycloheptyl. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino (CH$_3$C(=O)—NH—).

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable.

Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–XII, wherein the R$^1$–R$^5$ substituents are as defined for Formulas I–II, above, except where further noted.

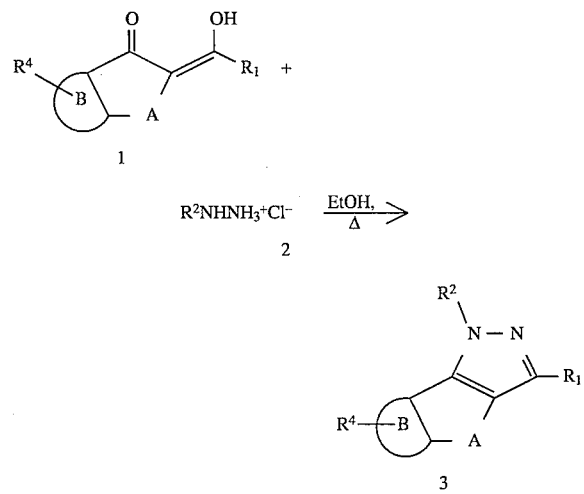

Synthetic Scheme I illustrates the procedure used to prepare the antiinflammatory pyrazoles 3 of the present invention. 1,3-Dicarbonyl compounds such as 1, or the shown enol form which is in equilibrium to the diketone, are reacted with a hydrazine hydrochloride 2 in warm ethanol to provide the pyrazoles 3 via a condensation reaction.

SCHEME II

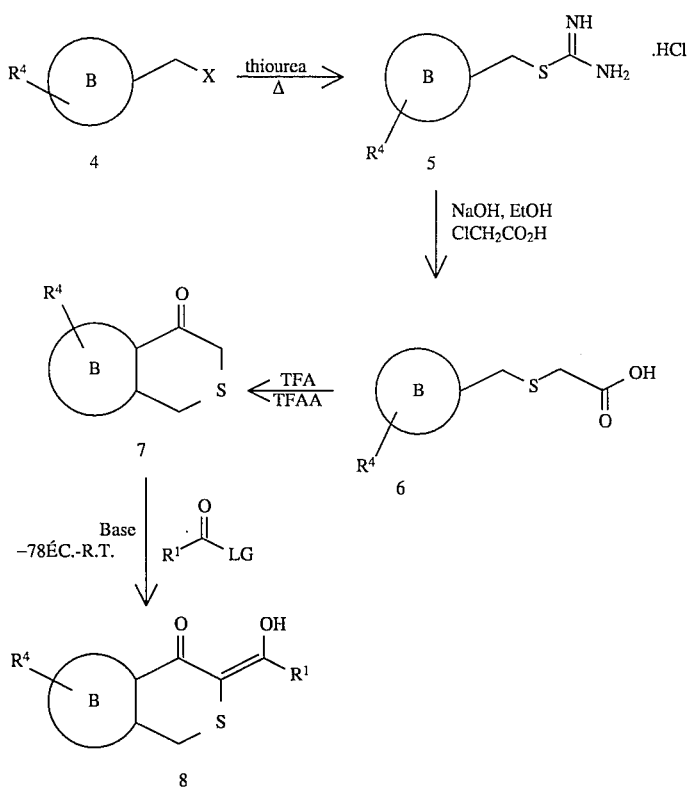

Synthetic Scheme II illustrates the four step procedure for the preparation of substituted diketones 8. In step one, an appropriately substituted methyl halide 4 (where X is chloro for example) is converted into the corresponding thiouronium salt 5 upon treatment with thiourea. In step two, the thiouronium salt 5 is converted according to the procedure of Lumma and Berchtold (*J. Org. Chem.*, 34, 1566 (1969)) to the free mercaptide and then trapped with chloroacetic acid or a related salt to provide the acetic acid derivatives 6. In step three, the acids 6 are reacted with trifluoroacetic anhydride (TFAA) in trifluoroacetic acid (TFA) to give the ketones 7. In step four, the ketones 7 are first treated with base, such as sodium methoxide or lithium diisopropylamide (LDA), followed by condensation with a suitable acylating agent, $R^1$COLG, (where LG represents an appropriate leaving group such as methoxy, chloro, imidazole and the like) in an appropriate solvent, such as methanol, diethyl ether or tetrahydrofuran, to provide the desired diketones 8 which are suitable for conversion into antiinflammatory pyrazoles as illustrated in Scheme I.

SCHEME III

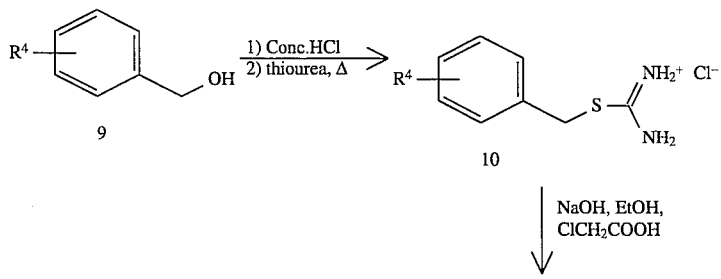

-continued
SCHEME III

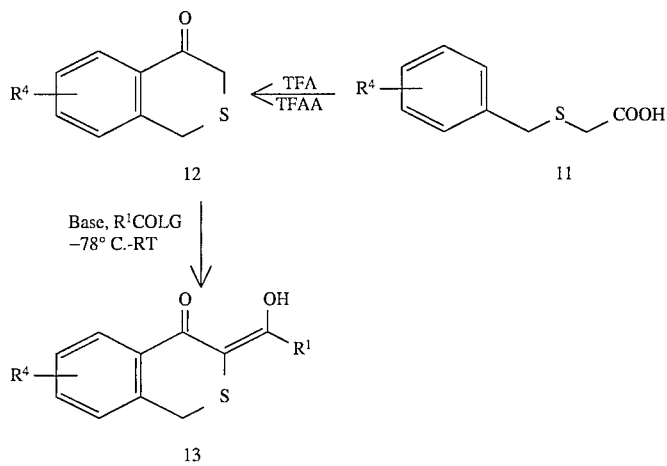

Synthetic Scheme III illustrates the four step procedure for the preparation of substituted isothiochromanone 1,3-carbonyl derivatives 13. In step one, an appropriately substituted benzyl alcohol 9 is converted into the corresponding benzyl chloride by stirring with concentrated hydrochloric acid and then immediately converted into a thiouronium salt 10 upon treatment with thiourea at reflux. In step two, the thiouronium salt is converted to the free mercaptide and then trapped with chloroacetic acid or a related salt to provide the acetic acid derivatives 11. In step three, the acids 11 are reacted with trifluoroacetic anhydride (TFAA) in trifluoroacetic acid (TFA) to give the isothiochromanone products 12. In step four, the isothiochromanones 12 are first treated with base, such as sodium methoxide, sodium bistrimethylsilylamide or lithium diisopropylamide (LDA), followed by condensation with a suitable acylating agent, $R^1COLG$, (where LG is defined as in Scheme II) in an appropriate solvent, such as methanol, diethyl ether or tetrahydrofuran, to provide 1,3-dicarbonyl compounds 13 which are suitable for conversion into antiinflammatory pyrazoles as illustrated in Scheme I.

Alternatively, the dicarbonyl compounds 13 can be directly prepared from commercially available isothiochromanones 12. The thiouronium salts 10 can be prepared from commercially available benzyl halides.

Synthetic Scheme IV illustrates a three step procedure used for the preparation of substituted thiochromanone 1,3-dicarbonyl derivatives 17. In step one, an appropriate substituted thiophenol 14 is converted into the corresponding propionic acid derivatives 15 upon treatment with acrylic acid at a temperature in a range of room temperature to about 50° C. In step two, the propionic acids 15 are subjected to treatment with a mixture of trifluoroacetic anhydride and trifluoroacetic acid to effect intramolecular Friedel-Crafts acylation, thus providing thiochromanones 16. In the last step, substituted thiochromanones 16 are first treated with a base, such as lithium diisopropyl amide or sodium methoxide (LDA), followed by condensation with suitable acylating agents $R^1COLG$ (as defined in Scheme II) in an appropriate solvent such as diethylether, methanol or tetrahydrofuran to provide the 1,3-dicarbonyl compounds 17 which are suitable for conversion into antiinflammatory pyrazoles as illustrated in Scheme I.

Alternatively, the dicarbonyl compounds 17 can be directly prepared from commercially available thio-4-chromanones 16.

SCHEME IV

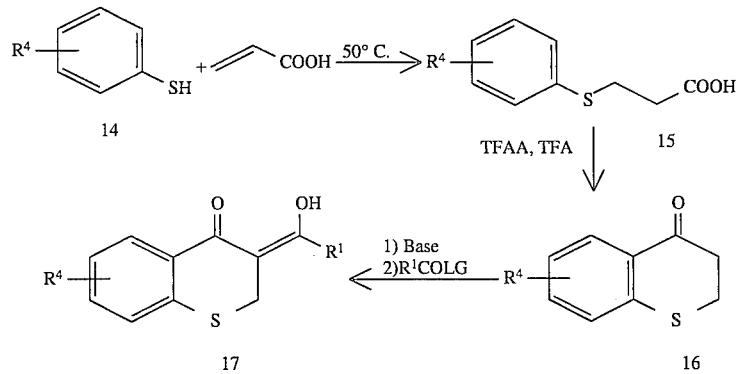

SCHEME V

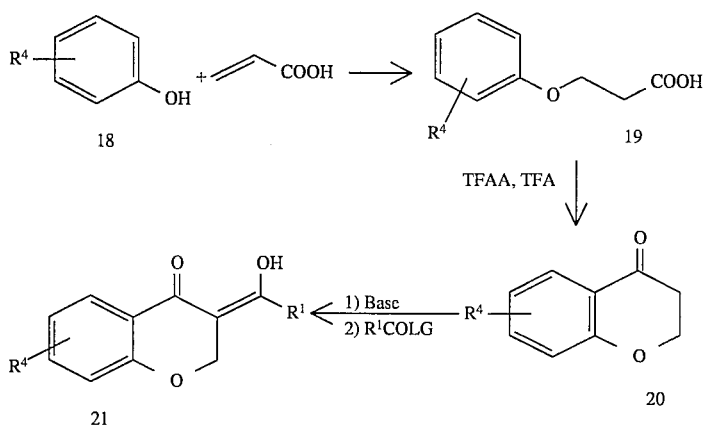

Synthetic Scheme V details the three step procedure used to prepare substituted 1,3-dicarbonyl chromanone derivatives 21. In step one, substituted phenols 18 are condensed with acrylic acid to afford 3-phenoxypropionic acids 19. In step two, the acids 19 are treated with a mixture of trifluoroacetic anhydride and trifluoroacetic acid to affect intramolecular Friedel-Crafts acylation affording selected chromanones 20. In step three, substituted chromanones 20 are first treated with base, such as lithiumdiisopropylamide (LDA) or sodium methoxide followed by condensation with suitable acylating agents, $R^1$CO-LG (where LG represents leaving group as previously defined in Scheme II in an appropriate solvent such as diethyl ether or methanol) to provide 1,3-dicarbonyl compounds 21 which are suitable for conversion into antiinflammatory pyrazoles as illustrated in Scheme I.

Alternatively, the dicarbonyl compounds 21 can be directly formed from commercially available chromanones 20.

of trifluoroacetic acid and trifluoroacetic anhydride to promote intramolecular Friedel-Crafts acylation affording isochromanone 24 derivatives. In the third step, the isochromanones 24 are first treated with a base such as lithium diisopropylamide (LDA) or sodium methoxide followed by condensation with suitable acylating agents ($R^1$COLG) to provide the 1,3-dicarbonyl compounds 25 which were suitable for conversion into antiinflammatory pyrazoles as illustrated in Scheme I.

SCHEME VI

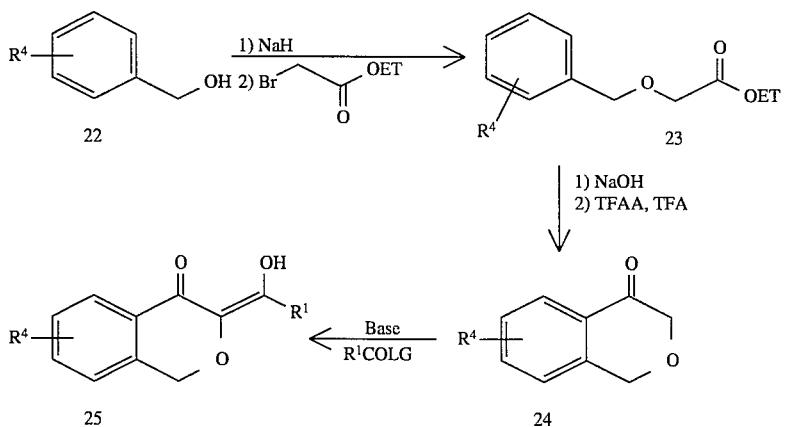

Synthetic Scheme VI illustrates a three step procedure used to prepare substituted 1,3-dicarbonyl isochromanone derivatives 25. In step one, selected benzyl alcohol derivatives 22 are treated with sodium hydride and subsequently treated with ethyl bromoacetate to provide the desired ethers 23. In step two, the ester group of 23 is hydrolyzed with aqueous sodium hydroxide and then treated with a mixture

SCHEME VII

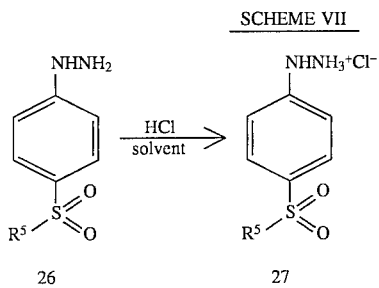

Synthetic Scheme VII illustrates a procedure used to prepare the methylsulfonylphenylhydrazine hydrochloride and the sulfonamidylphenylhydrazine hydrochlorides 27 as used in Scheme I. The sulfonylphenylhydrazine 26 is converted to the hydrochloride salt by stirring with a 4N solution of hydrochloric acid in a solvent such as dioxane.

SCHEME VIII

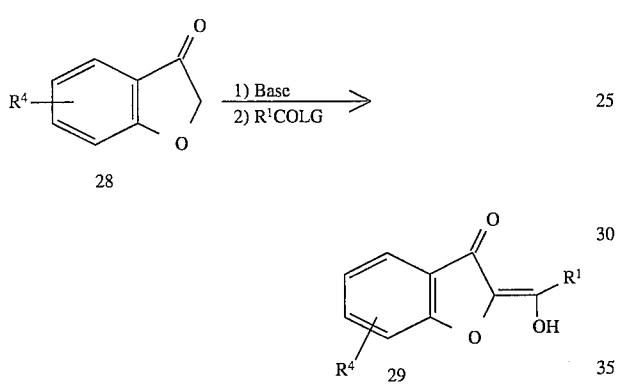

Synthetic Scheme VIII illustrates a procedure used to prepare substituted 3-coumaranones 29. Coumaranones 28 are first treated with a base, such as lithium diisopropyl amide or sodium methoxide (LDA) followed by condensation with suitable acylating agents $R^1COLG$ (as defined in Scheme II) in an appropriate solvent such as diethylether, methanol or tetrahydrofuran to provide the 1,3-dicarbonyl compounds 29 which are suitable for conversion into antiinflammatory pyrazoles as illustrated in Scheme I.

SCHEME IX

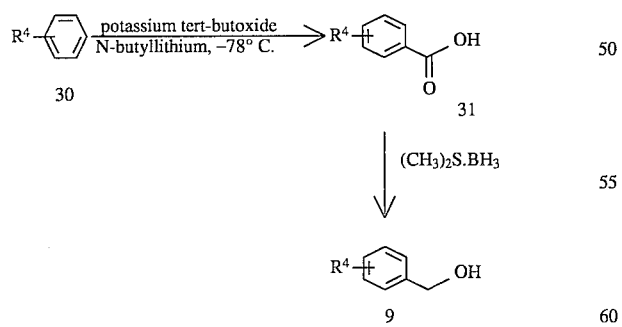

Synthetic Scheme IX illustrates a two step procedure used for the preparation of substituted benzylalcohols 9. In step one, a mixture of potassium tert-butoxide and anhydrous tetrahydrofuran, cooled to −78° C. and treated with a 1.6M solution of n-butyllithium in hexanes, is added to an appropriate substituted benzene 30 to yield the benzoic acid 31. In step two, the benzoic acid 31 is dissolved in a solvent, such as tetrahydrofuran, and treated with a reducing agent, such as borane dimethyl sulfide complex, to form the desired benzyl alcohol 9.

SCHEME X

Synthetic Scheme X illustrates a procedure used for the preparation of the antiinflammatory oxidized thio-containing fused tricyclic pyrazoles 33. The appropriate pyrazole 32 from Scheme I, where A is S or $—(CH_2)_mS(CH_2)_n—$, is treated with an oxidizing agent such as m-chloroperbenzoic acid (MCPBA) or hydrogen peroxide. Compounds having differing amounts of oxidation (sulfinyls and sulfones) can be separated, such as by chromatography.

SCHEME XI

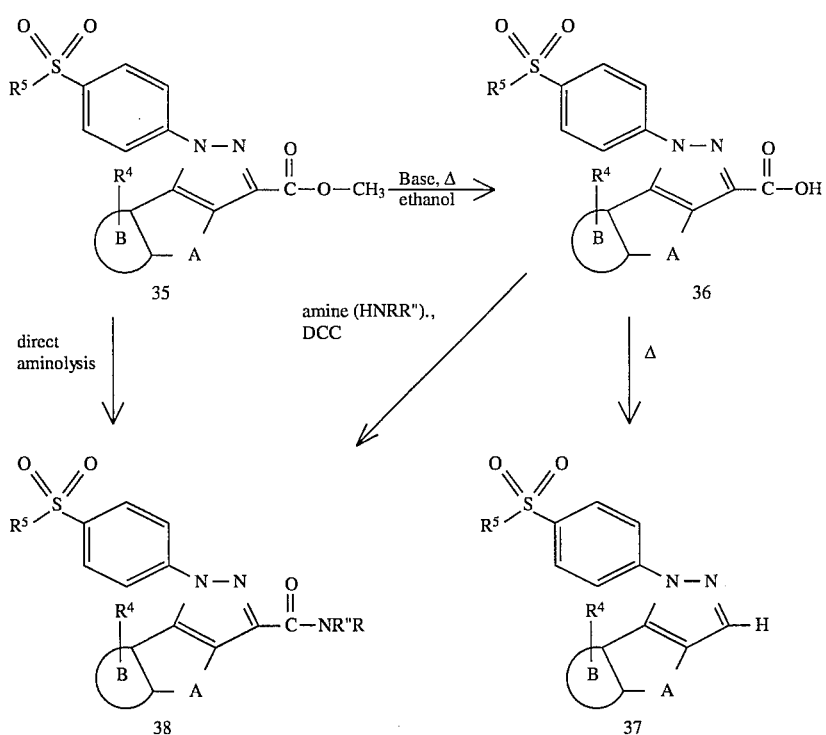

Synthetic Scheme XI shows procedures for preparing antiinflammatory agents 36, 37 and 38 of Formula I. The esters 35, which can be prepared as shown in Scheme I, is dissolved in aqueous ethanol and a base such as 10% NaOH is added. The reaction is heated to reflux to give the acids 36. The acids 36 can be converted to the fused pyrazole with a hydrido radical by decarboxylation by heating to about 290° C. to give the decarboxylated products 37. The acids 36 also can be converted to the appropriate amides 38 by dissolving in methanol and treating with an appropriate amine in the presence of a condensing agent such as dicyclohexylcarbodiimide (DCC). The amides 38 can also be prepared by direct aminolysis of 35.

SCHEME XII

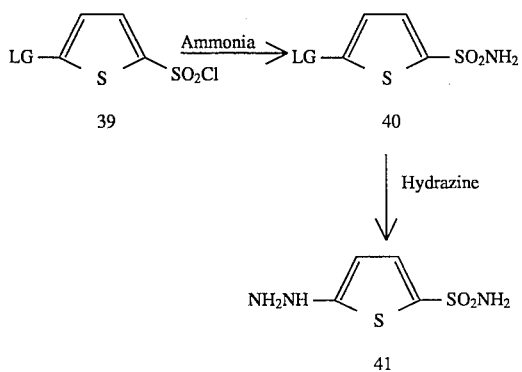

Synthetic Scheme XII shows the two step procedure for preparation of substituted heteroarylhydrazine compounds 41 as used in Scheme I where $R^2$ is thienyl. In step 1, the heteroarylsulfonyl chloride 39 (where LG represents a leaving group such as halo) is treated with ammonia to give the heteroaryl sulfonamides 40. In step 2, the heteroaryl sulfonamides 40 are treated with hydrazine to give the substituted heteroarylhydrazines 41.

The following examples contain detailed descriptions of the methods of preparation of compounds of Formula I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

4-[1,5-Dihydro-6-fluoro-7-methoxy-3-(trifluoromethyl)-[2] benzothiopyrano[4,3-c]pyrazol-1-yl]benzenesulfonamide

Step 1

Preparation of 2-fluoro-3-methoxybenzoic acid

A mixture of potassium tert-butoxide (30.80 g, 274 mmol) and anhydrous tetrahydrofuran (300 mL) was cooled to −78° C. and treated with a 1.6M solution of n-butyllithium (172 mL, 275 mmol) in hexanes. After stirring for 15 minutes, 2-fluoroanisole (31.35 g, 248 mmol) was added and the reaction was stirred an additional 1.8 hours. The reaction was poured into a 2 L Erlenmeyer flask containing dry ice and warmed to room temperature. Water (250 mL) was added and after extracting with ether (160 mL), the aqueous layer was acidified with concentrated hydrochloric acid, and filtered to give 2-fluoro-3-methoxybenzoic acid (21.43 g, 51%) as a yellow solid: mp 155°–160° C.; $^1$H NMR (acetone-$d_6$) 300 MHz 7.46 (ddd, J=6.0 Hz J=1.8 Hz J=1.4 Hz, 1H) 7.36 (dt, J=1.6 Hz J=8.1 Hz, 1H) 7.20 (dt, J=1.4 Hz J=8.1 Hz, 1H) 3.92 (s, 3H); $^{19}$F NMR (acetone-$d_6$) 300 MHz –134.04 (m). Mass spectrum: M+H=171.

Step 2

Preparation of 2-fluoro-3-methoxybenzyl alcohol

2-Fluoro-3-methoxybenzoic acid from Step 1 (16.65 g, 98 mmol) was dissolved in anhydrous tetrahydrofuran (60 mL), cooled in an ice bath, and treated with borane dimethyl sulfide complex (19 mL, 190 mmol). The reaction was stirred at room temperature for 4.2 hours, quenched by the slow addition of methanol, and concentrated in vacuo. The residue was dissolved in ethyl acetate, treated with 3N hydrochloric acid and filtered through diatomaceous earth. The organic layer of the filtrate was collected, washed with NaHCO$_3$, brine, dried over MgSO$_4$ and reconcentrated in vacuo to give 2-fluoro-3-methoxybenzyl alcohol (12.35 g, 81%) as a white solid: mp 53°–57° C.; $^1$H NMR (acetone-$d_6$) 300 MHz 7.07 (m, 3H) 4.67 (d, J=5.8 Hz, 2H) 4.24 (t, J=5.8 Hz, 1H) 3.86 (s, 3H); $^{19}$F NMR (acetone-$d_6$) 300 MHz –144.77 (m).

Step 3

Preparation of 2-fluoro-3-methoxybenzyl chloride

2-Fluoro-3-methoxybenzyl alcohol from Step 2 (12.16 g, 78 mmol) was dissolved in concentrated hydrochloric acid (60 mL) and hydrochloric acid gas was bubbled through the solution for 3 minutes. The flask was capped and the reaction stirred at room temperature (21 hours). The reaction mixture was extracted with ether, dried over MgSO$_4$ and concentrated in vacuo to give 2-fluoro-3-methoxybenzyl chloride (10.36 g, 76%) as a green oil: $^1$H NMR (acetone-$d_6$) 300 MHz 7.12 (m, 2H) 7.05 (m, 1H) 4.73 (s, 2H) 3.89 (s, 3H); $^{19}$F NMR (acetone-$d_6$) 300 MHz –142.07(m).

Step 4

Preparation of S-(2-fluoro-3-methoxybenzyl)-isothiouronium chloride

Thiourea (4.47 g, 59 mmol) was added to a solution of 2-fluoro-3-methoxybenzyl chloride from Step 3 (10.20 g, 58 mmol) in methanol (25 mL). The reaction was heated to reflux for 3.3 hours, concentrated in vacuo, triturated with ether, and filtered to give a white solid (14.65 g, 100%).

Step 5

Preparation of 3-(2-fluoro-3-methoxyphenylthio)propanoic acid

A 500 mL flask was charged with the thiouronium salt from Step 4 (14.65 g, 58 mmol), sodium chloroacetate (10.44 g, 90 mmol), ethanol (60 mL) and water (25 mL). After heating to reflux, a solution of NaOH (10.66 g, 266 mmol) in water (35 mL) was added to the reaction dropwise. After stirring for 16.6 hours, the reaction was acidified with concentrated hydrochloric acid, extracted with ether, washed with brine, dried over MgSO$_4$, concentrated in vacuo and recrystallized from ether/hexane to give a brown solid (7.70 g, 57%): mp 72°–74° C.; $^1$H NMR (CDCl$_3$) 300 MHz 7.03 (m, 1H) 6.91 (m, 2H) 3.89 (d, J=1.0 Hz, 2H) 3.88 (s, 3H) 3.19 (s, 2H); $^{19}$F NMR (CDCl$_3$) 300 MHz –140.76 (m).

Step 6

Preparation of 8-fluoro-7-methoxyisothiochroman-4-one

The acid from Step 5 (7.63 g, 33 mmol) was dissolved in trifluoroacetic acid (12 mL), treated with trifluoroacetic anhydride (4 mL) and stirred at room temperature (8 minutes). The reaction was poured into 10% Na$_2$CO$_3$ (50 mL) and extracted with ethyl acetate, washed with brine, dried over MgSO$_4$ and concentrated in vacuo to give 8-fluoro-7-methoxyisothiochroman-4-one (5.42 g, 77%) as a brown solid: mp 85°–92° C.; $^1$H NMR (CDCl$_3$) 300 MHz 7.83 (d, J=8.9 Hz, 1H) 7.19 (t, J=8.5 Hz, 1H) 4.01 (s, 2H) 3.98 (s, 3H) 3.55 (s, 2H); $^{19}$F NMR (CDCl$_3$) 300 MHz –141.24 (m).

Step 7

Preparation of 6-fluoro-7-methoxy-3-(trifluoroacetyl)-isothiochroman-4-one

8-Fluoro-7-methoxyisothiochroman-4-one from Step 6 (1.70 g, 8.0 mmol) was dissolved in anhydrous tetrahydrofuran (30 mL), cooled to –78° C., and treated with a 1.0M tetrahydrofuran solution of sodium bistrimethylsilyl amide (10 mL, 10 mmol). After 30 minutes, N-trifluoroacetylimidazole (1.85 g in 10.0 mL THF, 11.3 mmol) was added and the reaction was stirred and warmed to room temperature overnight (19.4 hours). The reaction was treated with 1N hydrochloric acid (30 mL). The organic layer was collected, washed with brine, dried over MgSO$_4$, concentrated in vacuo and recrystallized from dichloromethane/isooctane to give the diketone (1.14 g, 46%) as a brown solid: mp 162°–164° C.; $^1$H NMR (CDCl$_3$) 300 MHz 15.50 (s, 1H) 7.82 (dd, J=8.9 Hz J=1.0 Hz, 1H) 6.99 (t, J=8.5 Hz, 1H) 3.99 (s, 3H) 3.89 (s, 2H) 2.43 (s, 2H); $^{19}$F NMR (CDCl$_3$) 300 MHz: –72.46 (s) –140.30 (d). Mass spectrum: M+H=309.

Step 8

Preparation of 4-[6-fluoro-1,5-dihydro-7-methoxy-3-(trifluoromethyl)-[2]benzothiopyrano[4,3-c]pyrazol-1-yl]benzenesulfonamide 4-Sulfonamidophenylhydrazine hydrochloride (0.77 g, 3.4 mmol) was added to a stirred solution of the diketone from Step 7 (0.93 g, 3.0 mmol) in ethanol (10 mL). The reaction was heated to reflux and stirred for 20.4 hours. The reaction mixture was filtered while hot to give the pyrazole as gray needles (0.55 g, 40%): mp 250°–252° C.; $^1$H NMR (acetone-$d_6$) 300 MHz 8.08 (d, J=8.9 Hz, 2H) 7.85 (d, J=8.7 Hz, 2H) 7.01 (t, J=8.7 Hz, 1H) 6.81 (br s, 2H) 6.72 (dd, J=8.6 Hz J=1.9 Hz, 1H) 4.20 (s, 2H) 3.91 (s, 3H); $^{19}$F NMR (acetone-$d_6$) 300 MHz –63.32 (s) –140.16 (d).

EXAMPLE 2

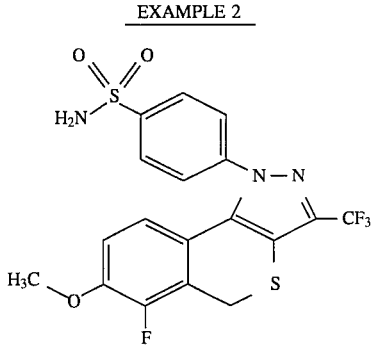

1,5-Dihydro-6-fluoro-7-methoxy-1-[(4-methylsulfonyl)phenyl]- 3-(trifluoromethyl)-[2]benzothiopyrano[4,3-c]pyrazole 4-(Methylsulfonyl)phenylhydrazine (0.75 g, 4.0 mmol) was converted to the hydrochloride salt by stirring with a 4N solution of hydrochloric acid in dioxane (10 mL) for 30 minutes. The dioxane was removed in vacuo and the 4-(methylsulfonyl)phenyl hydrazine hydrochloride was combined with the diketone from Example 1, Step 7 (0.89 g, 2.9 mmol) and ethanol (15 mL), heated to reflux and stirred for 14.5 hours. The reaction mixture was filtered while hot and the filtrate was concentrated in vacuo. The residue was dissolved in ethyl acetate, washed with water and with brine, dried over MgSO$_4$, reconcentrated in vacuo and passed through a column of silica gel, eluting with 20% ethyl acetate/hexane to give the pyrazole (0.46 g, 35%) as a yellow solid: mp 213°–215° C.; $^1$H NMR (acetone-d$_6$) 300 MHz 8.15 (d, J=8.7 Hz, 2H) 7.94 (d, J=8.7 Hz, 2H) 7.01 (t, J=8.7 Hz, 1H) 6.73 (d, J=8.7 Hz, 1H) 4.21 (s, 2H) 3.90 (s, 3H) 3.23 (s, 3H); $^{19}$F NMR (acetone-d$_6$) 300 MHz −63.41 (s) −140.17 (d). Mass spectrum: M+=458.1.

EXAMPLE 3

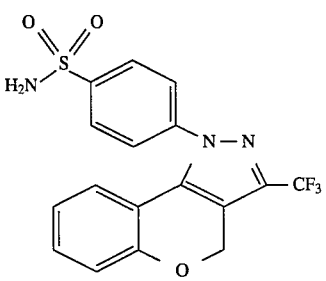

4-[1,4-Dihydro-3-(trifluoromethyl)-[1]benzopyrano[4,3-c]pyrazol-1-yl]benzenesulfonamide

Step 1

Preparation of 3-(trifluoroacetyl)-4-chromanone

Ethyl trifluoroacetate (9.78 g, 68 mmol) was placed in a 250 mL round bottom flask, and dissolved in ether (50 mL). To the stirred solution was added 25% sodium methoxide (15.11 g, 70 mmol), followed by 4-chromanone (10.07 g, 68 mmol) dissolved in ether (25 mL). The reaction was stirred at room temperature overnight (18.3 hours), poured into a separatory funnel and washed with 3N hydrochloric acid (20 mL) and with brine (20 mL), dried over MgSO$_4$, concentrated in vacuo, and recrystallized from ether/hexane to give a yellow solid (10.72 g, 65%): mp 81°–83° C.; $^1$H NMR (CDCl$_3$) 300 MHz 16.04 (br s, 1H) 7.84 (d, J=7.9 Hz, 1H) 7.51 (m, 1H) 7.09 (m, 1H) 6.98 (d, J=8.5 Hz, 1H) 5.08 (s, 2H); $^{19}$F NMR (CDCl$_3$) 300 MHz: −72.56 (s). Mass spectrum: M+=244.

Step 2

Preparation of 4-[1,4-dihydro-3-(trifluoromethyl)-[1]benzopyrano[4,3-c]pyrazol-1-yl]benzenesulfonamide 4-Sulfonamidophenylhydrazine hydrochloride (4.57 g, 20.4 mmol) was added to a stirred solution of the diketone from Step 1 (4.59 g, 18.8 mmol) in ethanol (80 mL). The reaction was heated to reflux and stirred overnight (17.3 hours). The reaction mixture was filtered while hot to give the pyrazole as a white solid (3.99 g, 54%). Upon cooling, the filtrate yielded an additional 1.97 g (26%): mp 250°–251° C.; $^1$H NMR (acetone-d$_6$) 300 MHz 8.14 (d, J=8.7 Hz, 2H), 7.87 (d, J=8.7 Hz, 2H) 7.30 (m, 1H), 7.08 (d, J=8.1Hz, 1H) 6.89 (m, 3H) 5.41 (s, 2H); $^{19}$F NMR (acetone-d$_6$) 300 MHz −62.42 (s). High resolution mass spectrum Calc'd. for C$_{17}$H$_{12}$F$_3$N$_3$O$_3$S: 395.0551. Found: 395.0551.

EXAMPLE 4

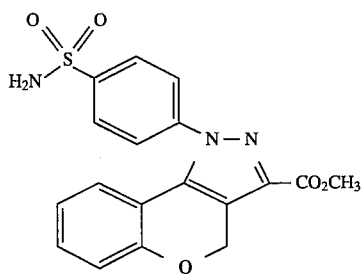

Methyl[1-[4-(aminosulfonyl)phenyl]-1,4-dihydro-[1]benzopyrano[4,3-c]pyrazol-3-yl]carboxylate

Step 1

Preparation of methyl-3-(1-oxo-2-carboxy)- 4-chromanone

A 500 mL flask was charged with 4-chromanone (9.72 g, 65.6 mmol), dimethyl oxalate (8.92 g, 75.5 mmol) and methanol (75 mL). The solution was treated with sodium methoxide (25%) in methanol (18.52 g, 85.7 mmol) and stirred at room temperature for 18.8 hours. The reaction was treated with 3N hydrochloric acid (30 mL), filtered, and recrystallized from ethyl acetate/isooctane to give the diketone (11.31 g, 74%) as a yellow solid: mp 85°–87° C.; $^1$H NMR (acetone-d$_6$) 300 MHz 7.87 (d, J=7.9 Hz, 1H) 7.61 (m, 1H) 7.14 (m, 1H) 7.02 (d, J=8.3 Hz, 1H) 5.35 (s, 2H) 3.92 (s, 3H). Mass spectrum: M+Li=234.

Step 2

Preparation of methyl [1-[4-(aminosulfonyl)phenyl]-1,4-dihydro-[1]benzopyrano[4,3-c]pyrazol-3-yl]carboxylate 4-Sulfonamidophenylhydrazine hydrochloride (6.52 g, 29.1 mmol) was added to a stirred solution of the diketone from Step 1 (6.23 g, 26.6 mmol) in methanol (MeOH) (150 mL). The reaction was heated to reflux and stirred for 15.1 hours. The reaction mixture was filtered, washed with MeOH and dried under vacuum to give the pyrazole as a pale green solid (9.81 g, 96%): mp>304° C.; $^1$H NMR (DMSO-d$_6$) 300 MHz 8.02 (d, J=8.7 Hz, 2H) 7.83 (d, J=8.5 Hz, 2H) 7.60 (br s, 2H) 7.25 (2d, 1H) 7.06 (d, J=7.5 Hz,1H) 6.84 (2d, 1H) 6.71 (d, J=7.9 Hz, 1H) 5.46 (s, 2H) 3.85 (s, 3H). Mass spectrum: M+H=386.

EXAMPLE 5

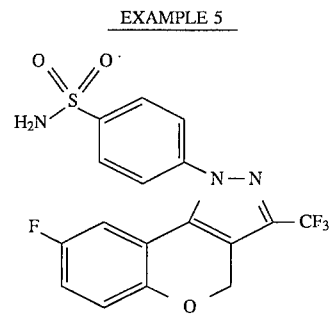

4-[1,4-Dihydro-8-fluoro-3-(trifluoromethyl)-[1]benzopyrano[4,3-c]pyrazol-1-yl]benzenesulfonamide

Step 1

Preparation of 6-fluoro-3-(trifluoroacetyl)- 4-chromanone

Ethyl trifluoroacetate (4.33 g, 30 mmol) was dissolved in ether (25 mL) and treated with sodium methoxide (25%, 7.08 g, 33 mmol). To the stirred solution was added 6-fluoro-4-chromanone (4.92 g, 30 mmol) and additional ether (10 mL). The reaction was stirred at room temperature overnight (19.0 hours) and treated with 3N hydrochloric acid (15 mL). The organic layer was collected, washed with brine, dried over MgSO$_4$, concentrated in vacuo and recrystallized from ether/hexane to give a yellow solid (3.98 g, 51%): mp 107°–112° C.; $^1$H NMR (CDCl$_3$) 300 MHz 14.95 (s, 1H) 7.52 (dd, 1H) 7.23 (m, 1H) 6.97 (m, 1H) 5.07 (s, 2H); $^{19}$F NMR (CDCl$_3$) 300 MHz –72.60 (s), –119.93 (m). Mass spectrum: M+=262.

Step 2

Preparation of 4-[1,4-dihydro-8-fluoro- 3-(trifluoromethyl)-[1]benzopyrano[4,3-c]pyrazol-1-yl]benzenesulfonamide 4-Sulfonamidophenylhydrazine hydrochloride (1.54 g, 6.9 mmol) was added to a stirred solution of the diketone from Step 1 (1.62 g, 6.2 mmol) in ethanol (35 mL). The reaction was heated to reflux and stirred overnight (17.3 hours). The reaction mixture was filtered while hot to give the pyrazole as a white solid (1.09 g, 43%). Upon cooling, the filtrate yielded an additional 0.70 g (27%): mp 251°–251.5° C.; $^1$H NMR (acetone-d$_6$) 300 MHz 8.17 (d, J=8.5 Hz, 2H) 7.91 (d, J=8.7 Hz, 2H) 7.11 (m, 2H) 6.87 (br s, 1H) 6.58 (dd, J=2.4Hz, 9.5Hz, 3H) 5.41 (s, 2H); $^{19}$F NMR (acetone-d$_6$) 300 MHz –62.46 (s). High resolution mass spectrum Calc'd. for C$_{17}$H$_{11}$F$_4$N$_3$O$_3$S: 413.0457. Found: 413.0462.

EXAMPLE 6

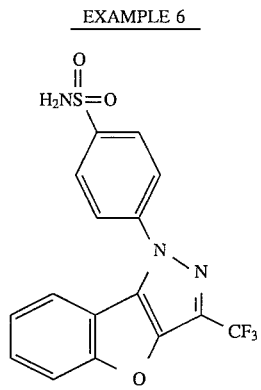

4-[3-(Trifluoromethyl)-1H-benzofuro[3,2-c]pyrazol-1-yl]benzenesulfonamide

Step 1

Preparation of 2-(trifluoroacetyl)-3-coumaranone

Ethyl trifluoroacetate (1.90 g, 14 mmol) was dissolved in ether (15 mL) and treated with sodium methoxide (25%) (3.67 g, 17 mmol). To the stirred solution was added 3-coumaranone (1.50 g, 11 mmol). The reaction was stirred at room temperature overnight (19 hours) and treated with 3N HCl (8 mL). The organic layer was collected, washed with brine, dried over MgSO$_4$, and concentrated in vacuo to give a reddish brown solid (2.19 g, 85%): mp 108°–111° C.; $^1$H NMR (CDCl$_3$) 300 MHz 7.84 (d, J=8.1 Hz, 1H) 7.66 (m, 1H) 7.52 (d, J=8.7 Hz, 1H) 7.37 (m, 1H). Mass spectrum: M+H=231.

Step 2

Preparation of 4-[3-(trifluoromethyl)- 1H-benzofuro[3,2-c]pyrazol-1-yl]benzenesulfonamide 4-Sulfonamidophenylhydrazine hydrochloride (1.15 g, 5.0 mmol) was added to a stirred solution of the diketone from Step 1 (1.13 g, 4.9 mmol) in ethanol (10 mL). The reaction was heated to reflux and stirred for 2.5 hours. The reaction mixture was filtered to give the pyrazole as a brown solid (1.07 g, 57%): mp 190°–195° C.; $^1$H NMR (acetone-d$_6$) 300 MHz 7.82–7.90 (m, 3H) 7.34–7.53 (m, 5H); $^{19}$F NMR (acetone-d$_6$) 300 MHz –65.47 (s).

EXAMPLE 7

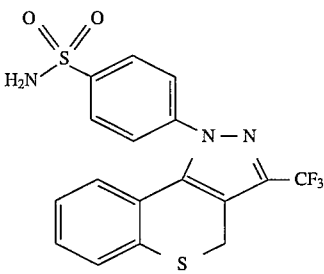

4-[1,4-Dihydro-3-(trifluoromethyl)-[1]benzothiopyrano[4,3-c]pyrazol-1-yl]benzenesulfonamide

Step 1

Preparation of 3-(trifluoroacetyl)thio- 4-chromanone

Ethyl trifluoroacetate (8.78 g, 62 mmol) was placed in a 250 mL round bottom flask, and dissolved in ether (50 mL). To the stirred solution was added sodium methoxide (14.35 g, 66 mmol) followed by thio-4-chromanone (9.43 g, 57 mmol) dissolved in ether (10 mL). The reaction was stirred at room temperature overnight (17.8 hrs) and treated with 3N HCl (25 mL). The organic layer was collected, washed with brine, dried over $MgSO_4$, concentrated in vacuo and recrystallized from ether/hexane to give a yellow solid (10.20 g, 68%): mp 75°–79° C.; $^1$H NMR ($CDCl_3$) 300 MHz 15.62 (s, 1H) 7.99 (d, J=7.9Hz, 1H) 7.24–7.42 (m, 3H) 3.81 (s,2H); $^{19}$F NMR ($CDCl_3$) 300 MHz −71.92 (s). Mass spectrum: M+=260.

Step 2

Preparation of 4-[1,4-dihydro-3-(trifluoromethyl)-[1]benzothiopyrano[4,3-c]pyrazol-1-yl]benzenesulfonamide 4-Sulfonamidophenylhydrazine hydrochloride (5.74 g, 25.6 mmol) was added-to a stirred solution of the diketone from Step 1 (6.04 g, 23.2 mmol) in ethanol (95 mL). The reaction was heated to reflux and stirred overnight (17.0 hours). The reaction mixture was filtered, and the filtrate cooled to 0° C. and filtered to give the pyrazole as a yellow solid (4.42 g, 46%): mp 213°–215° C.; $^1$H NMR (acetone-$d_6$) 300 MHz 8.09 (d, J=8.9 Hz, 2H) 7.75 (d, J=8.7 Hz, 2H) 7.53 (d, J=7.8Hz,1H) 7.29 (2d, 1H) 7.07 (2d, 1H) 6.94 (d, J=8.1Hz, 2H) 6.92 (br s, 1H) 4.09 (s, 2H); $^{19}$F NMR (acetone-$d_6$) 300 MHz −62.22 (s). High resolution mass spectrum Calc'd. for $C_{17}H_{12}F_3N_3O_2S_2$: 411.0323. Found: 411.0330.

EXAMPLE 8

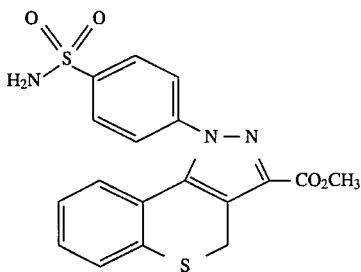

Methyl[1-[(4-aminosulfonyl)phenyl]-1,4-dihydro-[1]benzothiopyrano[4,3-c]pyrazol-3-yl]carboxylate

Step 1

Preparation of methyl-3-(1-oxo-2-carboxy)thiochroman-4-one

A 500 mL flask was charged with thiochroman-4-one (9.84 g, 59.9 mmol), dimethyl oxalate (8.54 g, 72.3 mmol) and methanol (75 mL). The reaction was treated with sodium methoxide (25% in methanol, 15.61 g, 72.2 mmol) and stirred at room temperature for 17.8 hours. The reaction was treated with 3N hydrochloric acid (30 mL) and filtered to give the diketone (13.58 g, 90%) as an orange solid: mp 94°–97° C.; $^1$H NMR ($CDCl_3$) 300 MHz 15.94 (s, 1H) 8.01 (d, J=7.9 Hz, 1H) 7.24–7.39 (m, 3H) 4.11 (s, 2H) 3.94 (s, 3H). Mass spectrum: M+=250.

Step 2

Preparation of methyl 1-[4-(aminosulfonyl)phenyl]- 1,4-dihydro-[1]benzothiopyrano[4,3-c]pyrazol-3-yl]carboxylate 4-Sulfonamidophenylhydrazine hydrochloride (12.06 g, 53.9 mmol) was added to a stirred solution of the diketone from Step 1 (12.23 g, 48.9 mmol) in MeOH (250 mL). The reaction was heated to reflux and stirred for 6.5 hours. The reaction mixture was filtered, washed with MeOH and dried under vacuum to give the pyrazole as an orange solid (17.88 g, 91%): mp 265°–269° C.; $^1$H NMR (DMSO-$d_6$) 300 MHz 7.97 (d, J=8.5 Hz, 2H) 7.69 (d, J=8.5 Hz, 2H) 7.58 (br s, 2H) 7.50 (d, J=7.9 Hz, 1H) 7.24 (t, J=7.7 Hz,1H) 7.04 (d, J=7.7 Hz, 1H) 6.76 (d, J=7.9 Hz, 1H) 4.21 (s, 2H) 3.86 (s, 3H). Mass spectrum: M+H=402.

EXAMPLE 9

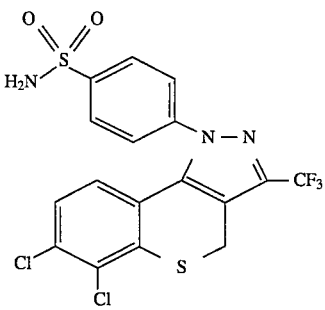

4-[6,7-Dichloro-1,4-dihydro-3-(trifluoromethyl)-[1]benzothiopyrano[4,3-c]pyrazol-1-yl]benzenesulfonamide

Step 1

Preparation of 3-(2,3-dichlorophenylthio)propanoic acid 2,3-Dichlorothiophenol (4.94 g, 28 mmol) was placed in a flask with acrylic acid (2.11 g, 29 mmol) and stirred at 50° C. for 3 hours. The reaction mixture was poured into 10% $Na_2CO_3$ and extracted with ether. The aqueous layer was acidified with concentrated hydrochloric acid, extracted with ether, washed with brine, dried over $MgSO_4$, and concentrated in vacuo to give the 3-(2,3-dichlorophenylthio)propanoic acid (3.88 g), contaminated with some acrylic acid, as a clear oil which was used without further purification in the next step.

Step 2

Preparation of 7,8-dichlorothiochroman- 4-one

The 3-(2,3-dichlorophenylthio)propanoic acid from Step 1 (3.88 g, 15 mmol) was dissolved in trifluoroacetic acid (10 mL), treated with trifluoroacetic anhydride (5 mL) and stirred at room temperature for 68.2 hours. The reaction mixture was poured into 10% $Na_2CO_3$ (100 mL), extracted with ethyl acetate, washed with brine, dried over $MgSO_4$, and concentrated in vacuo to give a yellow oil. The crude material was passed through a column of silica gel eluting with 40% ethyl acetate/hexane to give 7,8-dichlorothiochroman- 4-one as a white solid (0.46 g, 13%): mp 93°–102° C.; $^1$H NMR ($CDCl_3$) 300 MHz 7.99 (d, J=8.7 Hz, 1H) 7.27 (d, J=8.7 Hz, 1H) 3.25 (m, 2H) 2.97 (m, 2H). Mass spectrum: M+=233.

Step 3

Preparation of 7,8-dichloro-3-(trifluoroacetyl)thiochroman-4-one

Ethyl trifluoroacetate (0.29 g, 2.0 mmol) was placed in a round bottom flask, and dissolved in ether (12 mL). To the stirred solution was added sodium methoxide (25%) (0.84 g, 3.9 mmol), followed by 7,8-dichlorothiochroman-4-one from Step 2 (0.42 g, 1.8 mmol). The reaction was stirred at room temperature overnight (19.4 hours) and treated with 3N hydrochloric acid. The organic layer was collected, washed with brine, dried over $MgSO_4$, and concentrated in vacuo to give a brown oily solid which was used without purification in the next step.

Step 4

Preparation of 4-[6,7-dichloro-1,4-dihydro-3-(trifluoromethyl)-[1]benzothiopyrano[4,3-c]pyrazol-1-yl]benzenesulfonamide 4-Sulfonamidophenylhydrazine hydrochloride (0.32 g, 1.4 mmol) was added to a stirred solution of the diketone from Step 3 (0.44 g, 1.3 mmol) in ethanol (10 mL). The reaction was heated to reflux and stirred overnight (19.4 hours). The reaction mixture was filtered and the filtrate concentrated in vacuo, dissolved in ethyl acetate, washed with water and brine, dried over $MgSO_4$, reconcentrated in vacuo, and passed through a column of silica gel (hexane/ethyl acetate) to give the pyrazole as a white solid (0.24 g, 38%): $^1$H NMR (acetone-$d_6$) 300 MHz 8.08 (d, J=8.7 Hz, 2H) 7.77 (d, J=8.7 Hz, 2H) 7.27 (d, J=8.5Hz, 1H) 6.95 (d, J=8.5Hz,1H) 6.79 (br s, 2H) 4.23 (s, 2H); $^{19}$F NMR (acetone-$d_6$) 300 MHz −62.25 (s). High resolution mass spectrum Calc'd. for $C_{17}H_{10}Cl_2F_3N_3O_2S_2$: 479.9622. Found: 479.9565.

EXAMPLE 10

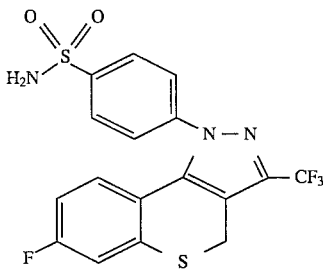

4-[1,4-Dihydro-7-fluoro-3-(trifluoromethyl)-[1]benzothiopyrano[4,3-c]pyrazol-1-yl]benzenesulfonamide

Step 1

Preparation of 3-(3-fluorophenylthio)propanoic acid

3-Fluorothiophenol (5.39 g, 42 mmol) was placed in a flask with acrylic acid (3.73 g, 52 mmol) and stirred at room temperature for 20.2 hours. The reaction mixture solidified, was dissolved in ether and extracted with 10% $Na_2CO_3$. The aqueous layer was acidified with concentrated hydrochloric acid, extracted with ether, washed with brine, dried over $MgSO_4$, and concentrated in vacuo to give the 3-(3-fluorophenylthio)propanoic acid (6.75 g), contaminated with some acrylic acid, as a white solid which was used without further purification in the next step.

Step 2

Preparation of 7-fluorothiochroman-4-one

The acid from Step 1 (6.75 g, 34 mmol) was dissolved in trifluoroacetic acid (20 mL), treated with trifluoroacetic anhydride (10 mL) and stirred at room temperature for 2.2 hours. The reaction mixture was poured into 10% $Na_2CO_3$ (100 mL), extracted with ether, washed with brine, dried over $MgSO_4$, and concentrated in vacuo to give a yellow oil which was passed through a column of silica gel with 20% ethyl acetate/hexane to give 7-fluorothiochroman-4-one as a white solid (2.09 g, 34%): mp 61°–66° C.; $^1$H NMR (CDCl$_3$) 300 MHz 8.13 (m, 1H) 6.98 (m, 1H) 6.86 (m, 1H) 3.23 (m, 2H) 2.99 (m, 2H); $^{19}$F NMR (CDCl$_3$) 300 MHz −104.70 (m). Mass spectrum: M+H=183.

Step 3

Preparation of 7-fluoro-3-(trifluoroacetyl)thiochroman-4-one

Ethyl trifluoroacetate (1.04 g, 7.3 mmol) was added to solution of 7-fluorothiochroman-4-one from Step 2 (1.24 g, 6.8 mmol) in ether (15 mL). The reaction was treated with 25% sodium methoxide (1.86 g, 8.6 mmol) and stirred at room temperature for 20.9 hours, then treated with 3N hydrochloric acid (10 mL). The organic layer was collected, washed with brine, dried over $MgSO_4$, concentrated in vacuo, and recrystallized from dichloromethane/isooctane to give the diketone as a yellow solid (0.58 g, 31%): mp 84°–89° C.; $^1$H NMR (CDCl$_3$) 300 MHz 15.65 (s, 1H) 8.03 (m, 1H) 7.08 (m, 1H) 6.97 (m, 1H) 3.83 (s, 2H); $^{19}$F NMR (CDCl$_3$) 300 MHz −71.81 (s) −103.04 (m).

Step 4

Preparation of 4-[1,4-dihydro-7-fluoro-3-(trifluoromethyl)-[1]benzothiopyrano[4,3-c]pyrazol-1-yl]benzenesulfonamide 4-Sulfonamidophenylhydrazine hydrochloride (1.36 g, 6.1 mmol) was added to a stirred solution of the diketone from Step 3 (1.65 g, 5.9 mmol) in ethanol (10 mL). The reaction was heated to reflux and stirred overnight (15.2 hours). The reaction mixture was filtered and the filtrate cooled in ice to give the pyrazole as a white solid (0.24 g, 38%): $^1$H NMR (acetone-$d_6$) 300 MHz 8.09 (d, J=8.7 Hz, 2H) 7.76 (d, J=8.7 Hz, 2H) 7.38 (d, J=9.1Hz, 1H) 6.99 (m, 1H) 6.88 (m, 1H) 6.80 (br s, 2H) 4.14 (s, 2H); $^{19}$F NMR (acetone-$d_6$) 300 MHz: −62.25 (s) −112.68 (m). High resolution mass spectrum Calc'd. for $C_{17}H_{11}F_4N_3O_2S_2$: 429.0229. Found: 429.0205.

EXAMPLE 11

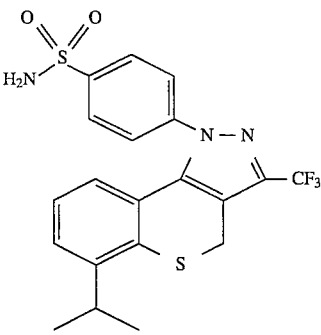

4-[1,4-Dihydro-6-isopropyl-3-(trifluoromethyl)-[1]benzothiopyrano[4,3-c]pyrazol-1-yl]benzenesulfonamide

Step 1

Preparation of 3-(2-isopropylphenylthio)propanoic acid

2-Isopropylthiophenol (4.77 g, 31 mmol) was placed in a flask with acrylic acid (2.37 g, 33 mmol) and stirred at room temperature for 71.8 hours. The reaction mixture solidified, was dissolved in ethyl acetate and extracted with 5% NaOH. The aqueous layer was acidified with concentrated hydrochloric acid, extracted with ethyl acetate, dried over $MgSO_4$, and concentrated in vacuo to give 3-(2-isopropylphenylthio)propanoic acid (6.85 g), contaminated with some acrylic acid, as a yellow solid which was used without further purification in the next step.

Step 2

Preparation of 8-isopropylthiochroman-4-one 3-(2-Isopropylphenylthio)propanoic acid from Step 1 (6.85 g, 30 mmol) was dissolved in trifluoroacetic acid (20 mL), treated with trifluoroacetic anhydride (12 mL) and stirred at room temperature (64.2 hours). The reaction was concentrated in vacuo, and the residue dissolved in ethyl acetate, extracted with 5% NaOH, washed with brine, dried over $MgSO_4$, and concentrated in vacuo to give a brown oil which was passed through a column of silica gel eluted with 12% ether/hexane to give 8-isopropylthiochroman-4-one as a brown oil (1.05 g, 17%): $^1$H NMR ($CDCl_3$) 300 MHz 8.01 (d, J=7.0 Hz, 1H) 7.38 (d, J=7.5 Hz, 1H) 7.17 (t, J=7.8 Hz, 1H) 3.19 (m, 3H) 2.96 (m, 2H) 1.25 (d, J=7.0 Hz 6H).

Step 3

Preparation of 8-isopropyl-3-(trifluoroacetyl)thiochroman-4-one

Ethyl trifluoroacetate (0.69 g, 4.9 mmol) was added to a solution of 2-isopropylthiochroman-4-one from Step 2 (0.97 g, 4.7 mmol) in ether (10 mL). The reaction was treated with 25% sodium methoxide (1.08 g, 5.0 mmol), stirred at room temperature for 18.2 hours and treated with 3N hydrochloric acid (5 mL). The organic layer was collected, washed with brine, dried over $MgSO_4$ and concentrated in vacuo to give the diketone as a brown oil (0.80 g) which was used without further purification in the next step.

Step 4

Preparation of 4-[1,4-dihydro-6-isopropyl-3-(trifluoromethyl)-[1]benzothiopyrano[4,3-c]pyrazol-1-yl]benzenesulfonamide 4-Sulfonamidophenylhydrazine hydrochloride (0.69 g, 3.1 mmol) was added to a stirred solution of the diketone from Step 3 (0.83 g, 2.7 mmol) in ethanol (10 mL). The reaction was heated to reflux, stirred overnight (16.1 hours) and concentrated in vacuo. The residue was dissolved in ethyl acetate washed with water, washed with brine, dried over $MgSO_4$, reconcentrated in vacuo and passed through a column of silica gel with 20% ethyl acetate/hexane to give the pyrazole as a brown solid (0.43 g, 35%): mp 183°–186° C. $^1$H NMR (acetone-$d_6$) 300 MHz 8.10 (d, J=8.7 Hz, 2H) 7.71 (d, J=8.5 Hz, 2H) 7.35 (d, J=7.9 Hz, 1H) 7.04 (t, J=7.9 Hz, 1H) 6.79 (m, 3H) 4.04 (s, 2H) 3.46 (m, 1H) 1.28 (d, J=6.8 Hz, 6H); $^{19}$F NMR (acetone-$d_6$) 300 MHz −62.19 (s) −112.68 (m). High resolution mass spectrum Calc'd. for $C_{20}H_{18}F_3N_3O_2S_2$: 453.0793. Found: 453.0848.

EXAMPLE 12

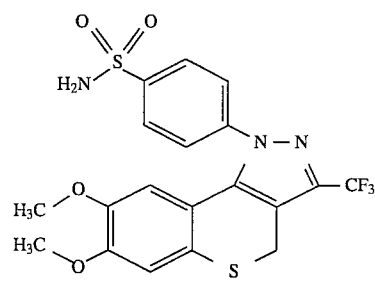

4-[1,4-Dihydro-7,8-dimethoxy-3-(trifluoromethyl)-[1]benzothiopyrano[4,3-c]pyrazol-1-yl]benzenesulfonamide

Step 1

Preparation of 3-(3,4-dimethoxyphenylthio)propanoic acid 3,4-Dimethoxythiophenol (5.00 g, 29 mmol) was placed in a flask with acrylic acid (2.27 g, 32 mmol) and stirred at room temperature for 22.4 hours. The reaction mixture solidified, was dissolved in ethyl acetate and extracted with 10% $Na_2CO_3$. The aqueous layer was acidified with concentrated hydrochloric acid, extracted with ether, dried over $MgSO_4$, and concentrated in vacuo to give 3-(3,4-dimethoxyphenylthio)propanoic acid (5.39 g, 76%), contaminated with some acrylic acid, as a white solid which was used without further purification in the next step: mp 62°–64° C.; $^1$H NMR ($CDCl_3$) 300 MHz 9.80 (br s, 1H) 7.01 (d, J=8.3 Hz, 1H) 6.98 (s, 1H) 6.82 (d, J=8.3 Hz, 1H) 3.87 (s, 3H) 3.86 (s, 3H) 3.06 (t, J=7.3 Hz, 2H) 2.63 (t, J=7.3 Hz, 2H). Mass spectrum: M+=242.

Step 2

Preparation of 6,7-dimethoxythiochroman-4-one

The acid from Step 1 (5.23 g, 22 mmol) was dissolved in trifluoroacetic acid (20 mL), treated with trifluoroacetic anhydride (12 mL) and stirred at room temperature (10 minutes). The reaction was poured into 10% $Na_2CO_3$ (100 mL) and filtered to collect 6,7-dimethoxythiochromanone as a yellow solid (1.12 g, 23%). The filtrate was washed with brine, dried over $MgSO_4$, concentrated in vacuo and recrystallized from ethyl acetate/hexane to give more 6,7-dimethoxythiochromanone (1.77 g, 37%) as an orange solid: mp 138°–143° C.; $^1$H NMR ($CDCl_3$) 300 MHz 7.60 (s, 1H) 6.68 (s, 1H) 3.91 (s, 3H) 3.89 (s, 3H) 3.19 (m, 2H) 2.93 (m, 3H). Mass spectrum: M+=224.

Step 3

Preparation of 6,7-dimethoxy-3-trifluoroacetylthiochroman-4-one

Ethyl trifluoroacetate (0.84 g, 5.9 mmol) was dissolved in tetrahydrofuran (20 mL), and treated with 25% sodium methoxide (1.68 g, 7.8 mmol). To the stirred solution was added 6,7-dimethoxythiochroman-4-one from Step 2 (1.12 g, 5.0 mmol). The reaction was stirred at room temperature for 87.5 hours, treated with 3N HCl (25 mL) and filtered to give an orange solid (1.04 g, 65%): mp 148°–151° C.; $^1$H NMR ($CDCl_3$) 300 MHz 16.05 (s, 1H), 7.48 (s, 1H) 6.78 (s, 1H) 3.94 (s, 3H) 3.92 (s, 3H) 3.83 (s, 2H); $^{19}$F NMR ($CDCl_3$) 300 MHz −71.06 (s). Mass spectrum: M+H=321.

Step 4

Preparation of 4-[1,4-dihydro-7,8-dimethoxy- 3-(trifluoromethyl)-[1]benzothiopyrano[4,3-c]pyrazol-1-yl]benzenesulfonamide 4-Sulfonamidophenylhydrazine hydrochloride (0.76 g, 3.4 mmol) was added to a stirred solution of the diketone from Step 3 (1.00 g, 3.1 mmol) in ethanol (20 mL). The reaction was heated to reflux and stirred overnight (15.5 hours). The reaction mixture was filtered and the filtrate concentrated in vacuo, dissolved in ethyl acetate, washed with water and brine, dried over MgSO$_4$, reconcentrated in vacuo, and recrystallized from ethyl acetate/isooctane to give the pyrazole as a yellow solid (0.72 g, 49%): mp 164°–168° C.; $^1$H NMR (acetone-d$_6$) 300 MHz 8.13 (d, J=8.7 Hz, 2H) 7.77 (d, J=8.5 Hz, 2H) 7.06 (s, 1H) 6.82 (br s, 2H) 6.36 (s, 1H) 4.04 (s, 2H) 3.85 (s, 3H) 3.85 (s, 3H); $^{19}$F NMR (acetone-d$_6$) 300 MHz −62.20 (s). High resolution mass spectrum Calc'd. for C$_{19}$H$_{16}$F$_3$N$_3$O$_4$S$_2$: 471.0534. Found: 471.0534.

EXAMPLE 13

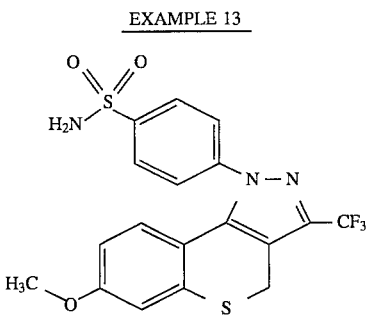

4-[1,4-Dihydro-7-methoxy-3-(trifluoromethyl)-[1]benzothiopyrano[4,3-c]pyrazol-1-yl]benzenesulfonamide

Step 1

Preparation of 3-(3-methoxyphenylthio)propanoic acid

3-Methoxythiophenol (5.70 g, 41 mmol) was placed in a flask with acrylic acid (2.36 g, 33 mmol) and stirred at room temperature for 113.8 hours. The reaction mixture was dissolved in ether and extracted with 10% Na$_2$CO$_3$. The aqueous layer was acidified with concentrated HCl, extracted with ether, dried over MgSO$_4$, and concentrated in vacuo to give the 3-( 3-methoxyphenylthio)propanoic acid (2.55 g , 37%) as a white solid: mp 39°–42° C.; $^1$H NMR (CDCl$_3$) 300 MHz 7.21 (m, 1H) 6.91 (m, 2H) 6.77 (d, J=8.3 Hz, 1H) 3.79 (s, 3H) 3.16 (t, J=7.5 Hz, 2H) 2.68 (t, J=7.3 Hz, 2H).

Step 2

Preparation of 7-methoxythiochroman-4-one

The acid from Step 1 (2.55 g, 12 mmol) was dissolved in trifluoroacetic acid (10 mL), treated with trifluoroacetic anhydride (5 mL) and stirred at room temperature (10 minutes). The reaction was poured into 10% Na$_2$CO$_3$ (60 mL), extracted with ether, washed with brine, dried over MgSO$_4$, and concentrated in vacuo to give a red oil which was passed through a column of silica gel with 50% ether/hexane to give 7-methoxythiochroman- 4-one as an orange solid (1.18 g, 51%): mp 49°–51° C.; $^1$H NMR (CDCl$_3$) 300 MHz 8.06 (d, J=8.9 Hz, 1H) 6.72 (m, 2H) 3.83 (s, 3H) 3.20 (m, 2H) 2.95 (m, 2H). Mass spectrum: M+H=195.

Step 3

Preparation of 7-methoxy-3-(trifluoroacetyl)thiochroman- 4-one

7-Methoxythiochroman-4-one from Step 2 (1.13 g, 5.8 mmol) and ethyl trifluoroacetate (0.87 g, 6.1 mmol) were dissolved in ether (15 mL), treated with 25% sodium methoxide (2.13 g, 9.9 mmol), stirred at room temperature for 23.0 hours, and treated with 3N HCl. The organic layer was collected, washed with brine, dried over MgSO$_4$, concentrated in vacuo and recrystallized from dichloromethane/ isooctane to give the diketone as a yellow solid (0.60 g, 35%): mp 93°–98° C.; $^1$H NMR (CDCl$_3$) 300 MHz 15.92 (s, 1H) 7.96 (d, J=8.9 Hz, 1H) 6.82 (m, 2H) 3.87 (s, 3H) 3.82 (s, 2H); $^{19}$F NMR (CDCl$_3$) 300 MHz −71.43 (s). Mass spectrum: M+H=291.

Step 4

Preparation of 4-[1,4-dihydro-7-methoxy-3-(trifluoromethyl)-[1]benzothiopyrano[4,3-c]pyrazol-1-yl]benzenesulfonamide 4-Sulfonamidophenylhydrazine hydrochloride (0.46 g, 2.1 mmol) was added to a stirred solution of the diketone from Step 3 (0.57 g, 2.0 mmol) in ethanol (5 mL). The reaction was heated to reflux and stirred overnight (21.5 hrs). The reaction mixture was filtered while hot to give the pyrazole as a yellow solid (0.63 g, 72%): mp 201°–206° C.; $^1$H NMR (acetone-d$_6$) 300 MHz 8.08 (d, J=8.7 Hz, 2H) 7.73 (d, J=8.7 Hz, 2H) 7.09 (d, J=2.6 Hz, 1H) 6.84 (d, J=8.7 Hz, 1H) 6.80 (br s,1H) 6.66 (dd, J=2.6 Hz J=8.9 Hz, 1H) 4.07 (s, 2H) 3.83 (s, 3H); $^{19}$F NMR (acetone-d$_6$) 300 MHz −62.24 (s). High resolution mass spectrum Calc'd. for C$_{18}$H$_{14}$F$_3$N$_3$O$_3$S$_2$: 441.0429. Found: 441.0457.

EXAMPLE 14

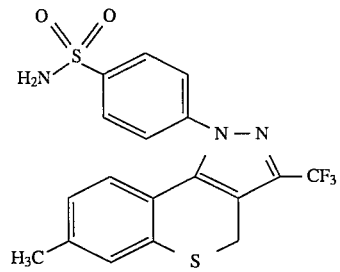

4-[1,4-Dihydro-7-methyl-3-(trifluoromethyl)-[1]benzothiopyrano[4,3-c]pyrazol-1-yl]benzenesulfonamide

Step 1

Preparation of 3-(3-methoxyphenylthio)propanoic acid

3-Thiocresol (9.71 g, 78 mmol) was placed in a flask with acrylic acid (5.65 g, 78 mmol) and stirred at room temperature for 62.9 hours. The reaction mixture solidified and was dissolved in ether and extracted with 10% Na$_2$CO$_3$. The aqueous layer was acidified with concentrated hydrochloric acid, extracted with ether, washed with brine, dried over MgSO$_4$ and concentrated in vacuo to give the 3-( 3-dimethylphenylthio)propanoic acid (10.13 g , 66%) contaminated with some acrylic acid as a white solid, which was used without further purification in the next step.

Step 2

Preparation of 7-methylthiochroman-4-one 3-(3-Methylphenylthio)propanoic acid from Step 1 (10.12 g, 52 mmol) was dissolved in trifluoroacetic acid (20 mL), treated with trifluoroacetic anhydride (10 mL) and stirred at room temperature for 1.9 hours. The reaction was poured into 10% $Na_2CO_3$ (100 mL), extracted with ether, washed with brine, dried over $MgSO_4$, and concentrated in vacuo to give an orange oil which was passed through a column of silica gel eluting with 8% ether/hexane to give 7-methylthiochroman-4-one (2.97 g, 32%) as a yellow oil: $^1$H NMR ($CDCl_3$) 300 MHz 7.97 (d, J=8.1 Hz, 1H) 7.06 (s, 1H) 6.97 (d, J=7.7 Hz, 1H) 3.17 (m, 2H) 2.95 (m, 2H) 2.31 (s, 3H). Mass spectrum: M+H=179.

Step 3

Preparation of 7-methyl-3-(trifluoroacetyl)thiochroman-4-one

7-Methylthiochroman-4-one from Step 2 (2.92 g, 16 mmol) and ethyl trifluoroacetate (2.45 g, 17 mmol) were dissolved in ether (20 mL), treated with 25% sodium methoxide (4.60 g, 21 mmol), stirred at room temperature for 15.0 hours and treated with 3N hydrochloric acid (15 mL). The organic layer was collected, washed with brine, dried over $MgSO_4$, concentrated in vacuo, and recrystallized from dichloromethane/isooctane to give the diketone as a yellow solid (3.05 g, 68%): mp 68°–72° C.; $^1$H NMR ($CDCl_3$) 300 MHz 15.73 (s, 1H) 7.89 (d, J=8.1 Hz, 1H) 7.17 (s, 1H) 7.09 (d, J=8.1 Hz, 1H) 3.80 (s, 2H) 2.37 (s, 3H); $^{19}$F NMR ($CDCl_3$) 300 MHz −71.75 (s). Mass spectrum: M+H=275.

Step 4

Preparation of 4-[1,4-dihydro-7-methyl-3-(trifluoromethyl)-[1]benzothiopyrano[4,3-c]pyrazol-1-yl]benzenesulfonamide 4-Sulfonamidophenylhydrazine hydrochloride (1.21 g, 5.4 mmol) was added to a stirred solution of the diketone from Step 3 (1.41 g, 5.1 mmol) in ethanol (20 mL). The reaction was heated to reflux and stirred overnight (15.8 hours). The reaction mixture was filtered and the filtrate concentrated in vacuo, dissolved in ethyl acetate, washed with water and brine, dried over $MgSO_4$, reconcentrated in vacuo, and recrystallized from ethyl acetate/isooctane to give the pyrazole as a yellow solid (1.14 g, 52%): mp 251°–252° C.; $^1$H NMR (acetone-$d_6$) 300 MHz 8.08 (d, J=8.7 Hz, 2H) 7.73 (d, J=8.7 Hz, 2H) 7.36 (s, 1H) 6.79 (m, 4H) 4.06 (s, 2H) 2.29 (s, 3H); $^{19}$F NMR (acetone-$d_6$) 300 MHz −62.22(s). High resolution mass spectrum Calc'd. for $C_{18}H_{14}F_3N_3O_2S_2$: 425.0480. Found: 425.0470.

EXAMPLE 15

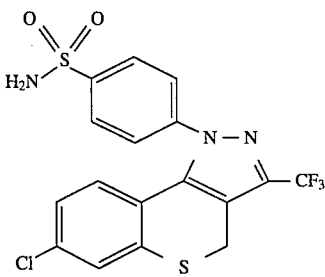

4-[7-Chloro-1,4-dihydro-3-(trifluoromethyl)-[1]benzothiopyrano[4,3-c]pyrazol-1-yl]benzenesulfonamide

Step 1

Preparation of 3-(3-chlorophenylthio)propanoic acid

Acrylic acid (2.66 g, 37 mmol) and 3-chlorothiophenol (4.85 g, 34 mmol) were dissolved in ether (15 mL) and stirred at room temperature for 88.0 hours. The reaction mixture solidified, was dissolved in ether and extracted with 5% NaOH. The aqueous layer was acidified with concentrated hydrochloric acid, extracted with ether, washed with brine, dried over $MgSO_4$, and concentrated in vacuo to give the 3-(3-chlorophenylthio)propanoic acid (2.20 g, 34%): $^1$H NMR (acetone-$d_6$) 300 MHz 7.33–7.40 (m, 3H) 7.24 (m, 1H) 3.25 (t, J=7.1 Hz, 2H) 2.67 (t, J=7.1 Hz, 2H). Mass spectrum: M+H=217.

Step 2

Preparation of 7-chlorothiochroman-4-one 3-(3-Chlorophenylthio)propanoic acid from Step 1 (2.18 g, 10 mmol) was dissolved in trifluoroacetic acid (10 mL), treated with trifluoroacetic anhydride (6 mL) and stirred at room temperature for 67.8 hours. The reaction was concentrated in vacuo and the residue dissolved in dichloromethane, extracted with 5% NaOH, dried over $MgSO_4$, and reconcentrated in vacuo to give a brown oil. The crude oil was passed through a column of silica gel with 10% ether/hexane to give a mixture of 7-chlorothiochroman-4-one and 5-chlorothiochroman-4-one as a yellow oil (1.30 g) which was carried on to the next step without further purification.

Step 3

Preparation of 7-chloro-3-(trifluoroacetyl)thiochroman-4-one

Ethyl trifluoroacetate (1.02 g, 7.2 mmol) was placed in a round bottom flask and dissolved in ether (10 mL). To the stirred solution was added 25% sodium methoxide (1.80 g, 8.3 mmol) followed by 7-chlorothiochroman- 4-one from Step 2 (1.30 g, 6.5 mmol). The reaction was stirred at room temperature overnight (17.3 hrs) and treated with 3N hydrochloric acid (5 mL). The organic layer was collected, washed with brine, dried over $MgSO_4$, concentrated in vacuo, and recrystallized from ether/hexane to give the diketone (0.61 g, 32%) as a yellow solid: mp 64°–71° C.; $^1$H NMR ($CDCl_3$) 300 MHz 15.53 (s, 1H) 7.92 (d, J=8.5 Hz, 1H) 7.36 (s, 1H) 7.25 (d, J=8.7 Hz, 1H) 3.82 (s, 2H); $^{19}$F NMR ($CDCl_3$) 300 MHz −71.97 (s). Mass spectrum: M+=294.

Step 4

Preparation of 4-[7-chloro-1,4-dihydro-3-(trifluoromethyl)-[1]benzothiopyrano[4,3-c]pyrazol-1-yl]benzenesulfonamide 4-Sulfonamidophenylhydrazine hydrochloride (0.43 g, 1.9 mmol) was added to a stirred solution of the diketone from Step 3 (0.55 g, 1.9 mmol) in ethanol (6 mL). The reaction was heated to reflux and stirred for 18.9 hours. The reaction mixture was cooled and filtered to give the pyrazole as a yellow solid (0.15 g, 18%): mp 237°–238° C.; $^1$H NMR (acetone-d $_6$) 300 MHz 8.09 (d, J=8.7 Hz, 2H) 7.77 (d, J=8.7 Hz, 2H) 7.59 (d, J=2.0 Hz, 1H) 7.10 (dd, J=8.5 Hz J=2.0Hz, 1H) 6.96 (d, J=8.5 Hz, 1H) 6.81 (br s, 2H) 4.14 (s, 2H); $^{19}$F NMR (acetone-$d_6$) 300 MHz −62.25 (s). High resolution mass spectrum Calc'd. for $C_{17}H_{11}ClF_3N_3O_2S_2$: 444.9933. Found: 444.9874.

EXAMPLE 16

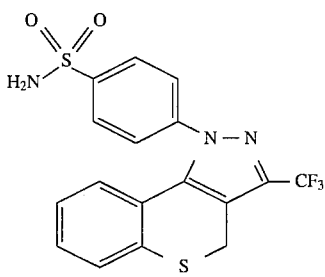

4-[1,5-Dihydro-3-(trifluoromethyl)-[2]benzothiopyrano[4,3-c]pyrazol-1-yl]benzenesulfonamide

Step 1

Preparation of 3-(trifluoroacetyl)isothiochroman-4-one

Ethyl trifluoroacetate (3.67 g, 25.8 mmol) was dissolved in tetrahydrofuran (15 mL) and treated with 25% sodium methoxide (6.46 g, 29.9 mmol) followed by a solution of isothiochroman-4-one (4.15 g, 25.3 mmol) in tetrahydrofuran (15 mL). The reaction was stirred at room temperature for 70.8 hours and treated with 3N hydrochloric acid (10 mL). The organic layer was collected, washed with brine, dried over $MgSO_4$, concentrated in vacuo, and passed through a column of silica gel eluting with 40% ethyl acetate/hexane to give a brown solid (5.40 g, 82%): $^1H$ NMR ($CDCl_3$) 300 MHz 15.30 (s, 1H) 7.99 (d, J=7.9 Hz, 1H) 7.54 (m, 1H) 7.43 (m, 1H) 7.23 (m, 1H) 3.81 (s, 3H).

Step 2

Preparation of 4-[1,5-dihydro-3-(trifluoromethyl)-[2]benzothiopyrano[4,3-c]pyrazol-1-yl]benzenesulfonamide 4-Sulfonamidophenylhydrazine hydrochloride (0.81 g, 3.6 mmol) was added to a stirred solution of the diketone from Step 1 (0.83 g, 3.2 mmol) in ethanol (10 mL). The reaction was heated to reflux and stirred 2.1 hours. The reaction mixture was filtered and the filtrate concentrated in vacuo. The residue was dissolved in ethyl acetate, washed with water and with brine, dried over $MgSO_4$, reconcentrated in vacuo, and passed through a column of silica gel with 40% ethyl acetate to give the pyrazole (0.15 g, 11%): mp 230°–232° C.; $^1H$ NMR (acetone-$d_6$) 300 MHz 8.09 (d, J=8.7 Hz, 2H) 7.85 (d, J=8.9 Hz, 2H) 7.53 (d, J=7.7Hz, 1H) 7.40 (t, J=7.5 Hz,1H) 7.21 (t, J=7.7 Hz,1H) 6.93 (d, J=7.9 Hz, 1H) 6.79 (br s ,2H) 4.16 (s, 2H); $^{19}F$ NMR (acetone-$d_6$)) 300 MHz –62.94(s). High resolution mass spectrum Calc'd. for $C_{17}H_{12}F_3N_3O_2S_2$: 411.0323. Found: 411.0324.

EXAMPLE 17

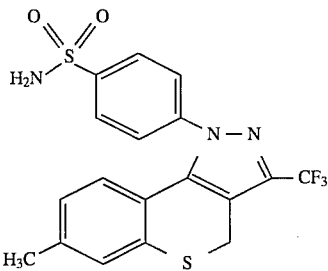

4-[1,5-Dihydro-7-methyl-3-(trifluoromethyl)-[2]benzothiopyrano[4,3-c]pyrazol-1-yl]benzenesulfonamide

Step 1

Preparation of S-(3-methylbenzyl)-isothiouronium chloride

Thiourea (26.19 g, 344 mmol) was added to a solution of α-chloro-m-xylene (48.21 g, 343 mmol) in methanol (50 mL). The reaction was heated to reflux and additional methanol (10 mL) was added to dissolve all of the thiourea. After 64.3 hours, the reaction was filtered and dried under vacuum to give a white solid (68.15 g, 92%): mp 182°–186° C.; $^1H$ NMR (DMSO-$d_6$) 300 MHz 9.34 (br s, 4H) 7.22 (m, 3H) 7.12 (m, 1H) 4.48 (s, 2H) 2.27 (s, 3H).

Step 2

Preparation of 3-(3-methylphenylthio)propanoic acid

A 250 mL flask was charged with the thiouronium salt from Step 1 (10.99 g, 51 mmol), sodium chloroacetate (8.86 g, 76 mmol), ethanol (95 mL) and water (10 mL). After heating to reflux, a solution of NaOH (9.05 g, 226 mmol) in water (50 mL) was added to the reaction dropwise over seven minutes. After stirring for 3.6 hours. the reaction was acidified with concentrated hydrochloric acid, extracted with ether, washed with brine, dried over $MgSO_4$ and concentrated in vacuo to give a white solid (9.95 g, 100%): mp 73°–75.5° C.; $^1H$ NMR ($CDCl_3$) 300 MHz 7.16 (m, 4H) 3.83 (s, 2H) 3.12 (s, 2H) 2.35 (s, 3H). Mass spectrum: M+=196.

Step 3

Preparation of 7-methylisothiochroman-4-one

The acid from Step 2 (6.06 g, 31 mmol) was dissolved in trifluoroacetic acid (11 mL), treated with trifluoroacetic anhydride (5 mL) and stirred at room temperature for 0.33 hours. The reaction was poured into 10% $Na_2CO_3$ (100 mL), extracted with ether, washed with brine, dried over $MgSO_4$, concentrated in vacuo, and recrystallized from ether/hexane to give 7-chloroisothiochroman-4-one (2.25 g, 41%) as a white solid: mp 79.5°–82° C.; $^1H$ NMR ($CDCl_3$) 300 MHz 7.97 (d, J=8.1 Hz, 1H) 7.17 (d, J=8.1 Hz, 1H) 7.00 (s, 1H) 3.87 (s, 2H) 3.52 (s, 2H) 2.37 (s, 3H). Mass spectrum: M+H=179.

Step 4

Preparation of 7-methyl-3-(trifluoroacetyl)isothiochroman-4-one

Ethyl trifluoroacetate (1.80 g, 12.7 mmol) was placed in a round bottom flask and dissolved in ether (10 mL). To the stirred solution was added 25% sodium methoxide (3.90 g, 18.0 mmol) followed by 7-chloroisothiochroman-4-one from Step 3 (2.25 g, 12.6 mmol) dissolved in ether (10 mL) and tetrahydrofuran (10 mL). The reaction was stirred at room temperature for 24.6 hours and treated with 3N hydrochloric acid. The organic layer was collected, washed with brine, dried over $MgSO_4$, concentrated in vacuo and passed through a column of silica gel with 20% ether/hexane to give the diketone (1.93 g, 56%) as a brown solid: $^1H$ NMR ($CDCl_3$) 300 MHz 15.45 (s, 1H) 7.88 (d, J=8.1 Hz, 1H) 7.25 (d, J=8.1 Hz, 1H) 7.06 (s, 1H) 3.77 (s, 2H) 2.43 (s, 2H); $^{19}F$ NMR ($CDCl_3$) 300 MHz: –72.76 (s). Mass spectrum: M+H= 275.

Step 5

Preparation of 4-[1,5-dihydro-7-methyl-3-(trifluoromethyl)-[2]benzothiopyrano[4,3-c]pyrazol-1-yl]benzenesulfonamide 4-Sulfonamidophenylhydrazine hydrochloride (1.68 g, 7.5 mmol) was added to a stirred solution of the diketone from Step 4 (1.93 g, 7.0 mmol) in ethanol (15 mL). The reaction was heated to reflux and stirred for 15.2 hours. The reaction mixture was concentrated in vacuo and the residue dissolved in ethyl acetate, washed with water and with brine, dried over $MgSO_4$, reconcentrated in vacuo and recrystallized from ethyl acetate/isooctane to give the pyrazole as a brown solid (1.48 g, 49%): mp 253°–255° C.; $^1$H NMR (acetone-$d_6$) 300 MHz 8.08 (d, J=8.7 Hz, 2H) 7.83 (d, J=8.7 Hz, 2H) 7.35 (s, 1H) 7.02 (d, J=8.1 Hz,1H) 6.78 (m, 3H) 4.11 (s, 2H) 2.34 (s, 3H); $^{19}$F NMR (acetone-$d_6$) 300 MHz −62.94 (s). High resolution mass spectrum Calc'd. for $C_{18}H_{14}F_3N_3O_2S_2$: 426.0558. Found: 426.05554.

EXAMPLE 18

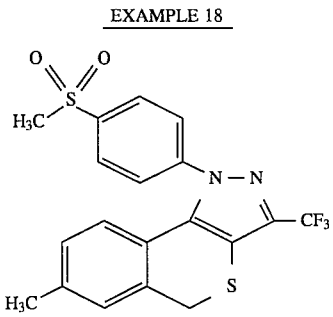

1,5-Dihydro-1-[4-(methylsulfonyl) phenyl]-7-methyl-3-(trifluoromethyl)-[2]benzothiopyrano[4,3-c]pyrazole

Step 1

Preparation of 1-[4-methylsulfonylphenyl]- 7-methyl-3-(trifluoromethyl)-1,5-dihydro-[2]benzothiopyrano[4,3-c] pyrazole 4-(Methylsulfonyl)phenylhydrazine (1.23 g, 6.6 mmol) was converted to the hydrochloride salt by stirring with a 4N solution of hydrochloric acid in dioxane (10 mL) for 25 minutes. The dioxane was removed in vacuo, and the 4-(methylsulfonyl)phenylhydrazine hydrochloride was combined with the diketone (Example 17, Step 4) (1.12 g, 2.9 mmol) and ethanol (20 mL), heated to reflux and stirred for 15.5. hours. The reaction mixture was filtered while hot and the filtrate was concentrated in vacuo. The residue was dissolved in ethyl acetate, washed with water and with brine, dried over $MgSO_4$, reconcentrated in vacuo, and passed through a column of silica gel eluting with 12% ethyl acetate/hexane to give the pyrazole (0.31 g, 18%) as a yellow solid: mp 207°–209° C.; $^1$H NMR (acetone-$d_6$) 300 MHz 8.14 (d, J=8.7 Hz, 2H) 7.92 (d, J=8.9 Hz, 2H) 7.35 (s, 1H) 7.35 (d, J=8.1 Hz, 1H) 6.83 (d, J=7.9 Hz, 1H) 4.11 (s, 2H) 3.23 (s, 3H) 2.34 (s, 3H); $^{19}$F NMR (acetone-$d_6$) 300 MHz −62.97 (s). High resolution mass spectrum Calc'd. for $C_{19}H_{15}F_3N_2O_2S_2$: 424.0527. Found: 424.0524.

EXAMPLE 19

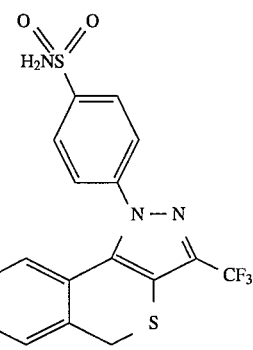

4-[7-Chloro-1,5-dihydro-3-(trifluoromethyl)-[2]benzothiopyrano[4,3-c]pyrazol-1-yl]benzenesulfonamide

Step 1

Preparation of S-(3-chlorobenzyl)isothiouronium chloride

3-Chlorobenzyl chloride (24.2 g, 0.15 mol) and thiourea (11.4 g, 0.15 mol) were dissolved in methanol (70 mL) and heated to reflux for 16 hours. The reaction was cooled to room temperature and a precipitate formed. Ether (150 mL) was added to complete the precipitation of compound. The crystals were isolated by filtration and washed with ether (100 mL). After drying in vacuo, 31.9 g (90%) of pure S-(3-chlorobenzyl)-isothiouronium chloride was obtained: $^1$H NMR (CD$_3$OD) δ=4.43p (s, 2H), 7.36p (s, 3H), 7.47p (s, 1H).

Step 2

Preparation of 3-chlorobenzylmercaptoacetic acid

S-(3-Chlorobenzyl)-isothiouronium chloride from Step 1 (11.86 g, 50 mmol) and chloroacetic acid (7.1 g, 75 mmol) were dissolved in ethanol (100 ml) and heated to 80° C. in a 4-neck flask equipped with nitrogen inlet, condenser and addition funnel. A solution of NaOH (10 g) in $H_2O$ (100 mL) and ethanol (50 mL) was added dropwise over 1 hour to this hot solution. The reaction was heated to 100° C. for 4 hours. The reaction was cooled to room temperature, acidified with concentrated hydrochloric acid (45 mL) and extracted with ether (500 mL). The organic layer was washed with brine (300 ml), dried over $MgSO_4$ and concentrated in vacuo to yield 10.84 g (100%) of 3-chlorobenzylmercaptoacetic acid which was used without further purification: $^1$H NMR (CDCl$_3$) δ=3.08p (s, 2H), 3.80p (s, 2H), 7.23p (m, 3H), 7.34p (s, 1H), 9.07p (broad s, 1H).

Step 3

Preparation of 7-chloroisothiochroman-4-one

3-Chlorobenzylmercaptoacetic acid from Step 2 (3.35 g) was dissolved in trifluoroacetic acid (50 mL). Trifluoroacetic acid anhydride (25 mL) was added and the reaction stirred at reflux, under a nitrogen atmosphere for 16 hours. The solution was carefully poured into 10% $Na_2CO_3$ solution (500 mL) which was stirring vigorously. The organics were extracted into ether (500 mL) and washed with brine (300 mL), dried over $MgSO_4$ and concentrated in vacuo. The resulting brown solid was purified by silica gel chromatography eluting with a 0–10% gradient of ethyl acetate in hexane to yield 7-chloroisothiochroman-4-one (1.57 g, 51%): $^1$H NMR (CDCl$_3$) δ=3.49p (d, 2H, J=0.8 Hz), 3.8p (s, 2H), 7:16p (m, 1H), 7.3p (dd, 1H, J=2.0, 8.4 Hz), 7.96p (d, 1H, J=8.5 Hz).

Step 4

Preparation of 7-chloro-3-(trifluoroacetyl)isothiochroman-4-one

7-Chloroisothiochroman-4-one from Step 3 (0.3 g, 1.5 mmol) was dissolved in tetrahydrofuran (15 mL) and cooled to −78° C. A solution of sodium bistrimethylsilyl amide (1.5 mL of a 1.0M tetrahydrofuran solution) was added and the reaction stirred for 0.5 hours at −78° C. Trifluoroacetyl imidazole (0.21 mL, 1.8 mmol) was added and the reaction was warmed to room temperature and stirred under a nitrogen atmosphere for 16 hours. 1N Hydrochloric acid (100 mL) was added to the reaction followed by extraction with ether (150 mL). The organics were washed with brine (75 mL), dried over MgSO$_4$ and concentrated in vacuo. The resulting yellow oil was used in the next step without further purification.

Step 5

Preparation of 4-[7-chloro-1,5-dihydro-3-(trifluoromethyl)-[2]benzothiopyrano[4,3-c]pyrazol-1-yl]benzenesulfonamide A mixtrue of the diketone from Step 4 (1.51 mmol) and 4-sulphonamidophenylhydrazine hydrochloride (0.41 g, 1.8 mmol) was dissolved in ethanol (50 mL) and heated to reflux for 16 hours. The reaction was concentrated in vacuo and the resulting solid was dissolved in ethyl acetate (200 mL). The organics were washed with water (200 mL) and with brine (150 mL), dried over MgSO$_4$ and concentrated in vacuo. The resulting oil was chromatographed on silia gel eluting with a gradient of ethyl acetate (from 10–50%) in hexane to yield pure tricyclic pyrazole (0.25 g, 40%): mp 241°–242° C.; $^1$H NMR (acetone-d$_6$) δ=4.18p (s, 2H), 6.79p (s, 2H), 6.94p (d, 1H, J=8.5 Hz), 7.26p (dd, 1H, J=2.2, 8.4 Hz), 7.6p (d, 1H, J=2.2 Hz), 7.83p (dd, 2H, J=2.1, 6.9 Hz), 8.1p (dd, 2H, J=2.1, 6.7 Hz); $^{19}$F NMR (acetone-d$_6$) δ=−62.94p (s, 3F).

EXAMPLE 20

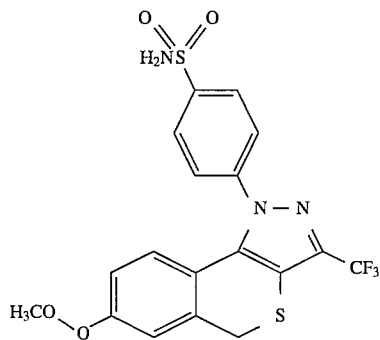

4-[1,5-Dihydro-7-methoxy-3-(trifluoromethyl)-[2]benzothiopyrano[4,3-c]pyrazol-1-yl]benzenesulfonamide

Step 1

Preparation of S-(3-methoxyphenylmethyl)isothiouronium chloride

A solution of 3-methoxybenzyl chloride (15.65 g, 0.1 mol) and thiourea (7.6 g, 0.1 mol) were dissolved in 40 mL of ethanol and heated to reflux for 16 hours, during this time the isothiouronium salt crystallized. The thiouronium chloride was isolated by filtration and recrystallized from ether and ethanol (21.85 g, 94%, mp 172.5°–174.0° C.). This material was used directly in the next step.

Step 2

Preparation of 3-methoxybenzylmercaptoacetic acid

The thiouronium chloride from Step 1 (20.00 g, 86 mmol) and chloroacetic acid (11.07 g, 95 mmol) were dissolved in ethanol (100 mL) and heated to 80° C. in a 4-neck flask equipped with nitrogen inlet, condenser and addition funnel. A solution of NaOH (10 g) in water (100 mL) and ethanol (50 mL) was added dropwise over 1 hour to the hot solution. The reaction was heated to 100° C. for 4 hours. The reaction was cooled to room temperature, acidified with concentrated hydrochloric acid (45 mL), and extracted with ether (500 mL). The organic layer was washed with brine (300 mL), dried over MgSO$_4$ and concentrated in vacuo to yield an oil that was vacuum distilled to provide 16.41 g (90%) of pure acid: bp 160°–170° C. at 0.2 mm; $^1$H NMR (CDCl$_3$/300 MHz) 3.1p (s, 2H), 3.8p (s, 3H), 3.82p (s, 2H), 6.8p (m, 1H), 6.91p (s, 1H), 6.96p (m, 1H), 7.23p (t, 1H, J=7.7 Hz), 8.33p (broad s, 1H), 11.1p(brs, 1H).

Step 3

Preparation of 7-methoxyisothiochroman-4-one 3-methoxybenzylmercaptoacetic acid from Step 2 (10.82 g) was dissolved in trifluoroacetic acid (50 mL). Trifluoroacetic acid anhydride (25 mL) was added and the reaction stirred under a nitrogen atmosphere for 0.25 hours. At this time, TLC showed no starting material. The solution was carefully poured into 10% Na$_2$CO$_3$ solution (500 mL) which was stirring vigorously. The organics were extracted into ether (500 mL) and washed with brine (300 mL), dried over MgSO$_4$ and concentrated in vacuo. The resulting brown solid was purified by silica gel chromatography eluting with 20% ethyl acetate in hexane to yield 7-methoxyisothiochroman-4-one (4.84 g, 49%): $^1$H NMR (CDCl$_3$) δ=3.48p (t, 2H, J=0.8 Hz), 3.83p (s, 3H), 3.84p (s, 2H), 6.6p (d, 1H, J=2.4 Hz), 6.83p (dd, 1H, J=2.4, 8.9 Hz), 8.0p (d, H, J=8.9 Hz).

Step 4

Preparation of 7-methoxy-3-(trifluoroacetyl)-isothiochroman-4-one

7-Methoxyisothiochroman-4-one from Step 3 (0.58 g, 3.0 mmol) was dissolved in tetrahydrofuran (30 mL) and cooled to −78° C. A solution of sodium bistrimethylsilylamide (3.0 mL of a 1.0M tetrahydrofuran solution) was added and the reaction stirred for 0.5 hours at −78° C. Trifluoroacetyl imidazole (0.41 mL, 3.6 mmol) was added and the reaction was warmed to room temperature and stirred under a nitrogen atmosphere for 16 hours. At this time, 1N hydrochloric acid (200 mL) was added to the reaction followed by extraction with ether (250 mL). The organics were washed with brine (150 mL), dried over MgSO$_4$ and concentrated in vacuo. The resulting yellow oil (0.42 g, 48%) was used without further purification.

Step 5

Preparation of 4-[1,5-dihydro-7-methoxy-3-(trifluoromethyl)-[2]benzothiopyrano[4,3-c]pyrazol-1-yl]benzenesulfonamide A solution of the dione from Step 4 (0.42 g, 1.4 mmol) and 4-sulphonamidophenylhydrazine hydrochloride (0.42 g, 1.8 mmol) were dissolved in ethanol (50 mL) and heated to reflux for 16 hours. The reaction was concentrated in vacuo and the resulting solid was dissolved in ethyl acetate (200 mL). The organics were washed with H₂O (200 mL) followed by brine (150 ml), dried over MgSO₄ and concentrated in vacuo. The resulting oil was chromatographed on silica gel eluting with a gradient of ethyl acetate (from 20–50%) in hexane to yield pure tricyclic pyrazole (0.25 g, 41%): mp 268°–270° C.; $^1$H NMR (acetone-d$_6$) δ=3.84p (s, 3H), 4.12p (s, 2H), 6.8p (m, 3H), 7.1p (d, 1H, J=2.4 Hz), 7.81p (d, 2H, J=6.6 Hz), 7.82p (s, 2H), 8.08p (dd, 2H, J=1.9, 6.6 Hz); $^{19}$F NMR (acetone-d$_6$) δ=−62.9p (s, 3F).

EXAMPLE 21

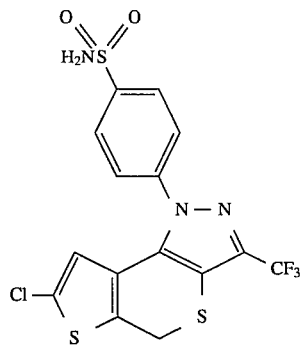

4-[7-Chloro-1,5-dihydro-3-trifluoromethylthieno[3',2':4,5]
thiopyrano[3,2-c]pyrazol-1-yl]benzenesulfonamide Step 1

Preparation of S-(5-chloro-2-thienylmethyl)-isothiouronium chloride

2-Chloro-5-(chloromethyl)thiophene (14.5 g, 87 mmol) and thiourea (6.6 g, 87 mol) were dissolved in methanol (30 mL) and heated to reflux for 16 hours. The reaction was cooled to room temperature and a precipitate formed. Ether (150 mL) was added to complete the precipitation of compound. The crystals were isolated by filtration and washed with ether (100 mL). After drying in vacuo, 19.0 g (90%) of pure S-(5-chloro-2-thienylmethyl)-isothiouronium chloride were obtained: $^1$H NMR (CD$_3$OD) δ=4.83p (s, 2H), 6.87p (d, 1H, J=3.8 Hz), 6.96p (d, 1H, J=3.2 Hz).

Step 2

Preparation of 5-chloro-2-thienylmethylmercaptoacetic acid

The compound from Step 1 (12.16 g, 50 mmol) and chloroacetic acid (7.1 g, 75 mmol) were dissolved in ethanol (100 mL) and heated to 80° C. in a 4-neck flask equipped with nitrogen inlet, condenser and addition funnel. A solution of NaOH (10 g) in water (100 mL) and ethanol (50 mL) was added dropwise over 1 hour to the hot solution. The reaction was heated to 100° C. for 4 hours. The reaction was cooled to room temperature, acidified with concentrated hydrochloric acid (45 mL) and extracted with ether (500 mL). The organic layer was washed with brine (300 mL), dried over MgSO₄ and concentrated in vacuo to yield 11.14 g (100%) of pure acid which was used without further purification: $^1$H NMR (CDCl$_3$) δ=3.2p (s, 2H), 3.98p (s, 2H), 6.73p (d, 1H, J=3.6 Hz), 6.77p (d, 1H, J=3.8 Hz).

Step 3

Preparation of 6-chloro-5,6-dihydro-4H-thieno[2,3-b]thiopyran-4-one

The acid from Step 2 (4.45 g) was dissolved in trifluoroacetic acid (45 mL). Trifluoroacetic acid anhydride (20 mL) was added and the reaction was stirred under a nitrogen atmosphere for 0.25 hours. At this time, TLC showed no starting material. The solution was carefully poured into 10% Na$_2$CO$_3$ solution (600 mL) which was stirring vigorously. The organics were extracted into ethyl acetate (500 mL), washed with brine (300 mL), dried over MgSO₄ and concentrated in vacuo. The resulting brown solid was purified by SiO$_2$ chromatography eluting with 10% ethyl acetate in hexane to yield of pure intermediate (2.5 g, 61%): $^1$H NMR (CDCl$_3$) δ=3.33p (d, 2H, J=0.6 Hz), 3.78p (s, 2H), 7.1p (s, 1H).

Step 4

Preparation of 6-chloro-5,6-dihydro-3-trifluoroacetyl-4H-thieno[2,3-b]thiopyran- 4-one The compound from Step 3 (1.03 g, 5.0 mmol) was dissolved in tetrahydrofuran (50 mL) and cooled to −78° C. A solution of sodium bistrimethylsilylamide (5.0 mL of a 1.0M tetrahydrofuran solution) was added and the reaction stirred for 0.75 hours at −78° C. Trifluoroacetyl imidazole (0.68 mL, 6.0 mmol) was added and the reaction was warmed to room temperature and stirred under a nitrogen atmosphere for 16 hours. At this time, 1N hydrochloric acid (300 mL) was added to the reaction followed by extraction with ether (350 mL). The organics were washed with brine (200 mL), dried over MgSO₄ and concentrated in vacuo. The resulting yellow oil was used without further purification.

Step 5

Preparation of 4-[7-chloro-1,5-dihydro-3-trifluoromethyl-thieno[3',2':4,5]thiopyrano[3,2-c]pyrazol- 1-yl]benzenesulfonamide The compound from Step 4 (5.5 mmol) and 4-sulphonamidophenylhydrazine hydrochloride (1.47 g, 6.6 mmol) were dissolved in ethanol (100 mL) and heated to reflux for 16 hours. The reaction was concentrated in vacuo and the resulting solid dissolved in ethyl acetate (300 mL). The organics were washed with water (300 mL) followed by brine (200 mL) and were then dried over MgSO₄ and concentrated in vacuo. The resulting oil was chromatographed on silica gel eluting with a gradient of ethyl acetate (from 20–40%) in hexane. This product was first crystallized from ethyl acetate and isooctane, then from ethanol and water to yield pure 4-[7-chloro-1,5-dihydro-3-trifluoromethylthieno[3',2':4,5]thiopyrano[3,2-c]pyrazol-1-yl]benzenesulfonamide [0.35 g, 16% from Step 2]: mp 218°–220° C. (dec); $^1$H NMR (CDCl$_3$) δ=4.0p (s, 2H), 6.27p (s, 2H), 7.32p (s, 1H), 7.61(d, 2H, J=7.0 Hz), 8.02p (d, 2H, J=7.0 Hz); $^{19}$F NMR (acetone-d$_6$) δ=−59.25p (s, 3F).

EXAMPLE 22

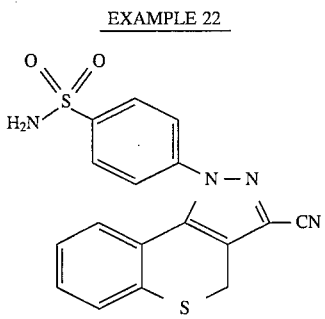

1-[4-(Aminosulfonyl)phenyl]-1,4-dihydro-[1]benzothiopyrano[4,3-c]-pyrazol-3-carbonitrile

Step 1

Preparation of 1-[4-(aminosulfonyl)phenyl]- 1,4-dihydro-[1]benzothiopyrano[4,3-c]pyrazol-3-carboxamide The compound from Example 8 (11.31 g, 28.3 mmol) was placed in a 500 mL flask with methanol (200 mL), anhydrous ammonia was bubbled through the solution, the flask was capped and allowed to stand. After 14 days the reaction was concentrated in vacuo and recrystallized from ethyl acetate to give the carboxamide as yellow solid (10.14 g, 93%): mp 238°–242° C.; $^1$H NMR (acetone-$d_6$) 300 MHz 8.07 (d, J=8.7 Hz, 2H) 7.72 (d, J=8.7 Hz, 2H) 7.49 (d, J=7.9 Hz, 1H) 7.30 (br s, 1H) 7.23 (dd, 1H) 7.02 (dd, 1H) 6.91 (d, J=7.9 Hz, 1H) 6.80 (br s, 2H) 6.75 (br s, 1H) 4.28 (s, 2H). Mass spectrum: M+H=387.

Step 2

Preparation of 1-[4-(aminosulfonyl)phenyl]- 1,4-dihydro-[1]benzothiopyrano[4,3-c]pyrazol-3-carbonitrile Dimethylformamide (10 mL) (DMF) was placed in a 250 mL flask and cooled to 0° C. Oxalyl chloride (2 mL, 23 mmol) was added and stirred for 15 minutes. A solution of the product from Step 1 (3.34 g, 9 mmol) in DMF (13 mL) was added and the reaction was stirred for 0.8 hours, treated with pyridine (3.8 mL, 47 mmol), poured into 3N hydrochloric acid (30 mL) and filtered to give a solid (2.86 g). The filtrate was extracted with dichloromethane, washed with 3N hydrochloric acid and with saturated NaHCO$_3$, dried over MgSO$_4$, concentrated in vacuo, combined with the previously collected solid, purified by flash chromatography on silica gel eluting with 1% methanol/dichloromethane, and recrystallized from dichloromethane/isooctane to give a solid (2.44 g, mp 220°–222° C.) which was the DMF adduct of the desired product. The DMF adduct (2.44 g) was dissolved in dioxane (18 mL) and treated with a 4N solution of hydrochloric acid in dioxane (10 mL). The solution was stirred at room temperature for 7.25 hours, heated to reflux for 42 hours, filtered, and concentrated in vacuo. The residue was dissolved in methylene chloride, washed wtih water, dried over MgSO$_4$, and reconcentrated in vacuo to give a brown foam (2.43 g) which was a mixture of the desired product and its adduct with DMF. The mixture was purified by flash chromatography on silica gel eluting with 40% ethyl acetate/hexane to give the desired product as a white solid (0.62 g, 19%): mp 211°–213° C.; $^1$H NMR (acetone-$d_6$) 300 MHz 8.10 (d, J=8.5 Hz, 2H) 7.76 (d, J=8.5 Hz, 2H) 7.54 (d, J=7.7 Hz, 1H) 7.30 (dd, 1H) 7.07 (dd, 1H) 6.94 (d, J=8.1 Hz, 1H) 6.82 (br s, 2H) 4.12 (s, 2H). High resolution mass Calc'd. for $C_{17}H_{12}N_4O_2S_2$: 368.0402. Found: 368.0368.

EXAMPLE 23

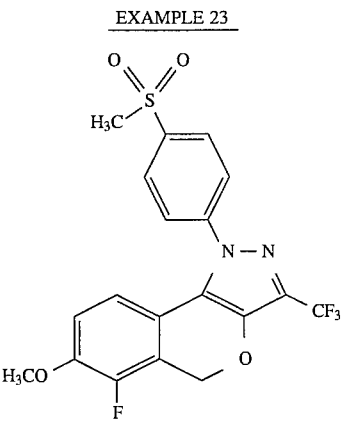

4-[1,4-Dihydro-6-fluoro-7-methoxy-3-(trifluoromethyl)[1]benzopyrano[4,3-c]pyrazol-1-yl]benzenesulfonamide

Step 1

Preparation of 2-fluoro-3-methoxyphenyl)-3-oxo-propanoic acid

A solution of 2-fluoro-3-methoxybenzyl alcohol (1.57 g, 9.22 mmol), chloroacetic acid (1.72 g, 18.2 mmol), and ethanol (0.04 mL) in 20 mL of anhydrous tetrahydrofuran was added to a mixture of sodium hydride (2.29 g, 95.2 mmol) in 10 mL of anhydrous tetrahydrofuran dropwise over 10 minutes at 0° C. The cooling bath was removed and the solution warmed to room temperature and then was heated to reflux for 14 hours. The solution was cooled to room temperature, acidified with 3N hydrochloric acid, and extracted with ether. The ethereal phase was washed with brine, dried over anhydrous MgSO$_4$, filtered, and concentrated in vacuo to provide a yellow solid (2.04 g, 100%) that was used directly in the next step: $^1$H NMR (CDCl$_3$/300 MHz) 8.60 (brs, 1H), 7.08–6.93 (m, 3H), 4.72 (d, J=1.4 Hz, 2H), 4.17 (s, 2H), 3.88 (s, 3H); $^{19}$F NMR (CDCl$_3$/282 MHz) –141.50 (t). Mass spectrum M+Li=221.

Step 2

Preparation of 7-methoxy-8-fluoroisochroman- 4-one

A solution of 2-fluoro-3-methoxyphenyl)-3-oxo-propanoic acid from Step 1 (1.96 g, 8.6 mmol) in 4 mL of trifluoroacetic acid and 2 mL of trifluoroacetic anhydride was stirred at room temperature for 1 hour. The solution was concentrated in vacuo, the residue dissolved in ether, and the ethereal solution was washed with saturated aqueous NaHCO$_3$, brine, dried over anhydrous MgSO$_4$, filtered and concentrated in vacuo to give a solid that was purified by flash chromatography to provide 0.37 g (32%) of the desired ketone. The aqueous phase from the NaHCO$_3$ was acidified, extracted with ether, washed with brine, dried over anhydrous MgSO$_4$, filtered, and concentrated in vacuo to provide 1.13 g, of recovered 2-fluoro-3-methoxyphenyl)- 3-oxopropanoic acid: mp 112°–118° C.; $^1$H NMR (CDCl$_3$/300 MHz) 7.86 (dd, J=8.66, 1.41 Hz, 1H), 7.00 (apparent t, J=8.26 Hz, 1H), 4.96 (s, 2H), 4.31 (S, 2H), 3.97 (S, 3H); $^{19}$F NMR (CDCl$_3$/282 MHz) –142.2 (d). Mass spectrum M$^+$=196.

Step 3

Preparation of 7-methoxy-8-fluoro-3-(trifluoroacetyl)isochroman- 4-one

A solution of 7-methoxy-8-fluoroisochroman- 4-one from Step 2 (370 mg, 1.76 mmol) and ethyl trifluoroacetate (290 mg, 2.04 mmol) in 8 mL of anhydrous tetrahydrofuran was treated with a solution of 25% sodium methoxide in methanol (570 mg, 2.64 mmol). The solution was stirred at room temperature for 16 hours, treated with excess 3N hydrochloric acid, and extracted with ether. The ethereal extract was washed with brine, dried over anhydrous $MgSO_4$, filtered and concentrated in vacuo to afford 450 mg (88%) of pure 7-methoxy-8-fluoro-3-(trifluoroacetyl)isochroman- 4-one which was used directly in the next step without further purification.

Step 4

Preparation of 4-[6-fluoro-1,4-dihydro-7-methoxy- 3-(trifluoromethyl)-[1]benzopyrano[4,3-c]pyrazol- 1-yl]benzonesulfonamide 7-Methoxy-8-fluoro-3-(trifluoroacetyl)isochroman- 4-one from Step 3 (450 mg, 1.47 mmol) and 4-sulfonamidophenylhydrazine hydrochloride (430 mg, 1.92 mmol) were dissolved in 5 mL of anhydrous ethanol and heated to reflux for 45 minutes. The solution was concentrated in vacuo and the residue was dissolved in ethyl acetate. The solution was washed with 3N hydrochloric acid, brine, dried over anhydrous $MgSO_4$, filtered, and concentrated in vacuo. The residue was crystallized from a mixture of isooctane and ethyl acetate to afford 4-[1,4-dihydro-6-fluoro-7-methoxy-3-(trifluoromethyl)-[1]benzopyrano[4,3-c]pyrazol-1-yl] benzenesulfonamide as a white solid (200 mg, 30%): mp 289.5°–291.0° C.; $^1$H NMR (acetone $d_6$/300 MHz) 8.12 (d, J=8.4 Hz, 2H), 7.90 (d, J=8.5 Hz. 2H), 7.07 (dd, J=8.7, 8.5 Hz, 1H), 6.83 (br s, 2H), 6.75 (d, J=8.7 Hz, 1H), 5.45 (s, 2H), 3.90 (s, 3H); $^{19}$F NMR (acetone $d_6$/282 MHz) −62.51 (s) , −140.97 (d). High resolution mass spectrum Calc'd. for $C_{18}H_{13}F_4N_3O_4S$: 443.0563. Found: 443.0570.

The following compounds were obtained according to procedures similar to that exemplified above and in the General Synthetic Schemes.

24) 4-[7-chloro-1,5-dihydro-3-trifluoromethyl-thieno[3', 2':4,5]thiopyrano-s-oxide[3,2-c]pyrazol-1-yl]benzenesulfonamide: mp=85° C. (dec).

25) 4-[3-(difluoromethyl)-1,5-dihydro-6-fluoro- 7-methoxy-[2]benzothiopyrano[4,3-c]pyrazol-1-yl]benzenesulfonamide: mp=256°–258° C.

26) 4-[1,5-dihydro-7-fluoro-3-(trifluoromethyl)-[2]benzothiopyrano[4,3-c]pyrazol-1-yl]benzenesulfonamide: mp=240°–242° C.

27) [1-(4-aminosulfonylphenyl)-1,5-dihydro- 7-fluoro-[2]benzothiopyrano[4,3-c]pyrazol-3-yl]carboxamide: mp=297°–298° C.

28) 4-[1,5-dihydro-6-fluoro-7-methoxy-3-(trifluoromethyl)-[2]benzothiopyrano-S-oxide[4,3-c]pyrazol-1-yl]benzenesulfonamide: mp=>300° C.

29) methyl [1-(4-aminosulfonylphenyl)-1,5-dihydro-7-fluoro-[2]benzothiopyrano[4,3-c]pyrazol-3-yl]carboxylate: mp=241°–244° C.

30) 4-[4,6-dihydro-7-fluoro-8-methoxy-3-(trifluoromethyl)-[2]benzothiepino[5,4-c]pyrazol-1-yl]benzenesulfonamide: mp=>133°–138° C.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

Rat Carrageenan-induced Analgesia Test

The analgesia test using rat carrageenan was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Example | RAT PAW EDEMA % Inhibition[1] | ANALGESIA % Inhibition[1] |
|---|---|---|
| 1 | 43 | 35 |
| 2 | 28 | 29 |
| 21 | 26 | 14 |

[1] @ 30 mg/kg body weight

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant COX baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M. D. Summers and G. E. Smith, *A Manual of Methods for Baculovirus Vectors and Insect Cell Culture Procedures,* Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II activity

COX activity was assayed as PGE$_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The PGE$_2$ formed was measured by standard ELISA technology (Cayman Chemical). Results are shown in Table II.

TABLE II

| Example | Human COX II (D$_{50}$ µM) | Human COX I ID$_{50}$ µM |
|---|---|---|
| 1 | <.1 | 2.7 |
| 2 | <.1 | >100 |
| 3 | 1.3 | 7.1 |
| 4 | .5 | |
| 5 | 4.8 | 24.4 |
| 6 | 23.5 | 11.1 |
| 7 | .5 | 9.7 |
| 8 | .5 | |
| 9 | 48.2 | >100 |
| 10 | <.1 | 6.2 |
| 11 | 52 | >100 |
| 12 | 95 | >100 |
| 13 | <.1 | <.1 |
| 14 | .2 | 4.6 |
| 15 | <.1 | .3 |
| 16 | <.1 | .4 |
| 17 | <.1 | .8 |
| 18 | <.1 | 3.7 |
| 19 | <.1 | .30 |
| 20 | <.1 | <.1 |
| 21 | <.1 | 8.7 |
| 22 | 3.5 | 51 |
| 24 | 45.6 | 91.1 |
| 25 | <.1 | >100 |
| 26 | <.1 | .3 |
| 27 | 4.7 | >100 |
| 28 | 1.2 | >100 |
| 29 | .8 | 13.2 |
| 30 | 2.2 | 73.4 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

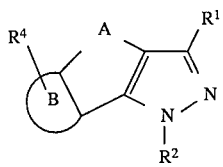

wherein A is —(CH$_2$)$_m$—X—(CH$_2$)$_n$—;
wherein X is selected from S(O)$_p$, and O;
wherein m is 0 to 3, inclusive;
wherein n is 0 to 3, inclusive;
wherein p is 0 to 2, inclusive;
wherein B is heteroaryl;
wherein R$^1$ is selected from hydrido, halo, haloalkyl, cyano, nitro, formyl, alkoxycarbonyl, carboxyl, carboxyalkyl, alkoxycarbonylalkyl, amidino, cyanoamidino, aminocarbonyl, alkoxy, alkoxyalkyl, aminocarbonylalkyl, N-alkylaminocarbonyl, N-arylaminocarbonyl, N,N-dialkylaminocarbonyl, N-alkyl-N-arylaminocarbonyl, alkylcarbonyl, alkylcarbonylalkyl, hydroxyalkyl, alkylthio, alkylsulfinyl, alkylsulfonyl, alkylthioalkyl, alkylsulfinylalkyl, alkylsulfonylalkyl, N-alkylsulfamyl, N-arylsulfamyl, arylsulfonyl, N, N-dialkylsulfamyl, N-alkyl-N-arylsulfamyl and heterocyclic;
wherein R$^2$ is selected from aryl and heteroaryl, wherein R$^2$ is optionally substituted at a substitutable position with one or more radicals selected from alkylsulfonyl, sulfamyl, halo, alkyl, alkoxy, hydroxyl and haloalkyl; and
wherein R$^4$ is one or more radicals selected from hydrido, halo, alkylthio, alkylsulfinyl, alkyl, alkylsulfonyl, cyano, carboxyl, alkoxycarbonyl, amido, N-alkylaminocarbonyl, N-arylaminocarbonyl, N,N-dialkylaminocarbonyl, N-alkyl-N-arylaminocarbonyl, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino;
provided either R$^4$ is sulfamyl or alkylsulfonyl, or R$^2$ is substituted with sulfamyl or alkylsulfonyl;
or a pharmaceutically-acceptable salt thereof.

2. Compound of claim 1 wherein A is —(CH$_2$)$_m$—X—(CH$_2$)$_n$—;
wherein X is selected from S(O)$_p$, and O;
wherein m is 0 to 3, inclusive;
wherein n is 0 to 3, inclusive;
wherein p is 0 to 2, inclusive;
wherein B is selected from five and six membered heteroaryl;
wherein R$^1$ is selected from halo, lower haloalkyl, cyano, nitro, formyl, lower alkoxycarbonyl, lower carboxyalkyl, lower alkoxycarbonylalkyl, amidino, cyanoamidino, lower alkoxy, lower alkoxyalkyl, aminocarbonyl, lower aminocarbonylalkyl, lower N-alkylaminocarbonyl, N-phenylaminocarbonyl, lower N,N-dialkylaminocarbonyl, lower N-alkyl-N-phenylaminocarbonyl, lower alkylcarbonyl, lower alkylcarbonylalkyl, lower hydroxyalkyl, lower alkylthio, lower alkylsulfinyl, lower alkylsulfonyl, lower alkylthioalkyl, lower alkylsulfinylalkyl, lower alkylsulfonylalkyl, lower N-alkylsulfamyl, N-phenylsulfamyl, phenylsulfonyl, lower N,N-dialkylsulfamyl, lower N-alkyl-N-phenylsulfamyl and five-seven membered heterocyclic;
wherein R$^2$ is selected from phenyl and five or six membered heteroaryl, wherein R$^2$ is optionally substituted at a substitutable position with one or more radicals selected from lower alkylsulfonyl, sulfamyl, halo, lower alkyl, lower alkoxy, hydroxyl and lower haloalkyl; and
wherein R$^4$ is one or more radicals selected from hydrido, halo, lower alkylthio, lower alkylsulfinyl, lower alkyl, lower alkylsulfonyl, cyano, carboxyl, lower alkoxycarbonyl, aminocarbonyl, lower N-alkylaminocarbonyl, N-phenylaminocarbonyl, lower N,N-dialkylaminocarbonyl, lower N-alkyl-N-phenylaminocarbonyl, lower haloalkyl, hydroxyl, lower alkoxy, lower hydroxyalkyl, lower haloalkoxy, sulfamyl, lower N-alkylsulfamyl, amino, lower N-alkylamino, lower N,N-dialkylamino, five-seven membered heterocyclic, nitro and acylamino;
or a pharmaceutically-acceptable salt thereof.

3. Compound of claim 2 wherein A is —(CH$_2$)$_m$—X—(CH$_2$)$_n$—; wherein X is S(O)$_p$ or O; wherein m is 0, 1 or 2; wherein n is 0, 1 or 2; wherein p is 0, 1 or 2; wherein B is selected from five and six membered heteroaryl; wherein R$^1$ is selected from halo, lower haloalkyl, cyano, formyl, lower alkoxycarbonyl, aminocarbonyl, lower alkoxycarbonylalkyl, lower alkoxy, lower alkoxyalkyl, lower aminocarbonylalkyl, lower N-alkylaminocarbonyl, N-phenylaminocarbonyl, lower N,N-dialkylaminocarbonyl, lower N-alkyl-N-phenylaminocarbonyl and lower hydroxyalkyl; wherein R$^2$ is phenyl substituted at a substitutable position with a radical selected from lower alkylsulfonyl and sulfamyl; and wherein R$^4$ is one or more radicals selected from hydrido, halo, lower alkylthio, lower alkylsulfinyl, lower alkyl, lower alkylsulfonyl, cyano, carboxyl, lower alkoxycarbonyl, aminocarbonyl, lower N-alkylaminocarbonyl, lower N,N-dialkylaminocarbonyl, lower N-alkyl-N-phenylaminocarbonyl, lower haloalkyl, hydroxyl, lower alkoxy, lower hydroxyalkyl, amino, lower N-alkylamino, lower N,N-dialkylamino, lower haloalkoxy and nitro; or a pharmaceutically-acceptable salt thereof.

4. Compound of claim 3 wherein A is —(CH$_2$)$_m$—X—(CH$_2$)$_n$—; wherein X is S(O)$_p$ or O; wherein m is 0 or 1; wherein n is 0 or 1; wherein p is 0 or 1; wherein B is selected from five and six membered heteroaryl; wherein R$^1$ is selected from lower haloalkyl, cyano, formyl, lower alkoxycarbonyl, lower alkoxy, lower N-alkylaminocarbonyl, N-phenylaminocarbonyl, lower N,N-dialkylaminocarbonyl and lower N-alkyl-N-phenylaminocarbonyl; wherein R$^2$ is phenyl substituted at a substitutable position with a radical selected from lower alkylsulfonyl and sulfamyl; and wherein R$^4$ is one or more radicals selected from hydrido, halo, lower alkylthio, lower alkylsulfinyl, lower alkyl, cyano, carboxyl, lower alkoxycarbonyl, aminocarbonyl, lower haloalkyl, hydroxyl, lower alkoxy, amino, lower N-alkylamino, lower N,N-dialkylamino, lower hydroxyalkyl and lower haloalkoxy; or a pharmaceutically-acceptable salt thereof.

5. Compound of claim 4 wherein A is —(CH$_2$)$_m$—X—(CH$_2$)$_n$—; wherein X is S(O)$_p$ or O; wherein m is 0 or 1; wherein n is 0 or 1; wherein p is 0 or 1; wherein B is selected from thienyl, pyridyl, furyl, oxazolyl, thiazolyl, imidazolyl, pyrazolyl, isoxazolyl, isothiazolyl, triazolyl, pyridazinyl, pyrimidinyl, pyrazinyl, triazinyl, thiaimidazolyl, oxoimidazolyl, azaoxazolyl, azathiazolyl and pyrrolyl;
wherein R$^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, formyl, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, methoxy, ethoxy, propoxy, n-butoxy, N-methylaminocarbonyl, N-phenylaminocarbonyl, N,N-dimethylaminocarbonyl, N-methyl-N-phenylaminocarbonyl and methylcarbonyl;

wherein $R^2$ is phenyl substituted at a substitutable position with a radical selected from methylsulfonyl and sulfamyl;

wherein $R^4$ is optionally substituted with one or more radicals selected from hydrido, fluoro, chloro, bromo, methylthio, ethylthio, isopropylthio, tert-butylthio, isobutylthio, hexylthio, methylsulfinyl, ethylsulfinyl, isopropylsulfinyl, tert-butylsulfinyl, isobutylsulfinyl, hexylsulfinyl, methyl, ethyl, isopropyl, tert-butyl, isobutyl, hexyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl and trifluoromethoxy; or a pharmaceutically-acceptable salt thereof.

6. Compound of claim 5 which is 4-[7-chloro- 1,5-dihydro-3-trifluoromethyl-[2]thienothiopyrano[4,3-c]pyrazol-1-yl]benzenesulfonamide, or a pharmaceutically-acceptable salt thereof.

7. A compound of Formula II

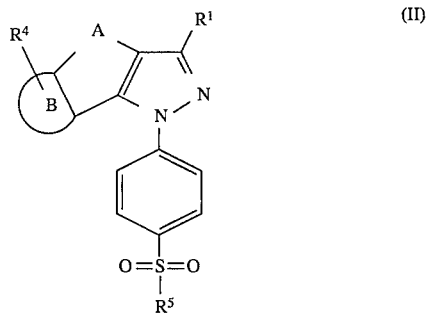

(II)

wherein A is —(CH$_2$)$_m$—X—(CH$_2$)$_n$—;

wherein X is S(O)$_p$ or O;

wherein m is 0 or 1;

wherein n is 0 or 1;

wherein p is 0 or 1;

wherein B is heteroaryl;

wherein $R^1$ is selected from haloalkyl, aminocarbonyl, alkoxycarbonyl and cyano;

wherein $R^4$ is one or more radicals selected from hydrido, halo, alkyl and alkoxy; and wherein $R^5$ is selected from alkyl and amino;

or a pharmaceutically-acceptable salt thereof.

8. Compound of claim 7 wherein A is —(CH$_2$)$_m$—X—(CH$_2$)$_n$—; wherein X is S(O)$_p$ or O; wherein m is 0 or 1; wherein n is 0 or 1; wherein p is 0 or 1; wherein B is five membered heteroaryl; wherein $R^1$ is selected from lower haloalkyl, aminocarbonyl, lower alkoxycarbonyl and cyano; wherein $R^4$ is one or more radicals selected from hydrido, halo, lower alkyl and lower alkoxy; and wherein $R^5$ is selected from lower alkyl and amino; or a pharmaceutically-acceptable salt thereof.

9. Compound of claim 8 wherein A is —(CH$_2$)$_m$—X—(CH$_2$)$_n$—; wherein X is S(O)$_p$ or O; wherein m is 0 or 1; wherein n is 0 or 1; wherein p is 0 or 1; wherein B is selected from thienyl, furyl and pyrrolyl; wherein $R^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, aminocarbonyl, methoxycarbonyl, ethoxycarbonyl, propoxycarbonyl, butoxycarbonyl and cyano; wherein $R^4$ is one or more radicals selected from hydrido, fluoro, chloro, bromo, methyl, ethyl, isopropyl, tert-butyl, isobutyl, hexyl, methoxy, methylenedioxy, ethoxy, propoxy, n-butoxy and tert-butoxy; and wherein $R^5$ is selected from methyl and amino; or a pharmaceutically-acceptable salt thereof.

10. Compound of claim 5 selected from compounds, and their pharmaceutically acceptable salts, of the group consisting of 4-[7-chloro-1,5-dihydro-3-trifluoromethyl-[2]thienothiopyrano[4,3- c]pyrazol-1-yl]benzenesulfonamide;

4-[7-chloro-1,5-dihydro-3-trifluoromethylthieno[3',2':4,5] thiopyrano[3,2-c]pyrazol-1-yl]benzenesulfonamide;

4-[7- chloro-1,5- dihydro-3- trifluoromethylthieno[3',2':4,5] thiopyrano-S-oxide[3,2-c]pyrazol-1-yl]benzenesulfonamide;

4-[1,5-dihydro-3-(trifluoromethyl)furano[2',3':4,5]thiopyrano [3,2- c]pyrazol-1-yl]benzenesulfonamide;

4-[1,5-dihydro-3-(trifluoromethyl)oxazolo[4',5':4,5]thiopyrano [3,2-c]pyrazol-1-yl]benzenesulfonamide;

4-[1,5-dihydro-3-(trifluoromethyl)thiazolo[5',4':4,5]thiopyrano [3,2-c]pyrazol-1-yl]benzenesulfonamide;

1,5-dihydro-1-(4-methoxyphenyl)-3-(trifluoromethyl)thieno[3',2':4,5]thiopyrano [3,2-c]pyrazole-7-sulfonamide; and 4-[1,5-dihydro-3-(trifluoromethyl)pyrazolo[3',4':5,6]thiopyrano [3,4-b]pyridin-1-yl]benzenesulfonamide.

11. A pharmaceutical composition comprising a therapeutically-effective amount of a compound, said compound selected from a family of compounds of claim 1; or a pharmaceutically-acceptable salt thereof.

12. A pharmaceutical composition comprising a therapeutically-effective amount of a compound, said compound selected from a family of compounds of claim 2; or a pharmaceutically-acceptable salt thereof.

13. A pharmaceutical composition comprising a therapeutically-effective amount of a compound, said compound selected from a family of compounds of claim 3; or a pharmaceutically-acceptable salt thereof.

14. A pharmaceutical composition comprising a therapeutically-effective amount of a compound, said compound selected from a family of compounds of claim 4; or a pharmaceutically-acceptable salt thereof.

15. A pharmaceutical composition comprising a therapeutically-effective amount of a compound, said compound selected from a family of compounds of claim 5; or a pharmaceutically-acceptable salt thereof.

16. A pharmaceutical composition comprising a therapeutically-effective amount of a compound, said compound selected from a family of compounds of claim 10; or a pharmaceutically-acceptable salt thereof.

17. A pharmaceutical composition comprising a therapeutically-effective amount of a compound, said compound selected from a family of compounds of claim 6; or a pharmaceutically-acceptable salt thereof.

18. A method of treating inflammation or an inflammation-associated disorder in a subject, said method comprising administering to the subject having or susceptible to said inflammation or inflammation-associated disorder, a therapeutically-effective amount of a compound of claim 1; or a pharmaceutically-acceptable salt thereof.

19. A method of treating inflammation or an inflammation-associated disorder in a subject, said method comprising administering to the subject having or susceptible to said inflammation or inflammation-associated disorder, a therapeutically-effective amount of a compound of claim 2; or a pharmaceutically-acceptable salt thereof.

20. A method of treating inflammation or an inflammation-associated disorder in a subject, said method comprising administering to the subject having or susceptible to said inflammation or inflammation-associated disorder, a therapeutically-effective amount of a compound of claim 3; or a pharmaceutically-acceptable salt thereof.

21. A method of treating inflammation or an inflammation-associated disorder in a subject, said method comprising administering to the subject having or susceptible to said inflammation or inflammation-associated disorder, a therapeutically-effective amount of a compound of claim 4; or a pharmaceutically-acceptable salt thereof.

22. A method of treating inflammation or an inflammation-associated disorder in a subject, said method comprising administering to the subject having or susceptible to said inflammation or inflammation-associated disorder, a therapeutically-effective amount of a compound of claim 5; or a pharmaceutically-acceptable salt thereof.

23. A method of treating inflammation or an inflammation-associated disorder in a subject, said method comprising administering to the subject having or susceptible to said inflammation or inflammation-associated disorder, a therapeutically-effective amount of a compound of claim 10; or a pharmaceutically-acceptable salt thereof.

24. A method of treating inflammation or an inflammation-associated disorder in a subject, said method comprising administering to the subject having or susceptible to said inflammation or inflammation-associated disorder, a therapeutically-effective amount of a compound of claim 6; or a pharmaceutically-acceptable salt thereof.

25. The method of claim 18 for use in treatment of inflammation.

26. The method of claim 18 for use in treatment of an inflammation-associated disorder.

27. The method of claim 26 wherein the inflammation-associated disorder is arthritis.

28. The method of claim 26 wherein the inflammation-associated disorder is pain.

29. The method of claim 26 wherein the inflammation-associated disorder is fever.

\* \* \* \* \*